US009593342B2

(12) United States Patent
Shasky et al.

(10) Patent No.: US 9,593,342 B2
(45) Date of Patent: *Mar. 14, 2017

(54) METHODS FOR PRODUCING POLYPEPTIDES IN ENZYME-DEFICIENT MUTANTS OF *FUSARIUM VENENTATUM*

(71) Applicant: Novozymes, Inc., Davis, CA (US)

(72) Inventors: Jeffrey Shasky, Davis, CA (US); Wendy Yoder, Billingshurst (GB)

(73) Assignee: NOVOZYMES, INC., Davis ( * ) Notice: Subject to any disclaimer, the term of this patent is extended or adjusted under 35 U.S.C. 154(b) by 0 days.

This patent is subject to a terminal disclaimer.

(21) Appl. No.: 14/974,879

(22) Filed: Dec. 18, 2015

(65) Prior Publication Data

US 2016/0102315 A1    Apr. 14, 2016

Related U.S. Application Data

(63) Continuation of application No. 14/168,766, filed on Jan. 30, 2014, now Pat. No. 9,255,275, which is a continuation of application No. 13/121,254, filed as application No. PCT/US2009/059039 on Sep. 30, 2009, now Pat. No. 8,647,856.

(60) Provisional application No. 61/101,250, filed on Sep. 30, 2008.

(51) Int. Cl.
| *C12N 15/80* | (2006.01) |
| *C12N 9/30* | (2006.01) |
| *C12N 9/58* | (2006.01) |
| *C12N 9/88* | (2006.01) |
| *C12P 21/02* | (2006.01) |
| *C12P 21/00* | (2006.01) |

(52) U.S. Cl.
CPC .......... *C12N 15/80* (2013.01); *C12N 9/242* (2013.01); *C12N 9/58* (2013.01); *C12N 9/88* (2013.01); *C12P 21/00* (2013.01); *C12P 21/02* (2013.01); *Y02P 20/52* (2015.11)

(58) Field of Classification Search
None
See application file for complete search history.

(56) References Cited

U.S. PATENT DOCUMENTS 8,647,856 B2    2/2014   Shasky

FOREIGN PATENT DOCUMENTS

| WO | 9812300 A1 | 3/1998 |
| WO | 9960137 A2 | 11/1999 |

OTHER PUBLICATIONS

Griffen et al., Microbiology, 1997, V. 143, pp. 3007-3013.
MacKenzie et al., Genetics Biotechnol., 2004, V. 15, pp. 289-315.
Royer et al., Biotechnology, 1995, V. 13, pp. 1479-1483.
Royer et al., Fungal Gen Biol., 1999, V. 28, pp. 68-78.

*Primary Examiner* — Antonio Galisteo Gonzalez
(74) *Attorney, Agent, or Firm* — Robert Starnes

(57) ABSTRACT

The present invention relates to methods of producing a polypeptide, comprising: (a) cultivating a mutant of a parent *Fusarium venenatum* strain in a medium for the production of the polypeptide, wherein the mutant strain comprises a polynucleotide encoding the polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions; and (b) recovering the polypeptide from the cultivation medium. The present invention also relates to enzyme-deficient mutants of *Fusarium venenatum* strains and methods for producing such mutants.

29 Claims, 35 Drawing Sheets

```
                        SEQUENCE LISTING

<160> NUMBER OF SEQ ID NOS: 102

<210> SEQ ID NO 1
<211> LENGTH: 1193
<212> TYPE: DNA
<213> ORGANISM: Neurospora crassa

<400> SEQUENCE: 1
atgtcgacaa gtaggaaacg cagccacact ggtccctcaa gcagtcgttt gctgagcggg      60
tagagagctc gacgcatccc ctcaccagct acctcttccg cctgatggag gtcaagcagt     120
ccaacctctg cctcagcgcc gatgtcgagc acgcgcggga tctcctcgcc cttgccgaca     180
aggtgggccc ctcgattgtc gtcctcaaga cccactacga cctgatcaca gggtgggact     240 accaccccgca cacgggcacc ggcgccaagc tggccgccct tgcccggaag cacggcttcc     300
tcatcttcga ggaccgcaag ttcgtcgaca ttggcagcac cgtccagaag cagtacacgg     360
ccggcaccgc gcgcattgtc gaatgggccc acatcaccaa cgccgacatc cacgccggag     420
aggccatggt gagcgccatg gcccaggccg cgcaaaagtg gagggagcgc atcccctacg     480
aggtcaagac gtcggtttcg gtgggcaccc cggtcgcgga ccagttcgcc gacgaggaag     540
ccgaggacca ggttgaggag ctgcgcaagg tcgtcacccg cgagaccagc accaccacaa     600
aggacacgga tgggaggaag agtagcatcg tctccatcac gaccgtcacg cagacatatg     660
agccggccga ctcgccacgt ctggtcaaga ccatctcgga ggacgatgag atggtgttcc     720
ccggcatcga ggaggcgcct ctggaccgcg gcctgctgat cttggcccag atgtcgtcca     780
```

```
agggctgcct catggacggc aagtacacat gggagtgtgt caaggcggcc cgcaagaaca   840
agggctttgt catgggctac gttgcgcagc agaacctgaa cggcattacc aaggaagctt   900
tggccccaag ctacgaagac ggcgaaagca cgacagagga agaagcgcaa gcagacaact   960
tcatccacat gacacccggc tgcaagttgc cgccaccagg agaggaagcg cctcagggcg  1020
acggactggg tcagcagtac aacacgccgg ataaccttgt caacatcaag ggcaccgata  1080
tcgcgattgt tgggcgtggc atcatcaccg cggcggatcc tccggccgag gctgagcgct  1140
acaggaggaa agcctggaag gcgtaccagg atcgccggga gcgtctggca tag         1193
```

<210> SEQ ID NO 2
<211> LENGTH: 397
<212> TYPE: PRT
<213> ORGANISM: Neurospora crassa

<400> SEQUENCE: 2

```
Met Ser Thr Ser Gln Glu Thr Gln Pro His Trp Ser Leu Lys Gln Ser
1               5                   10                  15

Phe Ala Glu Arg Val Glu Ser Ser Thr His Pro Leu Thr Ser Tyr Leu
            20                  25                  30

Phe Arg Leu Met Glu Val Lys Gln Ser Asn Leu Cys Leu Ser Ala Asp
        35                  40                  45

Val Glu His Ala Arg Asp Leu Leu Ala Leu Ala Asp Lys Val Gly Pro
    50                  55                  60

Ser Ile Val Val Leu Lys Thr His Tyr Asp Leu Ile Thr Gly Trp Asp
65                  70                  75                  80

Tyr His Pro His Thr Gly Thr Gly Ala Lys Leu Ala Ala Leu Ala Arg
                85                  90                  95

Lys His Gly Phe Leu Ile Phe Glu Asp Arg Lys Phe Val Asp Ile Gly
            100                 105                 110

Ser Thr Val Gln Lys Gln Tyr Thr Ala Gly Thr Ala Arg Ile Val Glu
        115                 120                 125

Trp Ala His Ile Thr Asn Ala Asp Ile His Ala Gly Glu Ala Met Val
    130                 135                 140

Ser Ala Met Ala Gln Ala Ala Gln Lys Trp Arg Glu Arg Ile Pro Tyr
145                 150                 155                 160

Glu Val Lys Thr Ser Val Ser Val Gly Thr Pro Val Ala Asp Gln Phe
                165                 170                 175

Ala Asp Glu Glu Ala Glu Asp Gln Val Glu Glu Leu Arg Lys Val Val
            180                 185                 190

Thr Arg Glu Thr Ser Thr Thr Thr Lys Asp Thr Asp Gly Arg Lys Ser
        195                 200                 205

Ser Ile Val Ser Ile Thr Thr Val Thr Gln Thr Tyr Glu Pro Ala Asp
    210                 215                 220

Ser Pro Arg Leu Val Lys Thr Ile Ser Glu Asp Asp Glu Met Val Phe
225                 230                 235                 240

Pro Gly Ile Glu Glu Ala Pro Leu Asp Arg Gly Leu Leu Ile Leu Ala
                245                 250                 255

Gln Met Ser Ser Lys Gly Cys Leu Met Asp Gly Lys Tyr Thr Trp Glu
            260                 265                 270

Cys Val Lys Ala Ala Arg Lys Asn Lys Gly Phe Val Met Gly Tyr Val
        275                 280                 285

Ala Gln Gln Asn Leu Asn Gly Ile Thr Lys Glu Ala Leu Ala Pro Ser
    290                 295                 300
```

```
Tyr Glu Asp Gly Glu Ser Thr Thr Glu Glu Ala Gln Ala Asp Asn
305                 310                 315                 320

Phe Ile His Met Thr Pro Gly Cys Lys Leu Pro Pro Gly Glu Glu
            325                 330                 335

Ala Pro Gln Gly Asp Gly Leu Gly Gln Gln Tyr Asn Thr Pro Asp Asn
                340                 345                 350

Leu Val Asn Ile Lys Gly Thr Asp Ile Ala Ile Val Gly Arg Gly Ile
            355                 360                 365

Ile Thr Ala Ala Asp Pro Pro Ala Glu Ala Glu Arg Tyr Arg Arg Lys
    370                 375                 380

Ala Trp Lys Ala Tyr Gln Asp Arg Arg Glu Arg Leu Ala
385                 390                 395

<210> SEQ ID NO 3
<211> LENGTH: 20
<212> TYPE: DNA
<213> ORGANISM: Neurospora crassa

<400> SEQUENCE: 3
gtcaggaaac gcagccacac                                                 20

<210> SEQ ID NO 4
<211> LENGTH: 20
<212> TYPE: DNA
<213> ORGANISM: Neurospora crassa

<400> SEQUENCE: 4
aggcagccct tggacgacat                                                 20

<210> SEQ ID NO 5
<211> LENGTH: 1026
<212> TYPE: DNA
<213> ORGANISM: Escherichia coli

<400> SEQUENCE: 5
atgaaaaagc tgaactcac cgcgacgtct gtcgagaagt ttctgatcga aaagttcgac       60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
``` gaatag    1026

<210> SEQ ID NO 6
<211> LENGTH: 343
<212> TYPE: PRT
<213> ORGANISM: Escherichia coli

<400> SEQUENCE: 6

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Arg Asn Ser Lys
            340

<210> SEQ ID NO 7

```
<211> LENGTH: 24
<212> TYPE: DNA
<213> ORGANISM: Escherichia coli

<400> SEQUENCE: 7
gggttcgaat tcatttaaac ggct                                          24

<210> SEQ ID NO 8
<211> LENGTH: 24
<212> TYPE: DNA
<213> ORGANISM: Escherichia coli

<400> SEQUENCE: 8
gggagcgctc aatattcatc tctc                                          24

<210> SEQ ID NO 9
<211> LENGTH: 31
<212> TYPE: DNA
<213> ORGANISM: Escherichia coli

<400> SEQUENCE: 9
gggtacccca agggcgtatt ctgcagatgg g                                  31

<210> SEQ ID NO 10
<211> LENGTH: 31
<212> TYPE: DNA
<213> ORGANISM: Escherichia coli

<400> SEQUENCE: 10
cccatctgca gaatacgccc ttggggtacc c                                  31

<210> SEQ ID NO 11
<211> LENGTH: 27
<212> TYPE: DNA
<213> ORGANISM: Escherichia coli

<400> SEQUENCE: 11
ggggtacctt catttaaacg gcttcac                                       27

<210> SEQ ID NO 12
<211> LENGTH: 25
<212> TYPE: DNA
<213> ORGANISM: Escherichia coli

<400> SEQUENCE: 12
ggggtacccg accagcagac ggccc                                         25

<210> SEQ ID NO 13
<211> LENGTH: 28
<212> TYPE: DNA
<213> ORGANISM: Aspergillus oryzae

<400> SEQUENCE: 13
tcccccgggt ctctggtact cttcgatc                                      28

<210> SEQ ID NO 14
<211> LENGTH: 25
<212> TYPE: DNA
<213> ORGANISM: Aspergillus oryzae

<400> SEQUENCE: 14
ggggtacccg accagcagac ggccc                                         25
```

<210> SEQ ID NO 15
<211> LENGTH: 27
<212> TYPE: DNA
<213> ORGANISM: Aspergillus oryzae

<400> SEQUENCE: 15
ggggtacctc tctggtactc ttcgatc                                      27

<210> SEQ ID NO 16
<211> LENGTH: 26
<212> TYPE: DNA
<213> ORGANISM: Aspergillus oryzae

<400> SEQUENCE: 16
tcccccgggc gaccagcaga cggccc                                       26

<210> SEQ ID NO 17
<211> LENGTH: 31
<212> TYPE: DNA
<213> ORGANISM: Aspergillus oryzae

<400> SEQUENCE: 17
gggtacccca agggcgtatt ctgcagatgg g                                 31

<210> SEQ ID NO 18
<211> LENGTH: 31
<212> TYPE: DNA
<213> ORGANISM: Aspergillus oryzae

<400> SEQUENCE: 18
cccatctgca gaatacgccc ttggggtacc c                                 31

<210> SEQ ID NO 19
<211> LENGTH: 1203
<212> TYPE: DNA
<213> ORGANISM: Fusarium venenatum

<400> SEQUENCE: 19
atggagaact ttcccactga gtattttctc aacacttctg tgcgccttct cgagtacatt    60
cgataccgag atagcaatta tacccgggaa gagcgtatcg agaatttgca ctatgcttac   120
aacaaggctg ctcatcactt tgctcagcca cgacaacagc agctgctcaa ggtagaccct   180
aagcgactac aggcttccct ccaaactatt gttggcatgg tggtatacag ttgggcaaag   240
gtctccaaag agtgtatggc ggatctatct attcattaca cgtacacact cgttttggat   300
gacagcagcg atgatccgta tccagccatg atgaactatt tcaacgatct tcaggctgga   360
cgagaacagg cccacccatg gtgggcgctt gttaatgagc actttcccaa tgtccttcga   420
cattttggtc ccttctgctc attgaacctt atccgcagca ctcttgactg taagtaccct   480
ggctctatta tttcaccgcc ttaataagct aacagtgatg gaattatagt ttttgaggga   540
tgctggatcg agcagtacaa ctttggagga tttccaggat ctcatgacta tcctcagttt   600
cttcgacgca tgaatggctt gggtcactgt gtcgggcctt ctttgtggcc caaagagcag   660
tttgatgaga gaggtctatt ccttgaaatc acatcagcca ttgctcagat ggagaactgg   720
atggtctggg tcaatgatct catgtctttc tacaaggagt cgatgatga gcgtgaccag   780
atcagtctcg tcaagaacta cgtcgtctct gatgagatca ctctccacga agctttagag   840
aagctcaccc aggacactct acactcgtcc aagcagatgg tagctgtctt ctctgacaag   900
gaccctcagg tgatggacac gattgagtgc ttcatgcacg gctatgtcac gtggcacttg   960

```
tgcgatcaca ggtaccgtct gaatgagatc tacgaaaagg tcaaaggaca aaagaccgag    1020
gacgctcaga agttctgcaa gttctatgag caggctgcta acgtcggagc cgtttcgccc    1080
tcggagtggg cttatccacc tattgcgcaa ctggcaaaca ttcggtccaa ggatgtgaag    1140
gatgtgaagg atgtgaagga gattcagaag cctctgctga gctcaattga gctagtggaa    1200
tga                                                                 1203
```

<210> SEQ ID NO 20
<211> LENGTH: 380
<212> TYPE: PRT
<213> ORGANISM: Fusarium venenatum

<400> SEQUENCE: 20

```
Met Glu Asn Phe Pro Thr Glu Tyr Phe Leu Asn Thr Ser Val Arg Leu
1               5                   10                  15

Leu Glu Tyr Ile Arg Tyr Arg Asp Ser Asn Tyr Thr Arg Glu Glu Arg
            20                  25                  30

Ile Glu Asn Leu His Tyr Ala Tyr Asn Lys Ala Ala His His Phe Ala
        35                  40                  45

Gln Pro Arg Gln Gln Leu Leu Lys Val Asp Pro Lys Arg Leu Gln
50                  55                  60

Ala Ser Leu Gln Thr Ile Val Gly Met Val Val Tyr Ser Trp Ala Lys
65                  70                  75                  80

Val Ser Lys Glu Cys Met Ala Asp Leu Ser Ile His Tyr Thr Tyr Thr
                85                  90                  95

Leu Val Leu Asp Asp Ser Ser Asp Pro Tyr Pro Ala Met Met Asn
            100                 105                 110

Tyr Phe Asn Asp Leu Gln Ala Gly Arg Glu Gln Ala His Pro Trp Trp
        115                 120                 125

Ala Leu Val Asn Glu His Phe Pro Asn Val Leu Arg His Phe Gly Pro
130                 135                 140

Phe Cys Ser Leu Asn Leu Ile Arg Ser Thr Leu Asp Phe Phe Glu Gly
145                 150                 155                 160

Cys Trp Ile Glu Gln Tyr Asn Phe Gly Gly Phe Pro Gly Ser His Asp
                165                 170                 175

Tyr Pro Gln Phe Leu Arg Arg Met Asn Gly Leu Gly His Cys Val Gly
            180                 185                 190

Ala Ser Leu Trp Pro Lys Glu Gln Phe Asp Glu Arg Gly Leu Phe Leu
        195                 200                 205

Glu Ile Thr Ser Ala Ile Ala Gln Met Glu Asn Trp Met Val Trp Val
210                 215                 220

Asn Asp Leu Met Ser Phe Tyr Lys Glu Phe Asp Asp Glu Arg Asp Gln
225                 230                 235                 240

Ile Ser Leu Val Lys Asn Tyr Val Val Ser Asp Glu Ile Thr Leu His
                245                 250                 255

Glu Ala Leu Glu Lys Leu Thr Gln Asp Thr Leu His Ser Ser Lys Gln
            260                 265                 270

Met Val Ala Val Phe Ser Asp Lys Asp Pro Gln Val Met Asp Thr Ile
        275                 280                 285

Glu Cys Phe Met His Gly Tyr Val Thr Trp His Leu Cys Asp His Arg
290                 295                 300

Tyr Arg Leu Asn Glu Ile Tyr Glu Lys Val Lys Gly Gln Lys Thr Glu
305                 310                 315                 320

Asp Ala Gln Lys Phe Cys Lys Phe Tyr Glu Gln Ala Ala Asn Val Gly
```

```
                      325                 330                 335
Ala Val Ser Pro Ser Glu Trp Ala Tyr Pro Pro Ile Ala Gln Leu Ala
        340                 345                 350

Asn Ile Arg Ser Lys Asp Val Lys Asp Val Lys Asp Val Lys Glu Ile
        355                 360                 365

Gln Lys Pro Leu Leu Ser Ser Ile Glu Leu Val Glu
        370                 375                 380

<210> SEQ ID NO 21
<211> LENGTH: 23
<212> TYPE: DNA
<213> ORGANISM: Fusarium venenatum

<400> SEQUENCE: 21
gggagatctt cgttatctgt gcc                                          23

<210> SEQ ID NO 22
<211> LENGTH: 29
<212> TYPE: DNA
<213> ORGANISM: Fusarium venenatum

<400> SEQUENCE: 22
gggagatctt agtagtcggc atttgaaac                                    29

<210> SEQ ID NO 23
<211> LENGTH: 43
<212> TYPE: DNA
<213> ORGANISM: Fusarium venenatum

<400> SEQUENCE: 23
caagtaacag acgcgacagc ttgcaaaatc ttcgttatct gtg                    43

<210> SEQ ID NO 24
<211> LENGTH: 43
<212> TYPE: DNA
<213> ORGANISM: Fusarium venenatum

<400> SEQUENCE: 24
cacagataac gaagattttg caagctgtcg cgtctgttac ttg                    43

<210> SEQ ID NO 25
<211> LENGTH: 60
<212> TYPE: DNA
<213> ORGANISM: Aspergillus nidulans

<400> SEQUENCE: 25
gacgaattct ctagaagatc tctcgaggag ctcaagcttc tgtacagtga ccggtgactc   60

<210> SEQ ID NO 26
<211> LENGTH: 27
<212> TYPE: DNA
<213> ORGANISM: Aspergillus nidulans

<400> SEQUENCE: 26
gacgaattcc gatgaatgtg tgtcctg                                      27

<210> SEQ ID NO 27
<211> LENGTH: 40
<212> TYPE: DNA
<213> ORGANISM: Escherichia coli

<400> SEQUENCE: 27
```
ttgaactctc agatcccttc atttaaacgg cttcacgggc                40

<210> SEQ ID NO 28
<211> LENGTH: 40
<212> TYPE: DNA
<213> ORGANISM: Escherichia coli

<400> SEQUENCE: 28
cagataacga agatctacgc ccttggggta cccaatattc                40

<210> SEQ ID NO 29
<211> LENGTH: 1131
<212> TYPE: DNA
<213> ORGANISM: Herpes simplex virus

<400> SEQUENCE: 29
atggcttcgt accccggcca tcaacacgcg tctgcgttcg accaggctgc gcgttctcgc     60
ggccatagca accgacgtac ggcgttgcgc cctcgccggc agcaagaagc cacggaagtc    120
cgcccggagc agaaaatgcc cacgctactg cgggtttata tagacggtcc ccacgggatg    180
gggaaaacca ccaccacgca actgctggtg ccctgggtt cgcgcgacga tatcgtctac    240
gtacccgagc cgatgactta ctggcgggtg ctggggggctt ccgagacaat cgcgaacatc    300
tacaccacac aacaccgcct cgaccagggt gagatatcgg ccggggacgc ggcggtggta    360
atgacaagcg cccagataac aatgggcatg ccttatgccg tgaccgacgc cgttctggct    420
cctcatatcg gggggaggc tgggagctca catgccccgc cccggccct cacctcatc    480
ttcgaccgcc atcccatcgc cgccctcctg tgctacccgg ccgcgcggta ccttatgggc    540
agcatgaccc ccaggccgt gctggcgttc gtggccctca tcccgccgac cttgccggc    600
accaacatcg tgcttggggc ccttccggag acagacaca tcgaccgcct ggccaaacgc    660
cagcgccccg gcgagcggct ggacctggct atgctggctg cgattcgccg cgtttacggg    720
ctacttgcca atacggtgcg gtatctgcag tgcggcgggt cgtggcggga ggactgggga    780
cagctttcgg ggacggccgt gccgccccag ggtgccgagc cccagagcaa cgcgggccca    840
cgaccccata tcggggacac gttatttacc ctgtttcggg ccccgagtt gctggccccc    900
aacggcgacc tgtataacgt gtttgcctgg gccttggacg tcttggccaa cgcctccgt    960
tccatgcacg tctttatcct ggattacgac caatcgcccg ccggctgccg ggacgccctg   1020
ctgcaactta cctccgggat ggtccagacc cacgtcacca cccccggctc cataccgacg   1080
atatgcgacc tggcgcgcac gtttgcccgg gagatggggg aggctaactg a            1131

<210> SEQ ID NO 30
<211> LENGTH: 376
<212> TYPE: PRT
<213> ORGANISM: Herpes simplex virus

<400> SEQUENCE: 30

Met Ala Ser Tyr Pro Gly His Gln His Ala Ser Ala Phe Asp Gln Ala
1               5                  10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr

```
             65                  70                  75                  80
        Val Pro Glu Pro Met Thr Tyr Trp Arg Val Leu Gly Ala Ser Glu Thr
                         85                  90                  95

Ile Ala Asn Ile Tyr Thr Thr Gln His Arg Leu Asp Gln Gly Glu Ile
                        100                 105                 110

Ser Ala Gly Asp Ala Ala Val Val Met Thr Ser Ala Gln Ile Thr Met
                        115                 120                 125

Gly Met Pro Tyr Ala Val Thr Asp Ala Val Leu Ala Pro His Ile Gly
            130                 135                 140

Gly Glu Ala Gly Ser Ser His Ala Pro Pro Ala Leu Thr Leu Ile
        145                 150                 155                 160

Phe Asp Arg His Pro Ile Ala Ala Leu Leu Cys Tyr Pro Ala Ala Arg
                            165                 170                 175

Tyr Leu Met Gly Ser Met Thr Pro Gln Ala Val Leu Ala Phe Val Ala
                        180                 185                 190

Leu Ile Pro Pro Thr Leu Pro Gly Thr Asn Ile Val Leu Gly Ala Leu
                        195                 200                 205

Pro Glu Asp Arg His Ile Asp Arg Leu Ala Lys Arg Gln Arg Pro Gly
            210                 215                 220

Glu Arg Leu Asp Leu Ala Met Leu Ala Ala Ile Arg Arg Val Tyr Gly
        225                 230                 235                 240

Leu Leu Ala Asn Thr Val Arg Tyr Leu Gln Cys Gly Gly Ser Trp Arg
                        245                 250                 255

Glu Asp Trp Gly Gln Leu Ser Gly Thr Ala Val Pro Pro Gln Gly Ala
                    260                 265                 270

Glu Pro Gln Ser Asn Ala Gly Pro Arg Pro His Ile Gly Asp Thr Leu
                    275                 280                 285

Phe Thr Leu Phe Arg Gly Pro Glu Leu Leu Ala Pro Asn Gly Asp Leu
            290                 295                 300

Tyr Asn Val Phe Ala Trp Ala Leu Asp Val Leu Ala Lys Arg Leu Arg
        305                 310                 315                 320

Ser Met His Val Phe Ile Leu Asp Tyr Asp Gln Ser Pro Ala Gly Cys
                        325                 330                 335

Arg Asp Ala Leu Leu Gln Leu Thr Ser Gly Met Val Gln Thr His Val
                    340                 345                 350

Thr Thr Pro Gly Ser Ile Pro Thr Ile Cys Asp Leu Ala Arg Thr Phe
                    355                 360                 365

Ala Arg Glu Met Gly Glu Ala Asn
            370                 375

<210> SEQ ID NO 31
<211> LENGTH: 40
<212> TYPE: DNA
<213> ORGANISM: Herpes simplex virus

<400> SEQUENCE: 31
gccgactact agatcgaccg gtgactcttt ctggcatgcg                          40

<210> SEQ ID NO 32
<211> LENGTH: 40
<212> TYPE: DNA
<213> ORGANISM: Herpes simplex virus

<400> SEQUENCE: 32
cagataacga agatctgaga gttcaaggaa gaaacagtgc                          40
```

<210> SEQ ID NO 33
<211> LENGTH: 27
<212> TYPE: DNA
<213> ORGANISM: Herpes simplex virus

<400> SEQUENCE: 33
ccctgtttcg gggccccgag ttgctgg                               27

<210> SEQ ID NO 34
<211> LENGTH: 27
<212> TYPE: DNA
<213> ORGANISM: Herpes simplex virus

<400> SEQUENCE: 34
ccagcaactc ggggccccga aacaggg                               27

<210> SEQ ID NO 35
<211> LENGTH: 29
<212> TYPE: DNA
<213> ORGANISM: Fusarium venenatum

<400> SEQUENCE: 35
gtgggaggat ctgatggatc accatgggc                             29

<210> SEQ ID NO 36
<211> LENGTH: 31
<212> TYPE: DNA
<213> ORGANISM: Fusarium venenatum

<400> SEQUENCE: 36
ccgggtttcg ttccgaacga tctttacaag g                          31

<210> SEQ ID NO 37
<211> LENGTH: 43
<212> TYPE: DNA
<213> ORGANISM: Fusarium venenatum

<400> SEQUENCE: 37
gtttaaacgg cgcgcccgac aaaacaaggc tactgcaggc agg             43

<210> SEQ ID NO 38
<211> LENGTH: 32
<212> TYPE: DNA
<213> ORGANISM: Fusarium venenatum

<400> SEQUENCE: 38
ttgtcgcccg ggaatactcc aactaggcct tg                         32

<210> SEQ ID NO 39
<211> LENGTH: 33
<212> TYPE: DNA
<213> ORGANISM: Fusarium venenatum

<400> SEQUENCE: 39
agtattcccg ggcgacaaaa caaggctact gca                        33

<210> SEQ ID NO 40
<211> LENGTH: 36
<212> TYPE: DNA
<213> ORGANISM: Fusarium venenatum

<400> SEQUENCE: 40
atttaaatcc tgcaggaata ctccaactag gccttg                     36

<210> SEQ ID NO 41
<211> LENGTH: 35
<212> TYPE: DNA
<213> ORGANISM: Escherichia coli

<400> SEQUENCE: 41
aaaacccggg ccttcattta aacggcttca cgggc                               35

<210> SEQ ID NO 42
<211> LENGTH: 40
<212> TYPE: DNA
<213> ORGANISM: Escherichia coli

<400> SEQUENCE: 42
aaaacccggg agatctacgc ccttggggta cccaatattc                          40

<210> SEQ ID NO 43
<211> LENGTH: 1098
<212> TYPE: DNA
<213> ORGANISM: Fusarium venenatum

<400> SEQUENCE: 43
atgtcgtcgc atccgtccct caaggcgact ttcgccagtc gagctgagac agcctctcat    60
cctcttagcc gacatctcta caaacttatg gacctcaagg cctcgaacct ttgtctcagc   120
gccgatgtcg caaccgcccg cgagctcctc tacttcgccg acaagatcgg ccctctatc   180
gtcgtcctca agactcatta tgacatggtg gctggctggg atttcgaccc ccgaacagga   240
accggtgcca agctcgcatc gctagcccgc aagcacggtt tcctcatctt tgaggatcgc   300
aagtttggtg acattggcaa cacggtcgag ctgcagtaca ccagtggtgc tgcccgcatt   360
atcgagtggg cacacattgt caatgtgaac atggtccctg aaaggcttc tgttacgtct    420
ttggctcacg ccgccaaccg atggctggag cgataccact atgaggtcaa gacatctatc   480
agcattggaa ccctacggc cagtcaacta gacgaggaca gcgagcgctc agatggcgag   540
aaccaaaaga gcgcacctga acttggccgc gacaacggac gcaaaggcag catcgtctct   600
accactaccg tcactcagca gtacgagtcg gccgattcac cacgcctcgt caagacgatc   660
cccgagggcg acgaaacagt attcgccggt atcgacgagg cacctatcga gagaggtctg   720
cttatcctag cacaaatgtc aagtgaaggc aacttcatga caaggaata cacacaagct   780
tgtgtagagg ccgcgcggga acacaagagc tttgttatgg gttcatttc acaggagtgt    840
ctcaacacac aacctgacga tgatttcatc cacatgaccc ctggctgcca attgcctcc    900
gagggtgcgg atgagaacga ggctatcaag ggagatggca agggtcagca atacaacaca   960
ccgcagaaga ttgttggtat tgcaggtgct gatattgcca ttgtcggacg tggaattatc  1020
aaggcgagtg accccgagga ggaggctgat cgatacccgat ccgcagcgtg aaggcttac  1080
acagaacgcg ttcgttga                                                1098

<210> SEQ ID NO 44
<211> LENGTH: 365
<212> TYPE: PRT
<213> ORGANISM: Fusarium venenatum

<400> SEQUENCE: 44

Met Ser Ser His Pro Ser Leu Lys Ala Thr Phe Ala Ser Arg Ala Glu
1               5                   10                  15

Thr Ala Ser His Pro Leu Ser Arg His Leu Tyr Lys Leu Met Asp Leu

```
                20                  25                  30
Lys Ala Ser Asn Leu Cys Leu Ser Ala Asp Val Ala Thr Ala Arg Glu
            35                  40                  45
Leu Leu Tyr Phe Ala Asp Lys Ile Gly Pro Ser Ile Val Val Leu Lys
        50                  55                  60
Thr His Tyr Asp Met Val Ala Gly Trp Asp Phe Asp Pro Arg Thr Gly
65                  70                  75                  80
Thr Gly Ala Lys Leu Ala Ser Leu Ala Arg Lys His Gly Phe Leu Ile
                85                  90                  95
Phe Glu Asp Arg Lys Phe Gly Asp Ile Gly Asn Thr Val Glu Leu Gln
            100                 105                 110
Tyr Thr Ser Gly Ala Ala Arg Ile Ile Glu Trp Ala His Ile Val Asn
        115                 120                 125
Val Asn Met Val Pro Gly Lys Ala Ser Val Thr Ser Leu Ala His Ala
130                 135                 140
Ala Asn Arg Trp Leu Glu Arg Tyr His Tyr Glu Val Lys Thr Ser Ile
145                 150                 155                 160
Ser Ile Gly Thr Pro Thr Ala Ser Gln Leu Asp Glu Asp Ser Glu Arg
                165                 170                 175
Ser Asp Gly Glu Asn Gln Lys Ser Ala Pro Glu Leu Gly Arg Asp Asn
            180                 185                 190
Gly Arg Lys Gly Ser Ile Val Ser Thr Thr Thr Val Thr Gln Gln Tyr
        195                 200                 205
Glu Ser Ala Asp Ser Pro Arg Leu Val Lys Thr Ile Pro Glu Gly Asp
210                 215                 220
Glu Thr Val Phe Ala Gly Ile Asp Glu Ala Pro Ile Glu Arg Gly Leu
225                 230                 235                 240
Leu Ile Leu Ala Gln Met Ser Ser Glu Gly Asn Phe Met Asn Lys Glu
                245                 250                 255
Tyr Thr Gln Ala Cys Val Glu Ala Ala Arg Glu His Lys Ser Phe Val
            260                 265                 270
Met Gly Phe Ile Ser Gln Glu Cys Leu Asn Thr Gln Pro Asp Asp Asp
        275                 280                 285
Phe Ile His Met Thr Pro Gly Cys Gln Leu Pro Pro Glu Gly Ala Asp
        290                 295                 300
Glu Asn Glu Ala Ile Lys Gly Asp Gly Lys Gly Gln Gln Tyr Asn Thr
305                 310                 315                 320
Pro Gln Lys Ile Val Gly Ile Ala Gly Ala Asp Ile Ala Ile Val Gly
                325                 330                 335
Arg Gly Ile Ile Lys Ala Ser Asp Pro Glu Glu Ala Asp Arg Tyr
            340                 345                 350
Arg Ser Ala Ala Trp Lys Ala Tyr Thr Glu Arg Val Arg
        355                 360                 365

<210> SEQ ID NO 45
<211> LENGTH: 39
<212> TYPE: DNA
<213> ORGANISM: Fusarium venenatum

<400> SEQUENCE: 45
aaaaaacctg caggatcctg cgcggactct tgattattt                    39

<210> SEQ ID NO 46
<211> LENGTH: 47
<212> TYPE: DNA
```

<213> ORGANISM: Fusarium venenatum

<400> SEQUENCE: 46
aaaaaacctg cagggcggcc gcaattccat tcctgtagct gagtata         47

<210> SEQ ID NO 47
<211> LENGTH: 46
<212> TYPE: DNA
<213> ORGANISM: Fusarium venenatum

<400> SEQUENCE: 47
aaaaaagttt aaacgcggcc gcctgttgcc tttgggccaa tcaatg          46

<210> SEQ ID NO 48
<211> LENGTH: 38
<212> TYPE: DNA
<213> ORGANISM: Fusarium venenatum

<400> SEQUENCE: 48
aaaaaagttt aaacctagtt ggagtattgt ttgttctt                   38

<210> SEQ ID NO 49
<211> LENGTH: 25
<212> TYPE: DNA
<213> ORGANISM: Fusarium venenatum

<400> SEQUENCE: 49
ggatcatcat gacagcgtcc gcaac                                 25

<210> SEQ ID NO 50
<211> LENGTH: 25
<212> TYPE: DNA
<213> ORGANISM: Fusarium venenatum

<400> SEQUENCE: 50
ggcatagaaa tctgcagcgc tctct                                 25

<210> SEQ ID NO 51
<211> LENGTH: 1555
<212> TYPE: DNA
<213> ORGANISM: Fusarium venenatum

<400> SEQUENCE: 51
atgaaacttc ttcaacttgc caccctggtg gcttccatca gcccattcgc cagcgcagca    60
gacgcaaacg cctggaagtc gcgaaacatt tattttgctc tcacagatcg tgttgcgcgt   120
agcggtagtg atagcggcgg taacgcctgc ggcaatctcg gaaactattg cggtggaacc   180
tttaagggtc ttgaggctaa gctcgactac atcaagggca tgggattcga cgccatctgg   240
atcactcctg ttgttgagag taagtatctt ggtcgtatat ctgtttggat gatgtctaac   300
cttttttgac agacacggat ggcggatacc acggatattg gccaaaaat ctttacgagg   360
tcaatgccaa gtacggaacc aaagacgacc tgaagagtct agtcaacact gcccatagca   420
aggtaagggg gacatgatcc tgcctgcact tcggccttta tctctgaaga aacttactga   480
ccgccccaga acatgtacgt catggctgac gtagtagcaa atcacatggg tccaggcatc   540
caaaaccaca gacccgaacc tctgaaccaa caaagttctt accactcttc ctgcgcaatc   600
gactacaaca accaaaacag tatcgagcag tgtgagatcg ctggcttgcc cgatctcaac   660
actggtagcg caacagtcaa gaaggttctc aacgactgga tctcatggct cgtctccgaa   720
tacagcttcg atggtatccg cattgacacc gtcaagcacg tcgaaaaggg cttctggcct   780

```
gatttccaga aggccgctgg agtcttctct atcggtgaag tctgggatgg aagccctgat    840
taccttgcag ggtactcaaa ggtcatgcct ggtctattga actacgccat ctactacccc    900
atgaaccgct tctaccagca gaagggtgac ccatccgcag tggttgatat gtacaacgag    960
atcagccaaa agtttgacga cccaactgtc ctgggtaagt aattatgaag atgaggtata   1020
aatgcattaa ctaagtcgtt acacaggaac attcatcgac aaccacgata tcctcgatg    1080
gttaagccaa agaacgacc aggccctcct caagaacgcc cttgcctacg ttattctctc    1140
tcgtggtatt cccattgtct attatggcac cgagcagggt tacgctggag caatgacccc   1200
cgcaaaccgt gaggatctct ggcgtagcaa cttcaagaca gactcagacc tttaccagac   1260
tatctccaag ctcggaaagg cccgctccgc tgttggtggt ctcgcaggaa acgaccagaa   1320
gttcctcaag tccaatgaca gtgcacttat ctggagccgt gccgatagcg atctaattgt   1380
tgtgactctg aatcgaggaa aaggattttc cggagagtac tgcttcaaca ctggcaagaa   1440
caacaagact tgggacagag tgctaggcca aggaactgtc aagtctgacg gtaacggcca   1500
gctatgtgtt agctacacta acggtgaacc cgaggttctc gttgcggcaa actaa        1555
```

<210> SEQ ID NO 52
<211> LENGTH: 460
<212> TYPE: PRT
<213> ORGANISM: Fusarium venenatum

<400> SEQUENCE: 52

```
Met Lys Leu Leu Gln Leu Ala Thr Leu Val Ala Ser Ile Ser Pro Phe
1               5                   10                  15

Ala Ser Ala Ala Asp Ala Asn Ala Trp Lys Ser Arg Asn Ile Tyr Phe
            20                  25                  30

Ala Leu Thr Asp Arg Val Ala Arg Ser Gly Ser Asp Ser Gly Gly Asn
        35                  40                  45

Ala Cys Gly Asn Leu Gly Asn Tyr Cys Gly Gly Thr Phe Lys Gly Leu
    50                  55                  60

Glu Ala Lys Leu Asp Tyr Ile Lys Gly Met Gly Phe Asp Ala Ile Trp
65                  70                  75                  80

Ile Thr Pro Val Val Glu Asn Thr Asp Gly Tyr His Gly Tyr Tyr Trp
                85                  90                  95

Ala Lys Asn Leu Tyr Glu Val Asn Ala Lys Tyr Gly Thr Lys Asp Asp
            100                 105                 110

Leu Lys Ser Leu Val Asn Thr Ala His Ser Lys Asn Met Tyr Val Met
        115                 120                 125

Ala Asp Val Val Ala Asn His Met Gly Pro Gly Ile Gln Asn His Arg
    130                 135                 140

Pro Glu Pro Leu Asn Gln Ser Ser Tyr His Ser Ser Cys Ala Ile
145                 150                 155                 160

Asp Tyr Asn Asn Gln Asn Ser Ile Glu Gln Cys Glu Ile Ala Gly Leu
                165                 170                 175

Pro Asp Leu Asn Thr Gly Ser Ala Thr Val Lys Lys Val Leu Asn Asp
            180                 185                 190

Trp Ile Ser Trp Leu Val Ser Glu Tyr Ser Phe Asp Gly Ile Arg Ile
        195                 200                 205

Asp Thr Val Lys His Val Glu Lys Gly Phe Trp Pro Asp Phe Gln Lys
    210                 215                 220

Ala Ala Gly Val Phe Ser Ile Gly Glu Val Trp Asp Gly Ser Pro Asp
225                 230                 235                 240
```

```
Tyr Leu Ala Gly Tyr Ser Lys Val Met Pro Gly Leu Leu Asn Tyr Ala
            245                 250                 255

Ile Tyr Tyr Pro Met Asn Arg Phe Tyr Gln Lys Gly Asp Pro Ser
        260                 265                 270

Ala Val Val Asp Met Tyr Asn Glu Ile Ser Gln Lys Phe Asp Pro
        275                 280                 285

Thr Val Leu Gly Thr Phe Ile Asp Asn His Asp Asn Pro Arg Trp Leu
        290                 295                 300

Ser Gln Lys Asn Asp Gln Ala Leu Leu Lys Asn Ala Leu Ala Tyr Val
305                 310                 315                 320

Ile Leu Ser Arg Gly Ile Pro Ile Val Tyr Tyr Gly Thr Glu Gln Gly
            325                 330                 335

Tyr Ala Gly Gly Asn Asp Pro Ala Asn Arg Glu Asp Leu Trp Arg Ser
            340                 345                 350

Asn Phe Lys Thr Asp Ser Asp Leu Tyr Gln Thr Ile Ser Lys Leu Gly
            355                 360                 365

Lys Ala Arg Ser Ala Val Gly Gly Leu Ala Gly Asn Asp Gln Lys Phe
    370                 375                 380

Leu Lys Ser Asn Asp Ser Ala Leu Ile Trp Ser Arg Ala Asp Ser Asp
385                 390                 395                 400

Leu Ile Val Val Thr Leu Asn Arg Gly Lys Gly Phe Ser Gly Glu Tyr
            405                 410                 415

Cys Phe Asn Thr Gly Lys Asn Asn Lys Thr Trp Asp Arg Val Leu Gly
            420                 425                 430

Pro Gly Thr Val Lys Ser Asp Gly Asn Gly Gln Leu Cys Val Ser Tyr
            435                 440                 445

Thr Asn Gly Gln Pro Glu Val Leu Val Ala Ala Asn
    450                 455                 460

<210> SEQ ID NO 53
<211> LENGTH: 30
<212> TYPE: DNA
<213> ORGANISM: Fusarium venenatum

<400> SEQUENCE: 53
gaggaattgg atttggatgt gtgtggaata                                30

<210> SEQ ID NO 54
<211> LENGTH: 28
<212> TYPE: DNA
<213> ORGANISM: Fusarium venenatum

<400> SEQUENCE: 54
ggagtctttg ttccaatgtg ctcgttga                                  28

<210> SEQ ID NO 55
<211> LENGTH: 27
<212> TYPE: DNA
<213> ORGANISM: Fusarium venenatum

<400> SEQUENCE: 55
ctacactaac ggtgaacccg aggttct                                   27

<210> SEQ ID NO 56
<211> LENGTH: 27
<212> TYPE: DNA
<213> ORGANISM: Fusarium venenatum
```

```
<400> SEQUENCE: 56
gcggcaaact aatgggtggt cgagttt                                           27

<210> SEQ ID NO 57
<211> LENGTH: 39
<212> TYPE: DNA
<213> ORGANISM: Fusarium venenatum

<400> SEQUENCE: 57
aaaaaacctg caggtaatgg gtggtcgagt ttaaaagta                              39

<210> SEQ ID NO 58
<211> LENGTH: 48
<212> TYPE: DNA
<213> ORGANISM: Fusarium venenatum

<400> SEQUENCE: 58
aaaaaacctg cagggcggcc gctttaagca tcatttttga ctacgcac                    48

<210> SEQ ID NO 59
<211> LENGTH: 52
<212> TYPE: DNA
<213> ORGANISM: Fusarium venenatum

<400> SEQUENCE: 59
aaaaaagttt aaacgcggcc gcttgattat gggatgaccc cagacaagtg gt               52

<210> SEQ ID NO 60
<211> LENGTH: 43
<212> TYPE: DNA
<213> ORGANISM: Fusarium venenatum

<400> SEQUENCE: 60
aaaaaagttt aaacccgcac gagcgtgttt ccttttcatc tcg                         43

<210> SEQ ID NO 61
<211> LENGTH: 25
<212> TYPE: DNA
<213> ORGANISM: Fusarium venenatum

<400> SEQUENCE: 61
ggatcatcat gacagcgtcc gcaac                                             25

<210> SEQ ID NO 62
<211> LENGTH: 25
<212> TYPE: DNA
<213> ORGANISM: Fusarium venenatum

<400> SEQUENCE: 62
ggcatagaaa tctgcagcgc tctct                                             25

<210> SEQ ID NO 63
<211> LENGTH: 1488
<212> TYPE: DNA
<213> ORGANISM: Microdochium nivale

<400> SEQUENCE: 63
atgcgttctg catttatctt ggccctcggc cttatcaccg ccagcgctga cgctttagtc       60
actcgcggtg ccatcgaggc ctgcctgtct gctgctggcg tcccgatcga tattcctggc      120
actgccgact atgagcgcga tgtcgagccc ttcaacatcc gcctgccata cattcccacc      180
gccattgctc agacgcagac tactgctcac atccagtcgg cagtccagtg cgccaagaag      240
```

-continued

```
ctcaacctca aggtctctgc caagtctggt ggtcacagct acgcctcgtt cggctttggt    300
ggcgagaacg tcacctcat ggtccagctc gaccgcatga ttgatgtcat ctcgtacaat     360
gacaagactg gcattgccca tgttgagccc ggtgcccgcc tcggacatct cgccaccgtc    420
ctcaacgaca agtacggccg tgccatctcc cacggtacat gccctggtgt cggcatctcc    480
ggccactttg cccacggcgg cttcggcttc agctcgcaca tgcacggtct ggctgtcgac    540
tcggtcgtcg tgtcactgt tgttcttgct gatggacgca tcgttgaggc ttctgccact    600
gagaatgctg acctcttctg gggtatcaag ggcgctggct ccaacttcgg catcgttgct    660
gtctggaagc tcgccacttt ccctgctccc aaggttctca cccgctttgg cgtcaccctc    720
aactggaaga caagacctc tgccctcaag ggcatcgagg ctgttgagga ctacgcccgc    780
tgggtcgccc ccgcgaggt caacttccgc attggagact acggcgctgg taacccgggt    840
atcgagggtc tctactacgg cactcccgag caatggcgtg cggctttcca acctctgctc    900
gacactctgc ctgctggata cgttgtcaac ccgaccacct ccttgaactg gatcgagtcg    960
gtgctcagct actccaactt tgaccatgtc gacttcatta ctcctcagcc tgtcgagaac   1020
ttctatgcca agagcttgac gctcaagagt atcaagggcg acgccgtcaa gaactttgtc   1080
gactactact ttgacgtgtc caacaaggtt aaggaccgct tctggttcta ccagctcgac   1140
gtgcacggcg gcaagaactc gcaagtcacc aaggtcacca cgccgagac agcctaccct   1200 caccgcgaca agctctggct gatccagttc tacgaccgct acgacaacaa ccagacctac   1260
ccggagacct cattcaagtt cctcgacggc tgggtcaact cggtcaccaa ggctctcccc   1320
aagtccgact ggggcatgta catcaactac gccgaccccc gcatggaccg cgactacgcc   1380
accaaggtct actacggtga gaacctcgcc aggctccaga agctcaaggc caagtttgat   1440
cccaccgacc gtttctacta ccctcaggct gtccgccctg tcaaataa                1488
```

<210> SEQ ID NO 64
<211> LENGTH: 495
<212> TYPE: PRT
<213> ORGANISM: Microdochium nivale

<400> SEQUENCE: 64

```
Met Arg Ser Ala Phe Ile Leu Ala Leu Gly Leu Ile Thr Ala Ser Ala
1               5                   10                  15

Asp Ala Leu Val Thr Arg Gly Ala Ile Glu Ala Cys Leu Ser Ala Ala
            20                  25                  30

Gly Val Pro Ile Asp Ile Pro Gly Thr Ala Asp Tyr Glu Arg Asp Val
        35                  40                  45

Glu Pro Phe Asn Ile Arg Leu Pro Tyr Ile Pro Thr Ala Ile Ala Gln
    50                  55                  60

Thr Gln Thr Thr Ala His Ile Gln Ser Ala Val Gln Cys Ala Lys Lys
65                  70                  75                  80

Leu Asn Leu Lys Val Ser Ala Lys Ser Gly Gly His Ser Tyr Ala Ser
                85                  90                  95

Phe Gly Phe Gly Gly Glu Asn Gly His Leu Met Val Gln Leu Asp Arg
            100                 105                 110

Met Ile Asp Val Ile Ser Tyr Asn Asp Lys Thr Gly Ile Ala His Val
        115                 120                 125

Glu Pro Gly Ala Arg Leu Gly His Leu Ala Thr Val Leu Asn Asp Lys
    130                 135                 140

Tyr Gly Arg Ala Ile Ser His Gly Thr Cys Pro Gly Val Gly Ile Ser
```

```
            145                 150                 155                 160
        Gly His Phe Ala His Gly Phe Gly Phe Ser Ser His Met His Gly
                            165                 170                 175

Leu Ala Val Asp Ser Val Val Gly Val Thr Val Val Leu Ala Asp Gly
                        180                 185                 190

Arg Ile Val Glu Ala Ser Ala Thr Glu Asn Ala Asp Leu Phe Trp Gly
                    195                 200                 205

Ile Lys Gly Ala Gly Ser Asn Phe Gly Ile Val Ala Val Trp Lys Leu
                210                 215                 220

Ala Thr Phe Pro Ala Pro Lys Val Leu Thr Arg Phe Gly Val Thr Leu
        225                 230                 235                 240

Asn Trp Lys Asn Lys Thr Ser Ala Leu Lys Gly Ile Glu Ala Val Glu
                        245                 250                 255

Asp Tyr Ala Arg Trp Val Ala Pro Arg Glu Val Asn Phe Arg Ile Gly
                    260                 265                 270

Asp Tyr Gly Ala Gly Asn Pro Gly Ile Glu Gly Leu Tyr Tyr Gly Thr
                275                 280                 285

Pro Glu Gln Trp Arg Ala Ala Phe Gln Pro Leu Leu Asp Thr Leu Pro
            290                 295                 300

Ala Gly Tyr Val Val Asn Pro Thr Thr Ser Leu Asn Trp Ile Glu Ser
        305                 310                 315                 320

Val Leu Ser Tyr Ser Asn Phe Asp His Val Asp Phe Ile Thr Pro Gln
                        325                 330                 335

Pro Val Glu Asn Phe Tyr Ala Lys Ser Leu Thr Leu Lys Ser Ile Lys
                    340                 345                 350

Gly Asp Ala Val Lys Asn Phe Val Asp Tyr Tyr Phe Asp Val Ser Asn
                355                 360                 365

Lys Val Lys Asp Arg Phe Trp Phe Tyr Gln Leu Asp Val His Gly Gly
            370                 375                 380

Lys Asn Ser Gln Val Thr Lys Val Thr Asn Ala Glu Thr Ala Tyr Pro
        385                 390                 395                 400

His Arg Asp Lys Leu Trp Leu Ile Gln Phe Tyr Asp Arg Tyr Asp Asn
                        405                 410                 415

Asn Gln Thr Tyr Pro Glu Thr Ser Phe Lys Phe Leu Asp Gly Trp Val
                    420                 425                 430

Asn Ser Val Thr Lys Ala Leu Pro Lys Ser Asp Trp Gly Met Tyr Ile
                435                 440                 445

Asn Tyr Ala Asp Pro Arg Met Asp Arg Asp Tyr Ala Thr Lys Val Tyr
            450                 455                 460

Tyr Gly Glu Asn Leu Ala Arg Leu Gln Lys Leu Lys Ala Lys Phe Asp
        465                 470                 475                 480

Pro Thr Asp Arg Phe Tyr Tyr Pro Gln Ala Val Arg Pro Val Lys
                        485                 490                 495

<210> SEQ ID NO 65
<211> LENGTH: 26
<212> TYPE: DNA
<213> ORGANISM: Microdochium nivale

<400> SEQUENCE: 65
cccgcatgcg ttctgcattt atcttg                                        26

<210> SEQ ID NO 66
<211> LENGTH: 26
<212> TYPE: DNA
```

<213> ORGANISM: Microdochium nivale

<400> SEQUENCE: 66

| gggttaatta attatttgac agggcg | 26 |

<210> SEQ ID NO 67
<211> LENGTH: 1389
<212> TYPE: DNA
<213> ORGANISM: Candida antarctica

<400> SEQUENCE: 67

| atgcgagtgt ccttgcgctc catcacgtcg ctgcttgcgg cggcaacggc ggctgtgctc | 60 |
| gcggctccgg cggccgagac gctggaccga cgggcggcgc tgcccaaccc ctacgacgat | 120 |
| cccttctaca cgacgccatc caacatcggc acgtttgcca agggccaggt gatccaatct | 180 |
| cgcaaggtgc ccacggacat cggcaacgcc aacaacgctg cgtcgttcca gctgcagtac | 240 |
| cgcaccacca atacgcagaa cgaggcggtg gccgacgtgg ccaccgtgtg gatcccggcc | 300 |
| aagcccgctt cgccgcccaa gatcttttcg taccaggtct acgaggatgc cacggcgctc | 360 |
| gactgtgctc cgagctacag ctacctcact ggattggacc agccgaacaa ggtgacggcg | 420 |
| gtgctcgaca cgcccatcat catcggctgg gcgctgcagc agggctacta cgtcgtctcg | 480 |
| tccgaccacg aaggcttcaa agccgccttc atcgctggct acgaagaggg catggctatc | 540 |
| ctcgacggca tccgcgcgct caagaactac cagaacctgc catccgacag caaggtcgct | 600 |
| cttgagggct acagtggcgg agctcacgcc accgtgtggg cgacttcgct tgctgaatcg | 660 |
| tacgcgcccg agctcaacat tgtcggtgct tcgcacggcg gcacgcccgt gagcgccaag | 720 |
| gacaccttta cattcctcaa cggcggaccc ttcgccggct ttgccctggc gggtgtttcg | 780 |
| ggtctctcgc tcgctcatcc tgatatggag agcttcattg aggcccgatt gaacgccaag | 840 |
| ggtcagcgga cgctcaagca gatccgcggc cgtggcttct gcctgccgca ggtggtgttg | 900 |
| acctaccccct cctcaacgt cttctcgctg gtcaacgaca cgaacctgct gaatgaggcg | 960 |
| ccgatcgcta gcatcctcaa gcaggagact gtggtccagg ccgaagcgag ctacacggta | 1020 |
| tcggtgccca gttcccgcg cttcatctgg catgcgatcc ccgacgagat cgtgccgtac | 1080 |
| cagcctgcgg ctacctacgt caaggagcaa tgtgccaagg gcgccaacat caatttttcg | 1140 |
| ccctacccga tcgccgagca cctcaccgcc gagatctttg gtctggtgcc tagcctgtgg | 1200 |
| tttatcaagc aagccttcga cggcaccaca cccaaggtga tctgcggcac tcccatccct | 1260 |
| gctatcgctg gcatcaccac gccctcggcg gaccaagtgc tgggttcgga cctggccaac | 1320 |
| cagctgcgca gcctcgacgg caagcagagt gcgttcggca agccctttgg ccccatcaca | 1380 |
| ccaccttag | 1389 |

<210> SEQ ID NO 68
<211> LENGTH: 462
<212> TYPE: PRT
<213> ORGANISM: Candida antarctica

<400> SEQUENCE: 68

Met Arg Val Ser Leu Arg Ser Ile Thr Ser Leu Leu Ala Ala Ala Thr
1               5                   10                  15

Ala Ala Val Leu Ala Ala Pro Ala Ala Glu Thr Leu Asp Arg Arg Ala
            20                  25                  30

Ala Leu Pro Asn Pro Tyr Asp Asp Pro Phe Tyr Thr Thr Pro Ser Asn
        35                  40                  45

```
Ile Gly Thr Phe Ala Lys Gly Gln Val Ile Gln Ser Arg Lys Val Pro
 50                  55                  60

Thr Asp Ile Gly Asn Ala Asn Asn Ala Ala Ser Phe Gln Leu Gln Tyr
 65                  70                  75                  80

Arg Thr Thr Asn Thr Gln Asn Glu Ala Val Ala Asp Val Ala Thr Val
                 85                  90                  95

Trp Ile Pro Ala Lys Pro Ala Ser Pro Lys Ile Phe Ser Tyr Gln
                100                 105                 110

Val Tyr Glu Asp Ala Thr Ala Leu Asp Cys Ala Pro Ser Tyr Ser Tyr
            115                 120                 125

Leu Thr Gly Leu Asp Gln Pro Asn Lys Val Thr Ala Val Leu Asp Thr
        130                 135                 140

Pro Ile Ile Gly Trp Ala Leu Gln Gln Gly Tyr Tyr Val Val Ser
145                 150                 155                 160

Ser Asp His Glu Gly Phe Lys Ala Ala Phe Ile Ala Gly Tyr Glu Glu
                165                 170                 175

Gly Met Ala Ile Leu Asp Gly Ile Arg Ala Leu Lys Asn Tyr Gln Asn
            180                 185                 190

Leu Pro Ser Asp Ser Lys Val Ala Leu Glu Gly Tyr Ser Gly Gly Ala
        195                 200                 205

His Ala Thr Val Trp Ala Thr Ser Leu Ala Glu Ser Tyr Ala Pro Glu
    210                 215                 220

Leu Asn Ile Val Gly Ala Ser His Gly Gly Thr Pro Val Ser Ala Lys
225                 230                 235                 240

Asp Thr Phe Thr Phe Leu Asn Gly Gly Pro Phe Ala Gly Phe Ala Leu
                245                 250                 255

Ala Gly Val Ser Gly Leu Ser Leu Ala His Pro Asp Met Glu Ser Phe
            260                 265                 270

Ile Glu Ala Arg Leu Asn Ala Lys Gly Gln Arg Thr Leu Lys Gln Ile
        275                 280                 285

Arg Gly Arg Gly Phe Cys Leu Pro Gln Val Val Leu Thr Tyr Pro Phe
    290                 295                 300

Leu Asn Val Phe Ser Leu Val Asn Asp Thr Asn Leu Leu Asn Glu Ala
305                 310                 315                 320

Pro Ile Ala Ser Ile Leu Lys Gln Glu Thr Val Val Gln Ala Glu Ala
                325                 330                 335

Ser Tyr Thr Val Ser Val Pro Lys Phe Pro Arg Phe Ile Trp His Ala
            340                 345                 350

Ile Pro Asp Glu Ile Val Pro Tyr Gln Pro Ala Ala Thr Tyr Val Lys
        355                 360                 365

Glu Gln Cys Ala Lys Gly Ala Asn Ile Asn Phe Ser Pro Tyr Pro Ile
    370                 375                 380

Ala Glu His Leu Thr Ala Glu Ile Phe Gly Leu Val Pro Ser Leu Trp
385                 390                 395                 400

Phe Ile Lys Gln Ala Phe Asp Gly Thr Thr Pro Lys Val Ile Cys Gly
                405                 410                 415

Thr Pro Ile Pro Ala Ile Ala Gly Ile Thr Thr Pro Ser Ala Asp Gln
            420                 425                 430

Val Leu Gly Ser Asp Leu Ala Asn Gln Leu Arg Ser Leu Asp Gly Lys
        435                 440                 445

Gln Ser Ala Phe Gly Lys Pro Phe Gly Pro Ile Thr Pro Pro
450                 455                 460
```

```
<210> SEQ ID NO 69
<211> LENGTH: 20
<212> TYPE: DNA
<213> ORGANISM: Candida antarctica

<400> SEQUENCE: 69
gcatgcgagt gtccttgcgc                                               20

<210> SEQ ID NO 70
<211> LENGTH: 24
<212> TYPE: DNA
<213> ORGANISM: Candida antarctica

<400> SEQUENCE: 70
ttaattaact aaggtggtgt gatg                                          24

<210> SEQ ID NO 71
<211> LENGTH: 31
<212> TYPE: DNA
<213> ORGANISM: Fusarium oxysporum

<400> SEQUENCE: 71
tcagatttaa atatgcttct tctaccactc c                                  31

<210> SEQ ID NO 72
<211> LENGTH: 28
<212> TYPE: DNA
<213> ORGANISM: Fusarium oxysporum

<400> SEQUENCE: 72
agtcttaatt aaagctagtg aatgaaat                                      28

<210> SEQ ID NO 73
<211> LENGTH: 27
<212> TYPE: DNA
<213> ORGANISM: Fusarium venenatum

<400> SEQUENCE: 73
gcaggaaaga acaagtgagc aaaaggc                                       27

<210> SEQ ID NO 74
<211> LENGTH: 27
<212> TYPE: DNA
<213> ORGANISM: Fusarium venenatum

<400> SEQUENCE: 74 gcctttgct cacttgttct ttcctgc                                        27

<210> SEQ ID NO 75
<211> LENGTH: 15
<212> TYPE: DNA
<213> ORGANISM: Fusarium oxysporum

<400> SEQUENCE: 75
dcctacatgt ttaat                                                    15

<210> SEQ ID NO 76
<211> LENGTH: 13
<212> TYPE: DNA
<213> ORGANISM: Fusarium oxysporum

<400> SEQUENCE: 76
dtaaacatgt agg                                                      13
```

<210> SEQ ID NO 77
<211> LENGTH: 25
<212> TYPE: DNA
<213> ORGANISM: Fusarium oxysporum

<400> SEQUENCE: 77
gggggcatgc ttcttctacc actcc                                              25

<210> SEQ ID NO 78
<211> LENGTH: 27
<212> TYPE: DNA
<213> ORGANISM: Fusarium oxysporum

<400> SEQUENCE: 78
ggggttaatt aagagcgggc ctggtta                                            27

<210> SEQ ID NO 79
<211> LENGTH: 45
<212> TYPE: DNA
<213> ORGANISM: Fusarium venenatum

<400> SEQUENCE: 79
cctgcatggc cgccgccgcc aattcttaca aaccttcaac agtgg                        45

<210> SEQ ID NO 80
<211> LENGTH: 45
<212> TYPE: DNA
<213> ORGANISM: Fusarium venenatum

<400> SEQUENCE: 80
ccactgttga aggtttgtaa gaattggcgg cggcggccat gcagg                        45

<210> SEQ ID NO 81
<211> LENGTH: 35
<212> TYPE: DNA
<213> ORGANISM: Fusarium venenatum

<400> SEQUENCE: 81
ataagaatgc ggccgctcca aggaatagaa tcact                                   35

<210> SEQ ID NO 82
<211> LENGTH: 25
<212> TYPE: DNA
<213> ORGANISM: Fusarium venenatum

<400> SEQUENCE: 82
cggaattctg tcgtcgaata ctaac                                              25

<210> SEQ ID NO 83
<211> LENGTH: 1289
<212> TYPE: DNA
<213> ORGANISM: Fusarium venenatum

<400> SEQUENCE: 83
atgaccagct tccgccgtct cgctctctgc cttggagctc tgctccctgc agtcctcgcc        60
gctcccactg agaagcgaca ggaactcact gccgcacctg acaagtacat catcactctc       120
aagcccgagg cttctgagac caaggttgag gctcacttga actgggtcag cgatgttcac       180
cgtcgcagcc ttaacaagcg tgataccctct ggtgtcgaga agaagttcaa catcagcacc       240
tggaacgcct actctggcga gttcgacaag gctaccattg atgagatcaa gaagagcccc       300
gaggttgctt tcgtcgagcc tgactacact gtctacctcg actacgagac cgagctgtct       360

```
gaccgtgcct tgactaccca gagtggtgct ccttggggtc ttgcctccat ctcccgccga      420
acctccggtg gcagcactta cacctacgac accactgccg gctccggtgc ttacggttac      480
gtcgttgaca gcggcatcaa cgtcgaccac cgagatttcg gtggccgtgc ttctctcggc      540
ttcaacgctg ccggtggtgc tcacgtcgac acccttggcc acggtaccca cgtcgctgga      600
accattgctt ctgccaccta cggtgttgcc aagcgcgtaa gtaaacccca caatttatgg      660
tagcatctga actttatact tactatcttt aggccaacgt catctctgtc aaggtcttca      720
ccggtaacag tggttccacc tccactatcc tctctggttt caactgggct gtcaacgaca      780
tcacctccaa gggacgcacc ggccgctctg tcatcaacct gtctctcggt ggtcccgctt      840
ctcagacctg gaccactgct atcaacgctg cttacaactc tggtgttctc tccgttgttg      900
ctgccggtaa cggtgacgat tcggccgcc ctcttcccgt ctctggccag tctcctgcca      960
acgtccccaa cgctctgacc gttgctgcca ttgactccag ctggcgcact gcctctttca      1020
ccaactacgg tgccggtgtt gatgtcttcg ccctggtgtc agcatcctct cactggattg      1080
gttccacctc tgctaccaac tccatcagcg gtacctccat ggcctgccct cacgttgctg      1140
gtcttgctct ctacctccag gttctcgagg gtctttccac ccctgctgct gttaccaacc      1200
gcatcaaggc tcttgctacc actggccgtg tcactggcac cctgagcggt agccccaacc      1260
tgatcgcctt caacggtgct tccgcttaa                                        1289

<210> SEQ ID NO 84
<211> LENGTH: 410
<212> TYPE: PRT
<213> ORGANISM: Fusarium venenatum

<400> SEQUENCE: 84

Met Thr Ser Phe Arg Arg Leu Ala Leu Cys Leu Gly Ala Leu Leu Pro
1               5                   10                  15

Ala Val Leu Ala Ala Pro Thr Glu Lys Arg Gln Glu Leu Thr Ala Ala
            20                  25                  30

Pro Asp Lys Tyr Ile Ile Thr Leu Lys Pro Glu Ala Ser Glu Thr Lys
        35                  40                  45

Val Glu Ala His Leu Asn Trp Val Ser Asp Val His Arg Arg Ser Leu
    50                  55                  60

Asn Lys Arg Asp Thr Ser Gly Val Glu Lys Lys Phe Asn Ile Ser Thr
65                  70                  75                  80

Trp Asn Ala Tyr Ser Gly Glu Phe Asp Lys Ala Thr Ile Asp Glu Ile
                85                  90                  95

Lys Lys Ser Pro Glu Val Ala Phe Val Glu Pro Asp Tyr Thr Val Tyr
            100                 105                 110

Leu Asp Tyr Glu Thr Glu Leu Ser Asp Arg Ala Leu Thr Thr Gln Ser
        115                 120                 125

Gly Ala Pro Trp Gly Leu Ala Ser Ile Ser Arg Thr Ser Gly Gly
    130                 135                 140

Ser Thr Tyr Thr Tyr Asp Thr Thr Ala Gly Ser Gly Ala Tyr Gly Tyr
145                 150                 155                 160

Val Val Asp Ser Gly Ile Asn Val Asp His Arg Asp Phe Gly Gly Arg
                165                 170                 175

Ala Ser Leu Gly Phe Asn Ala Ala Gly Gly Ala His Val Asp Thr Leu
            180                 185                 190

Gly His Gly Thr His Val Ala Gly Thr Ile Ala Ser Ala Thr Tyr Gly
        195                 200                 205
```

-continued

```
Val Ala Lys Arg Ala Asn Val Ile Ser Val Lys Val Phe Thr Gly Asn
        210                 215                 220
Ser Gly Ser Thr Ser Thr Ile Leu Ser Gly Phe Asn Trp Ala Val Asn
225                 230                 235                 240
Asp Ile Thr Ser Lys Gly Arg Thr Gly Arg Ser Val Ile Asn Leu Ser
                245                 250                 255
Leu Gly Gly Pro Ala Ser Gln Thr Trp Thr Thr Ala Ile Asn Ala Ala
                260                 265                 270
Tyr Asn Ser Gly Val Leu Ser Val Ala Ala Gly Asn Gly Asp Asp
                275                 280                 285
Phe Gly Arg Pro Leu Pro Val Ser Gly Gln Ser Pro Ala Asn Val Pro
        290                 295                 300
Asn Ala Leu Thr Val Ala Ala Ile Asp Ser Ser Trp Arg Thr Ala Ser
305                 310                 315                 320
Phe Thr Asn Tyr Gly Ala Gly Val Asp Val Phe Ala Leu Val Ser Ala
                325                 330                 335
Ser Ser His Trp Ile Gly Ser Thr Ala Thr Asn Ser Ile Ser Gly
                340                 345                 350
Thr Ser Met Ala Cys Pro His Val Ala Gly Leu Ala Leu Tyr Leu Gln
                355                 360                 365
Val Leu Glu Gly Leu Ser Thr Pro Ala Ala Val Thr Asn Arg Ile Lys
        370                 375                 380
Ala Leu Ala Thr Thr Gly Arg Val Thr Gly Thr Leu Ser Gly Ser Pro
385                 390                 395                 400
Asn Leu Ile Ala Phe Asn Gly Ala Ser Ala
                405                 410

<210> SEQ ID NO 85
<211> LENGTH: 30
<212> TYPE: DNA
<213> ORGANISM: Fusarium venenatum

<400> SEQUENCE: 85
gaggaattgg atttggatgt gtgtggaata                                      30

<210> SEQ ID NO 86
<211> LENGTH: 28
<212> TYPE: DNA
<213> ORGANISM: Fusarium venenatum

<400> SEQUENCE: 86
ggagtctttg ttccaatgtg ctcgttga                                        28

<210> SEQ ID NO 87
<211> LENGTH: 48
<212> TYPE: DNA
<213> ORGANISM: Fusarium venenatum

<400> SEQUENCE: 87
aaaaaaggcg cgccgcggcc gcgttacggt gttcaagtac atcttaca                  48

<210> SEQ ID NO 88
<211> LENGTH: 39
<212> TYPE: DNA
<213> ORGANISM: Fusarium venenatum

<400> SEQUENCE: 88
aaaaaaggcg cgccattgct atcatcaact gcctttctt                            39
```

<210> SEQ ID NO 89
<211> LENGTH: 36
<212> TYPE: DNA
<213> ORGANISM: Fusarium venenatum

<400> SEQUENCE: 89
aaaaacctgc aggggatgtg tgtggaatag gatatg                                36

<210> SEQ ID NO 90
<211> LENGTH: 45
<212> TYPE: DNA
<213> ORGANISM: Fusarium venenatum

<400> SEQUENCE: 90
aaaaacctgc agggcggccg ccctcaaggt ggagaaataa tctgt                      45

<210> SEQ ID NO 91
<211> LENGTH: 25
<212> TYPE: DNA
<213> ORGANISM: Fusarium venenatum

<400> SEQUENCE: 91
gcacgttagg ctcaagccag caagg                                            25

<210> SEQ ID NO 92
<211> LENGTH: 25
<212> TYPE: DNA
<213> ORGANISM: Fusarium venenatum

<400> SEQUENCE: 92
gaggctcatg gatgtggcgt taatg                                            25

<210> SEQ ID NO 93
<211> LENGTH: 9390
<212> TYPE: DNA
<213> ORGANISM: Fusarium venenatum

<400> SEQUENCE: 93
atggaatatc ttactgctgt cgatggtagg caagacctgc cacctacacc agcttcgttt      60
tgtagtcatg gagatagtcc cctcaatagc tcttacgagc aactcttcca tctctatggt     120
ctggattcga gtcgcatcga agctatcaaa ccatgcacac ctttccagct tgacatgatc     180
gactgcaatg ctttggataa gcagtctgct atcggccatg cggtgtatga tgtcccaacc     240
gacattgaca tctctcgttt cgcgcttgcg tggaaggaga tcgtcaacca aaccccagcc     300
ttgcgagcct ttgccttcac ctcggactct ggaaagactt ctcaagtcat cctaaaagat     360
agctttgtct tctcatggat gtgctggtct tcttcgagct ccccagatga agtggttcgg     420
gatgaagctg ccgctgctgc atccgggcca cgctgcaacc gcttcgttct acttgaagac     480
atgcagacga agaaatgtca gctggtttgg accttcagtc atgcattggt agacgtcact     540
ttccaacaac gcgtcctgag ccgtgttttc gcggcttaca agcatgagaa ggacacacat     600
cggcctgaga cacccgagtc atctgatgcc actgacactg actctcagtc agtctccgtg     660
gtgtccatga gctgcgagga caatgccgta tcggcgactc atttctggca aactcacctt     720
aacgatctca atgcgtccgt cttccctcac ctgtctgacc acctgatggt gcccaaccca     780
actacaacag cagagcatcg tatcacattc cctctttcac agaaagcact atccaattct     840
gccatctgcc gtactgcact ctcaatactc ctctcgcgct acactcactc tgacgaggcc     900

```
ttgtttggtg cggtaactga gcaatctcta ccatttgaca acactatct tgcagatggt      960
acgtaccaaa cagttgcacc ccttcgtgta cactgccaat caaatcttcg tgcatcagat    1020
gtcatggatg caatctcttc ttacgatgat cgccttggtc atctcgcccc atttggcctt    1080
cgcgacatcc gcaacactgg tgataatggc tctgccgcct gcgatttcca aactgtttta    1140
ctcgtcaccg atggcagcca cgtaaacaat ggtatcaacg gtttcctcca acagataaca    1200
gagtcaagcc atttcatgcc ttgcaacaac cgtgccctcc ttctgcactg tcagatggaa    1260
agtagcggag ctctgctggt tgcctactat gaccacaatg ttatcgattc gcttcagaca    1320
acgcgtctgc tacagcagtt tggtcatctg atcaagtgtt tgcaaagtcc tctagacctg    1380
agctctatgg ctgaggtcaa cttgatgact gagtatgaca gagcagagat tgagagttgg    1440
aactcgcaac cgttagaggt acaggatacc ctgatccacc atgagatgtt gaaagctgtt    1500
tctcattccc ccaccaaaac ggccatccaa gcgtgggatg gagactggac ctattccgag    1560
ctcgacaatg tttcgtcaag actcgctgtc catatcaagt cacttggcct tagagctcag    1620
caagccatta ttccagtcta cttttgagaag tcgaaatggg tcattgcttc aatgctggct    1680
gttctcaagt ctggtaatgc tttcactcta attgatccca atgatccacc agctcgaact    1740
gcccaggtcg tcacgcagac tcgggcgact gtagcgctta cttccaagct acaccgcgag    1800
actgtacaga agcttgtagg ccgttgcgtt gtggttgatg acgagcttct gcaatcagtt    1860
tctgccagcg acgatttctc aagtctgacc aaatcgcaag acttggccta cgtgatcttc    1920
acttctggta gcacgggcga cccgaaaggc atcatgattg aacaccgagc gttctcatca    1980
tgtgcactca agttcggcgc gtctcttggc atcaactctg atactcgtgc cctacaattt    2040
ggaacccatg cctttggcgc atgtcttctc gagattatga ctactctcat caacggtggc    2100
tgcgtttgta ttccctccga cgatgatcgt atgaacagta tcccgtcctt catcaaccga    2160
tacaacgtta attggatgat ggcgacacct tcgtacatgg aaccttttc acctgaagac     2220
gttcctggcc ttgcgacatt ggtacttgtt ggggagcaga tgtcatcttc agtcaacgca    2280
atctgggccc ccaagctcca actcttgaac gggtacggac agagtgaaag ttcctcaatt    2340
tgttttgcct ccaatatgtc aactgagccc aacaacatgg gcagagcagt cggagctcat    2400
tcatgggtca ttgacccgaa cgatataaac cgactagttc cgattggagc tgtgggagaa    2460
ctggtcattg agagtccagg cattgcccgc gactacattg ttcccccccc tccggagaag    2520
tccccattct tcacagacat tccaagctgg tatccagcga cacgtttcc tgatggggca     2580
aaactctaca ggacaggaga tcttgcaaga tatgcctccg atgggtccat cgtttgcctt    2640
gggcgcatag actcgcaggt caagatccgg ggacagcgtg ttgagctggg tgccattgag    2700
acccatctcc gacagcagat gccagacgac ttgactattg tggtagaagc taccaagcga    2760
tcccaatctg ccaacagcac atccttaatt gcattcctaa tagggtcttc ttacttcgga    2820
aatagaccct cggatgccca cattctggac catgatgcta ccaaagctat caacataaag    2880
ctggagcagg tattgcctcg acactctatc ccctcattct acatctgcat gctggagctt    2940
ccacgtactg ccaccgggaa gatagatagg aggcgactac gaatcatggg caaagacatc    3000
ttggacaagc agacccaagg ggccattgtt caacaagcac ccgctcctat ccctgttttc    3060
gcagacacag cagcaaagct ccacagtatc tgggtacaga gtttgggtat cgatccagcc    3120
acggtcaatg ttggggcaac tttcttcgaa ctcggaggaa actctatcac tgctatcaag    3180
atggtgaaca tggcgaggtc cgttggtatg gacctcaagg tctctaacat ctaccagcac    3240
ccgacgcttg cgggaatttc cgcggtcgtc aagggtgatc ctctgtccta cactctcatc    3300
```

```
cccaagtcaa ctcatgaggg acctgttgag cagtcttatt cacaaggccg actatggttc    3360
ctggatcagt tggacgttgg cagtctgtgg tatctgattc catatgctgt gagaatgcgc    3420
gggcctgtca atgtcgacgc gttacgtcgg gctcttgcag cgcttgaaca gcgacacgag    3480
actcttagaa cgacatttga agaccaggat ggtgtcggtg tacaaattgt tcacgagaag    3540
ctttctgagg agatgaaggt cattgatctc tgtggttcag accttgaccc gtttgaggtg    3600
ttgaaccaag aacagactac tcccttcaat ctctcatctg aagctggctg gagagcgacg    3660
ctcttacgac ttggtgaaga tgaccacatc ctcactattg tcatgcatca catcatctca    3720
gatggttggt caattgatgt cttgcgacgc gatctcaatc agctctactc agctgcgctc    3780
aaggactcaa aagacccgct gtcagcactc actcctctac ctatccagta cagcgacttt    3840
gcaaaatggc agaaggacca attcatgaag caggagaagc aactcaacta ctggaagaag    3900
caactcaaag actcttcccc agcaaagatc ccgaccgact ttgcccgccc tgcacttctg    3960
tctggagacg caggttgcgt acatgttacc atcgacggcg agctctacca gtcccttcga    4020
gccttctgca acgaacacaa cacgacctct ttcgtcgttc ttctagctgc gttccgtgcc    4080
gctcattatc gtctcacagc tgttgaagac gctgtcattg gtacaccaat tgcgaatcgc    4140
aaccgacctg aactggagga tatcatcggc tgctttgtca atacgcagtg tatgcgaatc    4200
aacatagatc atcacgatac ctttgggact ttgatcaacc aagtcaaggc tacgacgaca    4260
gcagcattcg agaacgagga tattccgttt gagcgcgttg tatcagcact acagcctgga    4320
tccagagatc tgtcaagcac acctctcgca caactcattt ttgcagtgca ctcacagaag    4380
gaccttggaa gattcaagtt ccagggtctc gagtccgtac ctgtgcctag caaagcgtac    4440
actcgatttg acatggagtt ccatctgtttt caagaaaccg acagccttaa aggtagcgtc    4500
aactttgccg atgagctgtt caaaatggag actgttgaaa atgtcgtcag agtattcttt    4560
gagattctga gaaacgggct tcaaagttcg cggacaccag tctcaatact tcctttgact    4620
gatggcattg tgactcttga aaaattggat gttctcaacg tcaaacatgt cgactatccc    4680
cgagaatcga gcttggctga tgtcttccag acccaagtct ctgcttaccc cgatagtctg    4740
gctgtggtgg actcctcgtg ccgattgacc tacaccgagt tggatcgcca gtctgatatt    4800
ctcgctggat ggcttcgtcg acggtcaatg cctgcagaga cgcttgtcgc agtatttgcc    4860
ccacggtcat gtgagacaat tgtcgcgttc tttggtgtgt tgaaggcgaa cttggcctat    4920
cttcctctcg atgtacgatc gccctcggcg agagttcagg atatactttc tggactttct    4980
gggcctacca ttgttttgat tggccatgat acagcgcctc ccgatatcga ggttactaac    5040
gtcgagtttg ttcgtatccg ggatgcgctg aatgacagca atgcagatgg ctttgaagtc    5100 atcgagcacac acagcacaaa gccctcagcc acgagtctcg catacgtgct gtatacctca    5160
ggatccactg gccgaccaaa aggcgtcatg attgagcacc gtgtcattat tcgaacagtc    5220
acaagtggct gtatacccaa ctatccttcg gaaacgagga tggctcacat ggcgaccatt    5280
gcgtttgacg gcgcatcgta cgagatctac agcgcccttt tgttcggaag gacacttgtt    5340
tgcgttgact acatgacaac cctcgacgct agagcactca aggatgtgtt tttccgagag    5400
catgtcaacg cggcaagtca tgtcaccagc tcttctcaag atgtacctct ccgagtcccg    5460
agaaggctct cgagaacctt gatgttcttc ttcttggtgg tgacagattc gacggcccca    5520
gatgctctcg atgcgcaggg actttatcaa ggggtccagt gttacaatgg ttacggccca    5580
acagagaatg gagtcatgag tacaatctat cccattgact cgactgagtc gttcatcaat    5640
```

```
ggagtcccaa ttggacgagc tctgaacaac tcaggagcgt atgtcgtgga tcctgagcaa   5700
cagcttgttg gcattggtgt gatgggagag cttgttgtca ctggcgatgg tcttgcgcgg   5760
ggctacagtg acaaagccct tgacgagaac cgttttgtgc acattactgt caatgaccag   5820
acagtgaagg cgtatcgcac tggcgatcga gtgcggtaca ggattggaga tggcctcatc   5880
gagttcttcg gacgtatgga cacccagttc aagattcgtg gcaatcgtat cgaatcagct   5940
gagattgaag cggcccttct cgcgcgactcc tccgtccgag atgctgctgt cgtccttcag   6000
cagaatgagg atcaagcgcc tgagatcttg gggtttgttg ttgctgatca tgatcattct   6060
gagaatgaca agggacaatc tgccaatcaa gtcgaaggat ggcaagacca tttcgagagt   6120
ggcatgtatt ccgacattgg cgaaattgac ccgtcgacga ttggtagcga cttcaagggt   6180
tggacatcaa tgtatgatgg aagtcaaatc gacttcgatg agatgcacga gtggcttggt   6240
gagactaccc ggacactcca tgacaatcgc tctctaggca atgtccttga aattggaaca   6300
ggtagcggca tgatcctctt caaccttgac agcaggcttg agagttacgt tggtcttgaa   6360
ccatccagat cagcagctgc atttgtcaac aaagctaccg agtctatacc atcgcttgct   6420
ggaaaagcca aggttcaggt tggaacagct acagatattg tcaagtcga tgacttacac   6480 cctgacctcg tggttctcaa ctcagtcatt cagtatttcc cgtcttcgga gtaccttgca   6540
gaaatcgcag acaccttgat tcatctgcct aacgtgcagc ggattttctt tggcgatgtc   6600
cgatcgcagg ccaccaacga gcacttcctt gctgccaggg ctatccacac actggggaag   6660
aatgcaacga aggacgatgt tcgacagaaa atggcagaat tggaggacat ggaggaggag   6720
ttgcttgttg aacctgcttt cttcacctcg ttgaaagaca ggtttccagg tctggtggaa   6780
catgttgaga tcctgccaaa gaacatggaa gctgtgaatg agctcagtgc gtatcgatat   6840
gccgctgttg tgcacgttcg gggttcactt ggagatgagc ttgtgcttcc ggttgagaaa   6900
gatgactgga tcgactttca agcgaatcaa ttgaaccaga agtcactggg tgaccttctc   6960
aagtcttcag atgctgctat catggcagtc agcaaaattc ctttcgaaat cacggccttt   7020
gaaagacagg tcgtcgcttc cctcaatagc aacatcgatg agtggcagct atcaaccatt   7080
cggtccagcg ccgagggcga ctcatcacta tccgttcccg acatctttcg cattgctggg   7140
gaagccgggt tccgtgtcga ggtcagttct gcacgacagt ggtctcagaa tggtgcattg   7200
gacgctgttt tccatcattg ttgctcccaa gggcgtactc tggtcaactt tcctacggac   7260
catcaccttc gagggtctga tctcctcacc aatcgacccc ttcagcgact gcaaaaccgt   7320
cgtatcgcca tcgaagtccg cgagaggctt cggtccttac ttccatcgta catgatccca   7380
tcgaacatcg ttgttctgga caagatgcct ctcaacgcca atggtaaagt tgaccggaag   7440
gaactctctc gcagggcaaa ggttgtaccg aagcagcaga cagcagcgcc gttaccgaca   7500
tttcccatca gtgaggtcga agtcattctt tgcgaagaag ccactgaggt gtttggcatg   7560
aaggttgaca ttaccgatca cttcttcaat ctcggtggac actctctctt ggccacgaag   7620
ctcatttctc gtatcgacca acgactcaag gtccgtatca ctgtcaagga tgtctttgac   7680
catcctgtat ttgcggatct agcatctgtc atccgtcaag ggctgggttt gcaacaaccc   7740
gtttctgatg tcagggaca agacagatct gcccacatgg caccccgtac cgagactgaa   7800
gctatactct gtgatgagtt tgcaaaggtt ctggggttcc aagtcgggat tacagacaat   7860 ttcttttgatc ttggtggtca ttcactcatg gctactaaac tcgctgtgcg catcggacat   7920
cgacttgaca cgactgtttc ggtgaaggat gttttcgatc atcctgtact cttccaactt   7980
gcaattgcat tggataactt ggttcaatcc aagaccaatg agatagttgg aggtagagaa   8040
```

```
atggctgaat actcaccttt ccaactcctc tttacagaag acccagagga gtttatggcg    8100
agcgagatca agccacaact tgagttacag gaaatcattc aagacatata tccgtctacc    8160
cagatgcaga aggctttcct cttcgatcac acaactgcgc gcccgagacc tttcgtgccg    8220
ttctacatcg acttccccag cacttccgag cctgatgctg caggtctaat caaggcttgc    8280
gagtctctgg taaatcatct tgacatcttc agaacagtct ttgcagaggc atctggagaa    8340
ctataccaag tggtcttgtc ctgtcttgat ctgccaatcc aagtgattga cagaaagac    8400
aacatcaata cggcgacaaa tgagtttctc gatgagtttg cgaaagagcc agttcgtctg    8460
ggacatccgt tgattcgttt tacaatcatc aaacaaacca gtcgatgcg tgtgataatg    8520
agaatatcgc atgccctgta tgatggtctg agtctagagc atgtcgtgcg caaacttcac    8580
atgctctaca acgggagatc acttttgcca ccacaccaat tctcgcggta catgcagtat    8640
actgctgacg gtcgcgaaag tggacatgga ttttggcgcg atgtgattca aaatacgccc    8700
atgacaatat tgagtgatga cacggttgtt gatggaaatg atgcaacctg caaggcgttg    8760
cacctatcaa agattgtcaa tattccttca caggtacttc gaggcagcag taacatcatt    8820
actcaagcta ctgtgtttaa cgcagcctgc gcgttagtct tgtcacggga atctgactcg    8880
aaagacgttg tctttggacg catcgtctct ggtcgtcaag gcttgcctgt tgaataccag    8940
gacattgtcg ggccttgtac caacgcagtt cctgttcgcg ctcatataga gtcgtcagat    9000
tacaaccaat tgctgcacga catccaagac cagtaccttc tcagcttgcc acacgaaaca    9060
attggcttct cagatctcaa gcgcaactgt acagattggc cagaagcaat caccaacttc    9120
tcatgctgca tcacatacca caatttcgag taccatcccg agagtcagtt cgaacagcag    9180
agagttgaga tgggtgtatt gacaaagttt gtcaacattg agatggatga gccactatat    9240
gatttggcga ttgcgggtga agttgaacca gacggagcag gactgaaggt tactgttatc    9300
gcgaagacgc agttatttgg taggaagaga gtagaacatc tgttggagga agtttccaaa    9360
acgtttgagg gtctcaactc ttctttgtaa                                     9390
```

<210> SEQ ID NO 94
<211> LENGTH: 3129
<212> TYPE: PRT
<213> ORGANISM: Fusarium venenatum

<400> SEQUENCE: 94

```
Met Glu Tyr Leu Thr Ala Val Asp Gly Arg Gln Asp Leu Pro Pro Thr
1               5                   10                  15
Pro Ala Ser Phe Cys Ser His Gly Asp Ser Pro Leu Asn Ser Ser Tyr
            20                  25                  30
Glu Gln Leu Phe His Leu Tyr Gly Leu Asp Ser Ser Arg Ile Glu Ala
        35                  40                  45
Ile Lys Pro Cys Thr Pro Phe Gln Leu Asp Met Ile Asp Cys Asn Ala
    50                  55                  60
Leu Asp Lys Gln Ser Ala Ile Gly His Ala Val Tyr Asp Val Pro Thr
65                  70                  75                  80
Asp Ile Asp Ile Ser Arg Phe Ala Leu Ala Trp Lys Glu Ile Val Asn
                85                  90                  95
Gln Thr Pro Ala Leu Arg Ala Phe Ala Phe Thr Ser Asp Ser Gly Lys
            100                 105                 110
Thr Ser Gln Val Ile Leu Lys Asp Ser Phe Val Phe Ser Trp Met Cys
        115                 120                 125
```

-continued

```
Trp Ser Ser Ser Ser Pro Asp Glu Val Val Arg Asp Glu Ala Ala
    130             135             140

Ala Ala Ala Ser Gly Pro Arg Cys Asn Arg Phe Val Leu Leu Glu Asp
145             150             155                 160

Met Gln Thr Lys Lys Cys Gln Leu Val Trp Thr Phe Ser His Ala Leu
            165             170                 175

Val Asp Val Thr Phe Gln Gln Arg Val Leu Ser Arg Val Phe Ala Ala
            180             185             190

Tyr Lys His Glu Lys Asp Thr His Arg Pro Glu Thr Pro Glu Ser Ser
        195             200             205

Asp Ala Thr Asp Thr Asp Ser Gln Ser Val Ser Val Ser Met Ser
    210             215             220

Cys Glu Asp Asn Ala Val Ser Ala Thr His Phe Trp Gln Thr His Leu
225             230             235                 240

Asn Asp Leu Asn Ala Ser Val Phe Pro His Leu Ser Asp His Leu Met
                245             250             255

Val Pro Asn Pro Thr Thr Thr Ala Glu His Arg Ile Thr Phe Pro Leu
            260             265             270

Ser Gln Lys Ala Leu Ser Asn Ser Ala Ile Cys Arg Thr Ala Leu Ser
        275             280             285

Ile Leu Leu Ser Arg Tyr Thr His Ser Asp Glu Ala Leu Phe Gly Ala
    290             295             300

Val Thr Glu Gln Ser Leu Pro Phe Asp Lys His Tyr Leu Ala Asp Gly
305             310             315                 320

Thr Tyr Gln Thr Val Ala Pro Leu Arg Val His Cys Gln Ser Asn Leu
            325             330             335

Arg Ala Ser Asp Val Met Asp Ala Ile Ser Ser Tyr Asp Asp Arg Leu
            340             345             350

Gly His Leu Ala Pro Phe Gly Leu Arg Asp Ile Arg Asn Thr Gly Asp
        355             360             365

Asn Gly Ser Ala Ala Cys Asp Phe Gln Thr Val Leu Leu Val Thr Asp
370             375             380

Gly Ser His Val Asn Asn Gly Ile Asn Gly Phe Leu Gln Gln Ile Thr
385             390             395             400

Glu Ser Ser His Phe Met Pro Cys Asn Asn Arg Ala Leu Leu Leu His
            405             410             415

Cys Gln Met Glu Ser Ser Gly Ala Leu Leu Val Ala Tyr Tyr Asp His
            420             425             430

Asn Val Ile Asp Ser Leu Gln Thr Thr Arg Leu Leu Gln Gln Phe Gly
        435             440             445

His Leu Ile Lys Cys Leu Gln Ser Pro Leu Asp Leu Ser Ser Met Ala
    450             455             460

Glu Val Asn Leu Met Thr Glu Tyr Asp Arg Ala Glu Ile Glu Ser Trp
465             470             475                 480

Asn Ser Gln Pro Leu Glu Val Gln Asp Thr Leu Ile His His Glu Met
            485             490             495

Leu Lys Ala Val Ser His Ser Pro Thr Lys Thr Ala Ile Gln Ala Trp
            500             505             510

Asp Gly Asp Trp Thr Tyr Ser Glu Leu Asp Asn Val Ser Ser Arg Leu
        515             520             525

Ala Val His Ile Lys Ser Leu Gly Leu Arg Ala Gln Gln Ala Ile Ile
    530             535             540

Pro Val Tyr Phe Glu Lys Ser Lys Trp Val Ile Ala Ser Met Leu Ala
```

```
            545                 550                 555                 560
        Val Leu Lys Ser Gly Asn Ala Phe Thr Leu Ile Asp Pro Asn Asp Pro
                            565                 570                 575

Pro Ala Arg Thr Ala Gln Val Val Thr Gln Thr Arg Ala Thr Val Ala
                            580                 585                 590

Leu Thr Ser Lys Leu His Arg Glu Thr Val Gln Lys Leu Val Gly Arg
                            595                 600                 605

Cys Val Val Asp Asp Glu Leu Leu Gln Ser Val Ser Ala Ser Asp
            610                 615                 620

Asp Phe Ser Ser Leu Thr Lys Ser Gln Asp Leu Ala Tyr Val Ile Phe
        625                 630                 635                 640

Thr Ser Gly Ser Thr Gly Asp Pro Lys Gly Ile Met Ile Glu His Arg
                            645                 650                 655

Ala Phe Ser Ser Cys Ala Leu Lys Phe Gly Ala Ser Leu Gly Ile Asn
                            660                 665                 670

Ser Asp Thr Arg Ala Leu Gln Phe Gly Thr His Ala Phe Gly Ala Cys
                            675                 680                 685

Leu Leu Glu Ile Met Thr Thr Leu Ile Asn Gly Gly Cys Val Cys Ile
                            690                 695                 700

Pro Ser Asp Asp Asp Arg Met Asn Ser Ile Pro Ser Phe Ile Asn Arg
        705                 710                 715                 720

Tyr Asn Val Asn Trp Met Met Ala Thr Pro Ser Tyr Met Gly Thr Phe
                            725                 730                 735

Ser Pro Glu Asp Val Pro Gly Leu Ala Thr Leu Val Leu Val Gly Glu
                            740                 745                 750

Gln Met Ser Ser Ser Val Asn Ala Ile Trp Ala Pro Lys Leu Gln Leu
                            755                 760                 765

Leu Asn Gly Tyr Gly Gln Ser Glu Ser Ser Ile Cys Phe Ala Ser
                            770                 775                 780

Asn Met Ser Thr Glu Pro Asn Asn Met Gly Arg Ala Val Gly Ala His
        785                 790                 795                 800

Ser Trp Val Ile Asp Pro Asn Asp Ile Asn Arg Leu Val Pro Ile Gly
                            805                 810                 815

Ala Val Gly Glu Leu Val Ile Glu Ser Pro Gly Ile Ala Arg Asp Tyr
                            820                 825                 830

Ile Val Pro Pro Pro Glu Lys Ser Pro Phe Phe Thr Asp Ile Pro
                            835                 840                 845

Ser Trp Tyr Pro Ala Asn Thr Phe Pro Asp Gly Ala Lys Leu Tyr Arg
        850                 855                 860

Thr Gly Asp Leu Ala Arg Tyr Ala Ser Asp Gly Ser Ile Val Cys Leu
        865                 870                 875                 880

Gly Arg Ile Asp Ser Gln Val Lys Ile Arg Gly Gln Arg Val Glu Leu
                            885                 890                 895

Gly Ala Ile Glu Thr His Leu Arg Gln Gln Met Pro Asp Asp Leu Thr
                            900                 905                 910

Ile Val Val Glu Ala Thr Lys Arg Ser Gln Ser Ala Asn Ser Thr Ser
                            915                 920                 925

Leu Ile Ala Phe Leu Ile Gly Ser Ser Tyr Phe Gly Asn Arg Pro Ser
                            930                 935                 940

Asp Ala His Ile Leu Asp His Asp Ala Thr Lys Ala Ile Asn Ile Lys
        945                 950                 955                 960

Leu Glu Gln Val Leu Pro Arg His Ser Ile Pro Ser Phe Tyr Ile Cys
                            965                 970                 975
```

```
Met Leu Glu Leu Pro Arg Thr Ala Thr Gly Lys Ile Asp Arg Arg Arg
            980                 985                 990

Leu Arg Ile Met Gly Lys Asp Ile Leu Asp Lys Gln Thr Gln Gly Ala
            995                1000                1005

Ile Val Gln Gln Ala Pro Ala Pro Ile Pro Val Phe Ala Asp Thr
   1010                1015                1020

Ala Ala Lys Leu His Ser Ile Trp Val Gln Ser Leu Gly Ile Asp
   1025                1030                1035

Pro Ala Thr Val Asn Val Gly Ala Thr Phe Phe Glu Leu Gly Gly
   1040                1045                1050

Asn Ser Ile Thr Ala Ile Lys Met Val Asn Met Ala Arg Ser Val
   1055                1060                1065

Gly Met Asp Leu Lys Val Ser Asn Ile Tyr Gln His Pro Thr Leu
   1070                1075                1080

Ala Gly Ile Ser Ala Val Val Lys Gly Asp Pro Leu Ser Tyr Thr
   1085                1090                1095

Leu Ile Pro Lys Ser Thr His Glu Gly Pro Val Glu Gln Ser Tyr
   1100                1105                1110

Ser Gln Gly Arg Leu Trp Phe Leu Asp Gln Leu Asp Val Gly Ser
   1115                1120                1125

Leu Trp Tyr Leu Ile Pro Tyr Ala Val Arg Met Arg Gly Pro Val
   1130                1135                1140

Asn Val Asp Ala Leu Arg Arg Ala Leu Ala Ala Leu Glu Gln Arg
   1145                1150                1155

His Glu Thr Leu Arg Thr Thr Phe Glu Asp Gln Asp Gly Val Gly
   1160                1165                1170

Val Gln Ile Val His Glu Lys Leu Ser Glu Glu Met Lys Val Ile
   1175                1180                1185

Asp Leu Cys Gly Ser Asp Leu Asp Pro Phe Glu Val Leu Asn Gln
   1190                1195                1200

Glu Gln Thr Thr Pro Phe Asn Leu Ser Ser Glu Ala Gly Trp Arg
   1205                1210                1215

Ala Thr Leu Leu Arg Leu Gly Glu Asp Asp His Ile Leu Thr Ile
   1220                1225                1230

Val Met His His Ile Ile Ser Asp Gly Trp Ser Ile Asp Val Leu
   1235                1240                1245

Arg Arg Asp Leu Asn Gln Leu Tyr Ser Ala Ala Leu Lys Asp Ser
   1250                1255                1260

Lys Asp Pro Leu Ser Ala Leu Thr Pro Leu Pro Ile Gln Tyr Ser
   1265                1270                1275

Asp Phe Ala Lys Trp Gln Lys Asp Gln Phe Ile Glu Gln Glu Lys
   1280                1285                1290

Gln Leu Asn Tyr Trp Lys Lys Gln Leu Lys Asp Ser Ser Pro Ala
   1295                1300                1305

Lys Ile Pro Thr Asp Phe Ala Arg Pro Ala Leu Leu Ser Gly Asp
   1310                1315                1320

Ala Gly Cys Val His Val Thr Ile Asp Gly Glu Leu Tyr Gln Ser
   1325                1330                1335

Leu Arg Ala Phe Cys Asn Glu His Asn Thr Thr Ser Phe Val Val
   1340                1345                1350

Leu Leu Ala Ala Phe Arg Ala Ala His Tyr Arg Leu Thr Ala Val
   1355                1360                1365
```

-continued

```
Glu Asp Ala Val Ile Gly Thr Pro Ile Ala Asn Arg Asn Arg Pro
1370            1375                1380

Glu Leu Glu Asp Ile Ile Gly Cys Phe Val Asn Thr Gln Cys Met
1385            1390                1395

Arg Ile Asn Ile Asp His His Asp Thr Phe Gly Thr Leu Ile Asn
1400            1405                1410

Gln Val Lys Ala Thr Thr Thr Ala Ala Phe Glu Asn Glu Asp Ile
1415            1420                1425

Pro Phe Glu Arg Val Val Ser Ala Leu Gln Pro Gly Ser Arg Asp
1430            1435                1440

Leu Ser Ser Thr Pro Leu Ala Gln Leu Ile Phe Ala Val His Ser
1445            1450                1455

Gln Lys Asp Leu Gly Arg Phe Lys Phe Gln Gly Leu Glu Ser Val
1460            1465                1470

Pro Val Pro Ser Lys Ala Tyr Thr Arg Phe Asp Met Glu Phe His
1475            1480                1485

Leu Phe Gln Glu Thr Asp Ser Leu Lys Gly Ser Val Asn Phe Ala
1490            1495                1500

Asp Glu Leu Phe Lys Met Glu Thr Val Glu Asn Val Val Arg Val
1505            1510                1515

Phe Phe Glu Ile Leu Arg Asn Gly Leu Gln Ser Ser Arg Thr Pro
1520            1525                1530

Val Ser Ile Leu Pro Leu Thr Asp Gly Ile Val Thr Leu Glu Lys
1535            1540                1545

Leu Asp Val Leu Asn Val Lys His Val Asp Tyr Pro Arg Glu Ser
1550            1555                1560

Ser Leu Ala Asp Val Phe Gln Thr Gln Val Ser Ala Tyr Pro Asp
1565            1570                1575

Ser Leu Ala Val Val Asp Ser Ser Cys Arg Leu Thr Tyr Thr Glu
1580            1585                1590

Leu Asp Arg Gln Ser Asp Ile Leu Ala Gly Trp Leu Arg Arg Arg
1595            1600                1605

Ser Met Pro Ala Glu Thr Leu Val Ala Val Phe Ala Pro Arg Ser
1610            1615                1620

Cys Glu Thr Ile Val Ala Phe Phe Gly Val Leu Lys Ala Asn Leu
1625            1630                1635

Ala Tyr Leu Pro Leu Asp Val Arg Ser Pro Ser Ala Arg Val Gln
1640            1645                1650

Asp Ile Leu Ser Gly Leu Ser Gly Pro Thr Ile Val Leu Ile Gly
1655            1660                1665

His Asp Thr Ala Pro Pro Asp Ile Glu Val Thr Asn Val Glu Phe
1670            1675                1680

Val Arg Ile Arg Asp Ala Leu Asn Asp Ser Asn Ala Asp Gly Phe
1685            1690                1695

Glu Val Ile Glu His Asp Ser Thr Lys Pro Ser Ala Thr Ser Leu
1700            1705                1710

Ala Tyr Val Leu Tyr Thr Ser Gly Ser Thr Gly Arg Pro Lys Gly
1715            1720                1725

Val Met Ile Glu His Arg Val Ile Ile Arg Thr Val Thr Ser Gly
1730            1735                1740

Cys Ile Pro Asn Tyr Pro Ser Glu Thr Arg Met Ala His Met Ala
1745            1750                1755

Thr Ile Ala Phe Asp Gly Ala Ser Tyr Glu Ile Tyr Ser Ala Leu
```

```
                1760                1765                1770

Leu Phe Gly Arg Thr Leu Val Cys Val Asp Tyr Met Thr Thr Leu
    1775                1780                1785

Asp Ala Arg Ala Leu Lys Asp Val Phe Phe Arg Glu His Val Asn
    1790                1795                1800

Ala Ala Ser His Val Thr Ser Ser Ser Gln Asp Val Pro Leu Arg
    1805                1810                1815

Val Pro Arg Arg Leu Ser Arg Thr Leu Met Phe Phe Phe Leu Val
    1820                1825                1830

Val Thr Asp Ser Thr Ala Pro Asp Ala Leu Asp Ala Gln Gly Leu
    1835                1840                1845

Tyr Gln Gly Val Gln Cys Tyr Asn Gly Tyr Gly Pro Thr Glu Asn
    1850                1855                1860

Gly Val Met Ser Thr Ile Tyr Pro Ile Asp Ser Thr Glu Ser Phe
    1865                1870                1875

Ile Asn Gly Val Pro Ile Gly Arg Ala Leu Asn Asn Ser Gly Ala
    1880                1885                1890

Tyr Val Val Asp Pro Glu Gln Gln Leu Val Gly Ile Gly Val Met
    1895                1900                1905

Gly Glu Leu Val Val Thr Gly Asp Gly Leu Ala Arg Gly Tyr Ser
    1910                1915                1920

Asp Lys Ala Leu Asp Glu Asn Arg Phe Val His Ile Thr Val Asn
    1925                1930                1935

Asp Gln Thr Val Lys Ala Tyr Arg Thr Gly Asp Arg Val Arg Tyr
    1940                1945                1950

Arg Ile Gly Asp Gly Leu Ile Glu Phe Phe Gly Arg Met Asp Thr
    1955                1960                1965

Gln Phe Lys Ile Arg Gly Asn Arg Ile Glu Ser Ala Glu Ile Glu
    1970                1975                1980

Ala Ala Leu Leu Arg Asp Ser Ser Val Arg Asp Ala Ala Val Val
    1985                1990                1995

Leu Gln Gln Asn Glu Asp Gln Ala Pro Glu Ile Leu Gly Phe Val
    2000                2005                2010

Val Ala Asp His Asp His Ser Glu Asn Asp Lys Gly Gln Ser Ala
    2015                2020                2025

Asn Gln Val Glu Gly Trp Gln Asp His Phe Glu Ser Gly Met Tyr
    2030                2035                2040

Ser Asp Ile Gly Glu Ile Asp Pro Ser Thr Ile Gly Ser Asp Phe
    2045                2050                2055

Lys Gly Trp Thr Ser Met Tyr Asp Gly Ser Gln Ile Asp Phe Asp
    2060                2065                2070

Glu Met His Glu Trp Leu Gly Glu Thr Thr Arg Thr Leu His Asp
    2075                2080                2085

Asn Arg Ser Leu Gly Asn Val Leu Glu Ile Gly Thr Gly Ser Gly
    2090                2095                2100

Met Ile Leu Phe Asn Leu Asp Ser Arg Leu Glu Ser Tyr Val Gly
    2105                2110                2115

Leu Glu Pro Ser Arg Ser Ala Ala Ala Phe Val Asn Lys Ala Thr
    2120                2125                2130

Glu Ser Ile Pro Ser Leu Ala Gly Lys Ala Lys Val Gln Val Gly
    2135                2140                2145

Thr Ala Thr Asp Ile Gly Gln Val Asp Asp Leu His Pro Asp Leu
    2150                2155                2160
```

-continued

Val Val Leu Asn Ser Val Ile Gln Tyr Phe Pro Ser Ser Glu Tyr
    2165            2170            2175

Leu Ala Glu Ile Ala Asp Thr Leu Ile His Leu Pro Asn Val Gln
    2180            2185            2190

Arg Ile Phe Phe Gly Asp Val Arg Ser Gln Ala Thr Asn Glu His
    2195            2200            2205

Phe Leu Ala Ala Arg Ala Ile His Thr Leu Gly Lys Asn Ala Thr
    2210            2215            2220

Lys Asp Asp Val Arg Gln Lys Met Ala Glu Leu Glu Asp Met Glu
    2225            2230            2235

Glu Glu Leu Leu Val Glu Pro Ala Phe Phe Thr Ser Leu Lys Asp
    2240            2245            2250

Arg Phe Pro Gly Leu Val Glu His Val Glu Ile Leu Pro Lys Asn
    2255            2260            2265

Met Glu Ala Val Asn Glu Leu Ser Ala Tyr Arg Tyr Ala Ala Val
    2270            2275            2280

Val His Val Arg Gly Ser Leu Gly Asp Glu Leu Val Leu Pro Val
    2285            2290            2295

Glu Lys Asp Asp Trp Ile Asp Phe Gln Ala Asn Gln Leu Asn Gln
    2300            2305            2310

Lys Ser Leu Gly Asp Leu Leu Lys Ser Ser Asp Ala Ala Ile Met
    2315            2320            2325

Ala Val Ser Lys Ile Pro Phe Glu Ile Thr Ala Phe Glu Arg Gln
    2330            2335            2340

Val Val Ala Ser Leu Asn Ser Asn Ile Asp Glu Trp Gln Leu Ser
    2345            2350            2355

Thr Ile Arg Ser Ser Ala Glu Gly Asp Ser Ser Leu Ser Val Pro
    2360            2365            2370

Asp Ile Phe Arg Ile Ala Gly Glu Ala Gly Phe Arg Val Glu Val
    2375            2380            2385

Ser Ser Ala Arg Gln Trp Ser Gln Asn Gly Ala Leu Asp Ala Val
    2390            2395            2400

Phe His His Cys Cys Ser Gln Gly Arg Thr Leu Val Asn Phe Pro
    2405            2410            2415

Thr Asp His His Leu Arg Gly Ser Asp Leu Leu Thr Asn Arg Pro
    2420            2425            2430

Leu Gln Arg Leu Gln Asn Arg Arg Ile Ala Ile Glu Val Arg Glu
    2435            2440            2445

Arg Leu Arg Ser Leu Leu Pro Ser Tyr Met Ile Pro Ser Asn Ile
    2450            2455            2460

Val Val Leu Asp Lys Met Pro Leu Asn Ala Asn Gly Lys Val Asp
    2465            2470            2475

Arg Lys Glu Leu Ser Arg Arg Ala Lys Val Val Pro Lys Gln Gln
    2480            2485            2490

Thr Ala Ala Pro Leu Pro Thr Phe Pro Ile Ser Glu Val Glu Val
    2495            2500            2505

Ile Leu Cys Glu Glu Ala Thr Glu Val Phe Gly Met Lys Val Asp
    2510            2515            2520

Ile Thr Asp His Phe Phe Asn Leu Gly Gly His Ser Leu Leu Ala
    2525            2530            2535

Thr Lys Leu Ile Ser Arg Ile Asp Gln Arg Leu Lys Val Arg Ile
    2540            2545            2550

-continued

```
Thr Val Lys Asp Val Phe Asp His Pro Val Phe Ala Asp Leu Ala
2555                2560                2565

Ser Val Ile Arg Gln Gly Leu Gly Leu Gln Gln Pro Val Ser Asp
2570                2575                2580

Gly Gln Gly Gln Asp Arg Ser Ala His Met Ala Pro Arg Thr Glu
2585                2590                2595

Thr Glu Ala Ile Leu Cys Asp Glu Phe Ala Lys Val Leu Gly Phe
2600                2605                2610

Gln Val Gly Ile Thr Asp Asn Phe Phe Asp Leu Gly Gly His Ser
2615                2620                2625

Leu Met Ala Thr Lys Leu Ala Val Arg Ile Gly His Arg Leu Asp
2630                2635                2640

Thr Thr Val Ser Val Lys Asp Val Phe Asp His Pro Val Leu Phe
2645                2650                2655

Gln Leu Ala Ile Ala Leu Asp Asn Leu Val Gln Ser Lys Thr Asn
2660                2665                2670

Glu Ile Val Gly Gly Arg Glu Met Ala Glu Tyr Ser Pro Phe Gln
2675                2680                2685

Leu Leu Phe Thr Glu Asp Pro Glu Glu Phe Met Ala Ser Glu Ile
2690                2695                2700

Lys Pro Gln Leu Glu Leu Gln Glu Ile Ile Gln Asp Ile Tyr Pro
2705                2710                2715

Ser Thr Gln Met Gln Lys Ala Phe Leu Phe Asp His Thr Thr Ala
2720                2725                2730

Arg Pro Arg Pro Phe Val Pro Phe Tyr Ile Asp Phe Pro Ser Thr
2735                2740                2745

Ser Glu Pro Asp Ala Ala Gly Leu Ile Lys Ala Cys Glu Ser Leu
2750                2755                2760

Val Asn His Leu Asp Ile Phe Arg Thr Val Phe Ala Glu Ala Ser
2765                2770                2775

Gly Glu Leu Tyr Gln Val Val Leu Ser Cys Leu Asp Leu Pro Ile
2780                2785                2790

Gln Val Ile Glu Thr Glu Asp Asn Ile Asn Thr Ala Thr Asn Glu
2795                2800                2805

Phe Leu Asp Glu Phe Ala Lys Glu Pro Val Arg Leu Gly His Pro
2810                2815                2820

Leu Ile Arg Phe Thr Ile Ile Lys Gln Thr Lys Ser Met Arg Val
2825                2830                2835

Ile Met Arg Ile Ser His Ala Leu Tyr Asp Gly Leu Ser Leu Glu
2840                2845                2850

His Val Val Arg Lys Leu His Met Leu Tyr Asn Gly Arg Ser Leu
2855                2860                2865

Leu Pro Pro His Gln Phe Ser Arg Tyr Met Gln Tyr Thr Ala Asp
2870                2875                2880

Gly Arg Glu Ser Gly His Gly Phe Trp Arg Asp Val Ile Gln Asn
2885                2890                2895

Thr Pro Met Thr Ile Leu Ser Asp Asp Thr Val Asp Gly Asn
2900                2905                2910

Asp Ala Thr Cys Lys Ala Leu His Leu Ser Lys Ile Val Asn Ile
2915                2920                2925

Pro Ser Gln Val Leu Arg Gly Ser Ser Asn Ile Ile Thr Gln Ala
2930                2935                2940

Thr Val Phe Asn Ala Ala Cys Ala Leu Val Leu Ser Arg Glu Ser
```

```
    2945                2950                2955

Asp Ser  Lys Asp Val Val Phe  Gly Arg Ile Val Ser  Gly Arg Gln
    2960                2965                2970

Gly Leu  Pro Val Glu Tyr Gln  Asp Ile Val Gly Pro  Cys Thr Asn
    2975                2980                2985

Ala Val  Pro Val Arg Ala His  Ile Glu Ser Ser Asp  Tyr Asn Gln
    2990                2995                3000

Leu Leu  His Asp Ile Gln Asp  Gln Tyr Leu Leu Ser  Leu Pro His
    3005                3010                3015

Glu Thr  Ile Gly Phe Ser Asp  Leu Lys Arg Asn Cys  Thr Asp Trp
    3020                3025                3030

Pro Glu  Ala Ile Thr Asn Phe  Ser Cys Cys Ile Thr  Tyr His Asn
    3035                3040                3045

Phe Glu  Tyr His Pro Glu Ser  Gln Phe Glu Gln Gln  Arg Val Glu
    3050                3055                3060

Met Gly  Val Leu Thr Lys Phe  Val Asn Ile Glu Met  Asp Glu Pro
    3065                3070                3075

Leu Tyr  Asp Leu Ala Ile Ala  Gly Glu Val Glu Pro  Asp Gly Ala
    3080                3085                3090

Gly Leu  Lys Val Thr Val Ile  Ala Lys Thr Gln Leu  Phe Gly Arg
    3095                3100                3105

Lys Arg  Val Glu His Leu Leu  Glu Glu Val Ser Lys  Thr Phe Glu
    3110                3115                3120

Gly Leu  Asn Ser Ser Leu
    3125

<210> SEQ ID NO 95
<211> LENGTH: 38
<212> TYPE: DNA
<213> ORGANISM: Fusarium venenatum

<400> SEQUENCE: 95
gactaagccc tgcaggttgg tctcaatcgt cgcgacag                          38

<210> SEQ ID NO 96
<211> LENGTH: 46
<212> TYPE: DNA
<213> ORGANISM: Fusarium venenatum

<400> SEQUENCE: 96
agtctacccc tgcaggcggc cgctggcatc ggtggacgta acacgc                 46

<210> SEQ ID NO 97
<211> LENGTH: 30
<212> TYPE: DNA
<213> ORGANISM: Fusarium venenatum

<400> SEQUENCE: 97
gctattgagg ggactatctc catgactaca                                   30

<210> SEQ ID NO 98
<211> LENGTH: 29
<212> TYPE: DNA
<213> ORGANISM: Fusarium venenatum

<400> SEQUENCE: 98
gcctaccatc gacagcagta agatattcc                                    29
```

```
<210> SEQ ID NO 99
<211> LENGTH: 50
<212> TYPE: DNA
<213> ORGANISM: Fusarium venenatum

<400> SEQUENCE: 99
atgtgctaca ggcgcgccgc ggccgcgagt tccaacatgt cttattatcc              50

<210> SEQ ID NO 100
<211> LENGTH: 41
<212> TYPE: DNA
<213> ORGANISM: Fusarium venenatum

<400> SEQUENCE: 100
tactgtaccg gcgcgccatc tgagccaaga gactcattca t                       41

<210> SEQ ID NO 101
<211> LENGTH: 25
<212> TYPE: DNA
<213> ORGANISM: Fusarium venenatum

<400> SEQUENCE: 101
cttgactatt atctcacgtt gtcag                                         25

<210> SEQ ID NO 102
<211> LENGTH: 25
<212> TYPE: DNA
<213> ORGANISM: Fusarium venenatum

<400> SEQUENCE: 102
tcaagtgttg tgtaatgttg gaaca                                         25
```

METHODS FOR PRODUCING POLYPEPTIDES IN ENZYME-DEFICIENT MUTANTS OF *FUSARIUM VENENTATUM*

CROSS-REFERENCE TO RELATED APPLICATIONS

This application is a continuation of U.S. application Ser. No. 14/168,766, filed on Jan. 30, 2014, now U.S. Pat. No. 9,255,275, which is a continuation of U.S. application Ser. No. 13/121,254, filed on Jun. 1, 2011, now U.S. Pat. No. 8,647,856, which is a 35 U.S.C. §371 national application of PCT/US2009/059039, filed on Sep. 30, 2009, which claims the benefit of U.S. Provisional Application No. 61/101,250, filed on Sep. 30, 2008, which applications are fully incorporated herein by reference.

REFERENCE TO A SEQUENCE LISTING

This application contains a Sequence Listing in computer readable form. The computer readable form is incorporated herein by reference.

BACKGROUND OF THE INVENTION

Field of the Invention

The present invention relates to methods of producing polypeptides in enzyme-deficient *Fusarium venenatum* mutant strains, enzyme-deficient *Fusarium venenatum* mutant strains, and methods of obtaining the enzyme-deficient *Fusarium venenatum* mutant strains.

Description of the Related Art

*Fusarium venenatum* has been shown to be useful as a host cell for the recombinant production of polypeptides having biological activity (WO 96/00787, WO 97/26330). *Fusarium venenatum* hosts with the desirable traits of increased protein expression and secretion may not necessarily have the most desirable characteristics for successful fermentation. The fermentation may not be optimal because of the production of biological substances, e.g., enzymes, detrimental to the production, recovery, or application of a particular polypeptide of interest.

WO 99/60137 discloses trichothecene-deficient mutants of *Fusarium venenatum*. WO 00/42203 discloses cyclohexadepsipeptide-deficient mutants of *Fusarium venenatum*.

The present invention relates to improved *Fusarium venenatum* hosts that combine the capacity for expression of commercial quantities of a polypeptide of interest while being deficient in the production of enzymes that can complicate recovery and downstream processing of the polypeptide.

SUMMARY OF THE INVENTION

The present invention relates to methods of producing a polypeptide, comprising:

(a) cultivating a mutant of a parent *Fusarium venenatum* strain in a medium for the production of the polypeptide, wherein the mutant strain comprises a polynucleotide encoding the polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions; and (b) recovering the polypeptide from the cultivation medium.

In one aspect of the methods of producing a polypeptide, the mutant strain further comprises one or both of the genes tri5 and dps1, wherein the one or both genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

The present invention also relates to mutants of a parent *Fusarium venenatum* strain, comprising a polynucleotide encoding a polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

In one aspect, the mutants of a parent *Fusarium venenatum* strain further comprise one or both of the genes tri5 and dps1, wherein the one or both genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

The present invention also relates to methods of obtaining mutants of a parent *Fusarium venenatum* strain, comprising:

(a) modifying one or more (several) genes selected from the group consisting of pyrG, amyA, and alpA; and (b) identifying a mutant strain from step (a) wherein the one or more (several) genes selected from the group consisting of pyrG, amyA, and alpA are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

In one aspect, the methods of obtaining mutants of a parent *Fusarium venenatum* strain further comprise modifying one or both of the genes tri5 and dps1 rendering the mutant strain deficient in the production of one or both enzymes trichodiene synthase and cyclohexadepsipeptide synthetase, respectively, compared to the parent *Fusarium venenatum* strain when cultivated under identical conditions.

DEFINITIONS

Figure 1:
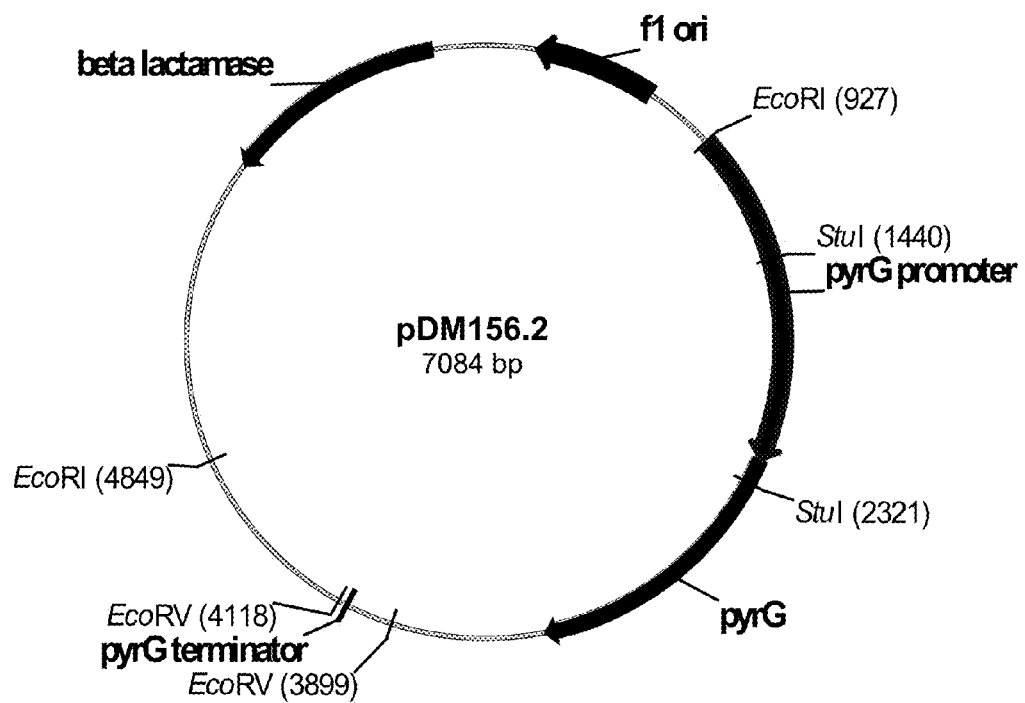
FIG. 1 shows a restriction map of pDM156.2.

Orotidine-5'-monophosphate decarboxylase: The term "orotidine-5'-monophosphate decarboxylase" is defined herein as a UTP:ammonia ligase (ADP-forming) (EC 6.3.4.2) that catalyzes the conversion of ATP+UTP+NH$_3$ to ADP+phosphate+CTP. For purposes of the present invention, orotidine-5'-monophosphate decarboxylase activity is determined according to the method described by Liberman, 1956, *Journal of Biological Chemistry* 222: 765-775).

Alpha-amylase: The term "alpha-amylase" is defined herein as an 1,4-α-D-glucan glucanohydrolase (EC 3.2.1.1) that catalyzes the endohydrolysis of 1,4-α-D-glucosidic linkages in polysaccharides containing three or more 1,4-α-linked D-glucose units. For purposes of the present invention, alpha-amylase activity is determined using 4,6-ethylidene (G7)-p-nitrophenyl (G1)-alpha-D-maltoheptaside as substrate and Sigma Chemical Co. Kit 577 (St. Louis, Mo., USA) at pH 7.0.

Alkaline protease: The term "alkaline protease" is defined herein as a serine protease that catalyzes the hydrolysis of peptide bonds in proteins. For purposes of the present invention, alkaline protease activity is determined according to the procedure described in Example 28.

Trichothecenes: The term "trichothecenes" is defined herein as a family of sesquiterpene epoxides produced by a sequence of oxygenations, isomerizations, cyclizations, and esterifications leading from trichodiene to the more complex trichothecenes (Desjardins, Hohn, and McCormick, 1993, *Microbiological Reviews* 57: 595-604). Trichothecenes include, but are not limited to, 2-hydroxytrichodiene, 12,13-epoxy-9,10-trichoene-2-ol, isotrichodiol, isotrichotriol, trichotriol, isotrichodermol, isotrichodermin, 15-decalonectrin, 3,15-didecalonectrin, deoxynivalenol, 3-acetyldeoxynivalenol, calonectrin, 3,15-diacetoxyscirpenol, 3,4,15-triacetoxyscirpenol, 4,15-diacetoxyscirpenol, 3-acetylneosolaniol, acetyl T-2 toxin, and T-2 toxin; and derivatives thereof.

Trichodiene synthase: The term "trichodiene synthase" is defined herein as a dextrin 6-alpha-D-glucanohydrolase that catalyses the isomerization-cyclization of farnesylpyrophosphate to form the bicyclic olefin trichodiene. For purposes of the present invention, trichodiene synthase activity is determined according to the procedure described by Hohn and Beremand, 1989, *Applied and Environmental Microbiology* 55: 1500-1503.

The level of trichothecenes produced by a mutant *Fusarium venenatum* strain of the present invention may be determined using methods well known in the art (see, for example, Rood et al., 1988, *Journal of Agricultural and Food Chemistry* 36: 74-79; Romer, 1986, *Journal of the Association of Official Analytical Chemists* 69: 699-703; McCormick et al., 1990, *Applied and Environmental Microbiology* 56: 702-706).

Cyclohexadepsipeptides: The term "cyclohexadepsipeptides" is defined herein as a family of peptide-related compounds composed of hydroxy and amino acids linked by amide and ester bonds. The term cyclohexadepsipeptides includes, but is not limited to, enniatins.

Enniatins: The term "enniatins" is defined herein as a family of cyclohexadepsipeptides composed of three D-2-hydroxyisovaleric acid residues joined alternatively to L-amino acids or N-methyl-L-amino acids to produce an 18-membered cyclic structure. Enniatins are cyclohexadepsipeptide phytoxins with ionophoretic properties produced by various species of actinomycetes and filamentous fungi, particularly strains of *Fusarium*. The enniatins include, but are not limited to, enniatin A, $A_1$, B, $B_1$, $B_2$, $B_3$, $B_4$, C, D, E, and F; and derivatives thereof (Visconte et al., 1992, *Journal of Agricultural and Food Chemistry* 40: 1076-1082; Tomodo et al., 1992, *Journal of Antibiotics* 45: 1207-1215), and mixed-type enniatins containing more than one species of amino acid (Zocher et al. 1982, *Biochemistry* 21: 43-48).

The biosynthesis of enniatins is catalyzed by enniatin synthetase, which is a large multifunctional enzyme that has all the essential functions for assembling enniatins from their primary precursors, i.e., D-2-hydroxyisovaleric acid, a branched chain L-amino acid (e.g., valine, leucine, isoleucine), S-adenosylmethionine, and ATP (Reper et al., 1995, *European Journal of Biochemistry* 230: 119-126). The precursors (D-2-hydroxyisovaleric acid and branched chain L-amino acid) are activated as thioesters. Covalently bound substrate amino acid residues are methylated under the consumption of S-adenosylmethionine. Then peptide bond formation and cyclization reactions occur.

Cyclohexadepsipeptide synthetase: The term "cyclohexadepsipeptide synthetase" is defined herein as a synthetase that catalyzes the production of a cyclohexadepsipeptide from D-2-hydroxyisovaleric acid, a branched chain L-amino acid (e.g., valine, leucine, isoleucine), S-adenosylmethionine, and ATP. For purposes of the present invention, cyclohexadepsipeptide synthetase activity is determined by measuring the production of a cyclohexadepsipeptide according to the procedure of Zocher et al., 1982, *Biochemistry* 21: 43-48. Specifically, the cyclohexadepsipeptide synthetase is incubated with 1 mM valine, 0.2 mM S-adenosylmethionine, 0.2 mM D-2-hydroxyisovaleric acid, 4 mM ATP, and 4 mM magnesium acetate in a total volume of 100 μl for 10 minutes at 37° C. in 50 mM MOPS pH 7.0. The amount of cyclohexadepsipeptide is determined as described in WO 2000/92203 based on the method of Visconti et al., 1992, *Journal of Agriculture and Food Chemistry* 40: 1076-1082. One unit of cyclohexadepsipeptide synthetase activity is defined as 1.0 μmole of cyclohexadepsipeptide produced per minute at 37° C., pH 7.0.

The level of cyclohexadepsipeptides can be determined according to the method of Visconti et al., 1992, *Journal of Agriculture and Food Chemistry* 40: 1076-1082. Specifically, one ml of *Fusarium venenatum* cell-free culture broth is extracted twice with 2.0 ml of ethyl acetate. The combined organic extracts are evaporated to dryness under a stream of nitrogen gas and redissolved in 0.5 ml hexane. One microliter samples are analyzed using a Hewlett-Packard 6890 GC/Series MSD system operating in the electron impact (EI) mode. Samples are injected on-column and separated utilizing a DB-5 capillary column (30 m×0.25 mm, 0.25 µm film) employing a temperature program with heating from 120 to 300° C. at a rate of 15° C./minute. For example, enniatins A, A1, B, B1, B2, and B3 are identified by m/z ratios for the ($M^+$+H) ion of 682, 668, 640, 654, 626, and 612, respectively.

Deficient: The term "deficient" is defined herein as a *Fusarium venenatum* mutant strain that produces no detectable activity of one or more (several) enzymes selected from the group consisting of orotidine-5'-monophosphate decarboxylase, alpha-amylase, and alkaline protease and alternatively also one or both of the enzymes trichodiene synthase and cyclohexadepsipeptide synthetase compared to the parent *Fusarium venenatum* strain when cultivated under identical conditions, or, in the alternative, produces preferably at least 25% less, more preferably at least 50% less, even more preferably at least 75% less, and most preferably at least 95% less of one or more (several) enzymes selected from the group consisting of orotidine-5'-monophosphate decarboxylase, alpha-amylase, and alkaline protease and alternatively also one or both of the enzymes trichodiene synthase and cyclohexadepsipeptide synthetase than the parent *Fusarium venenatum* strain when cultivated under identical conditions. The level of enzyme produced by a *Fusarium venenatum* mutant strain of the present invention may be determined using methods described herein or known in the art.

The mutant *Fusarium venenatum* strain produces preferably at least about 25% less, more preferably at least about 50% less, even more preferably at least about 75% less, most preferably at least about 95% less, and even most preferably no trichothecene than the corresponding parent filamentous fungal cell when cultured under identical conditions. The parent and mutant cells may be compared with regard to production of a trichothecene under conditions conducive for the production of a polypeptide of interest or under conditions conducive for the production of a trichothecene.

The mutant *Fusarium venenatum* strain produces preferably at least about 25% less, more preferably at least about 50% less, even more preferably at least about 75% less, most preferably at least about 95% less, and even most preferably no cyclohexadepsipeptide than the corresponding parent filamentous fungal cell when cultured under identical conditions. The parent and mutant cells may be compared with regard to production of a cyclohexadepsipeptide under conditions conducive for the production of a polypeptide of interest or under conditions conducive for the production of a cyclohexadepsipeptide.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having enzyme activity that is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having enzyme activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Polypeptide fragment: The term "polypeptide fragment" is defined herein as a polypeptide having one or more (several) amino acids deleted from the amino and/or carboxyl terminus of a mature polypeptide or a homologous sequence thereof; wherein the fragment has enzyme activity, e.g., orotidine-5'-monophosphate decarboxylase, alpha-amylase, alkaline protease, trichodiene synthase, or cyclohexadepsipeptide synthetase activity.

Subsequence: The term "subsequence" is defined herein as a nucleotide sequence having one or more (several) nucleotides deleted from the 5' and/or 3' end of a mature polypeptide coding sequence or a homologous sequence thereof; wherein the subsequence encodes a polypeptide fragment having enzyme activity, e.g., orotidine-5'-monophosphate decarboxylase, alpha-amylase, alkaline protease, trichodiene synthase, or cyclohexadepsipeptide synthetase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" is defined herein as an introduction, substitution, or removal of one or more nucleotides in a gene or a control sequence required for the transcription or translation thereof, or gene disruption, gene conversion, gene deletion, or random or specific mutagenesis of amyA, alpA, dps1, pyrG, tri5, or a combination thereof. The deletion of one or more (several) of the amyA, alpA, dps1, pyrG, and tri5 genes may be partial or complete. The modification results in a decrease in or elimination (inactivation) of expression of pyrG, amyA, alpA, tri5, dps1, or a combination thereof. In a preferred aspect, one or more (several) are inactivated.

DETAILED DESCRIPTION OF THE INVENTION

The present invention relates to methods of producing a polypeptide, comprising: (a) cultivating a mutant of a parent *Fusarium venenatum* strain in a medium for the production of the polypeptide, wherein the mutant strain comprises a polynucleotide encoding the polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions; and (b) recovering the polypeptide from the cultivation medium.

In one aspect, the mutant strain further comprises one or both of the genes tri5 and dps1, wherein the one or both genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

An advantage of the present invention is elimination or reduction of one or more (several) enzyme activities, which may be detrimental to the production, downstream processing, e.g., recovery, and/or application of a particular polypeptide of interest In the methods of the present invention, the parent *Fusarium venenatum* strain may be a wild-type *Fusarium venenatum* strain or a mutant thereof. It will be understood that the term "*Fusarium venenatum*" also includes varieties of *Fusarium venenatum* (see, for example, Robert A. Samsom and John I. Pitt, editors, *Integration of Modern Taxonomic Methods for Penicillium and Aspergillus Classification*, Harwood Academic Publishers, The Netherlands). In one aspect, the parent *Fusarium venenatum* strain is *Fusarium venenatum* A3/5. In another aspect, the parent *Fusarium venenatum* strain is *Fusarium venenatum* NRRL 30747. In another aspect, the parent *Fusarium venenatum* strain is *Fusarium venenatum* ATCC 20334. In another aspect, the parent *Fusarium venenatum* strain is a morphological mutant (WO 97/26330).

The enzyme-deficient *Fusarium venenatum* mutant strain may be constructed by reducing or eliminating expression of one or more (several) genes selected from the group consisting of pyrG, amyA, and alpA, and alternatively also one or both of the genes tri5 and dps1 using methods well known in the art, such as insertions, disruptions, replacements, or deletions. A portion of the gene can be modified such as the coding region or a control sequence required for expression of the coding region. Such a control sequence of a gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The *Fusarium venenatum* mutant strains may be constructed by gene deletion techniques to eliminate or reduce expression of a gene. Gene deletion techniques enable the partial or complete removal of the gene thereby eliminating their expression. In such methods, deletion of the gene(s) is accomplished by homologous recombination using a plasmid that has been constructed to contiguously contain the 5' and 3' regions flanking the gene.

The *Fusarium venenatum* mutant strains may also be constructed by introducing, substituting, and/or removing one or more (several) nucleotides in the gene or a control sequence thereof required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The *Fusarium venenatum* mutant strains may also be constructed by gene disruption techniques by inserting into a gene a disruptive nucleic acid construct comprising a nucleic acid fragment(s) homologous to the gene that will create a duplication of the region of homology and incorporate construct DNA between the duplicated regions. Such gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The *Fusarium venenatum* mutant strains may also be constructed by the process of gene conversion (see, for example, Iglesias and Trautner, 1983, *Molecular General Genetics* 189: 73-76). For example, in the gene conversion method, a nucleotide sequence corresponding to the gene(s) is mutagenized in vitro to produce a defective nucleotide sequence, which is then transformed into the parent *Fusarium venenatum* strain to produce a defective gene. By homologous recombination, the defective nucleotide sequence replaces the endogenous gene. It may be desirable that the defective nucleotide sequence also comprises a marker for selection of transformants containing the defective gene.

The *Fusarium venenatum* mutant strains may also be constructed by established anti-sense techniques using a nucleotide sequence complementary to the nucleotide sequence of the gene (Parish and Stoker, 1997, *FEMS Microbiology Letters* 154: 151-157). More specifically, expression of the gene by a *Fusarium venenatum* strain may be reduced or inactivated by introducing a nucleotide sequence complementary to the nucleotide sequence of the gene, which may be transcribed in the strain and is capable of hybridizing to the mRNA produced in the strain. Under conditions allowing the complementary anti-sense nucleotide sequence to hybridize to the mRNA, the amount of protein translated is thus reduced or eliminated.

The *Fusarium venenatum* mutant strains may also be constructed by established RNA interference (RNAi) techniques (see, for example, WO 2005/056772).

The *Fusarium venenatum* mutant strains may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of a gene.

In one aspect, the modification results in the inactivation of one or more (several) genes selected from the group consisting of pyrG, amyA, and alpA, and alternatively also one or both of the genes tri5 and dps1. In another aspect, the modification results in a decrease in expression of one or more (several) genes selected from the group consisting of pyrG, amyA, and alpA, and alternatively also one or both of the genes tri5 and dps1. In another aspect, the modification results in expression of one or more (several) genes selected from the group consisting of pyrG, amyA, and alpA, and alternatively also one or both of the genes tri5 and dps1 being decreased, inactivated, or a combination thereof.

In another aspect, the mutant comprises a modification of pyrG and amyA. In another aspect, the mutant comprises a modification of pyrG and alpA. In another aspect, the mutant comprises a modification of amyA and alpA. In another aspect, the mutant comprises a modification of tri5 and pyrG. In another aspect, the mutant comprises a modification of tri5 and amyA. In another aspect, the mutant comprises a modification of tri5 and alpA. In another aspect, the mutant comprises a modification of tri5 and dps1. In another aspect, the mutant comprises a modification of amyA and dps1. In another aspect, the mutant comprises a modification of alpA and dps1. In another aspect, the mutant comprises a modification of pyrG and dps1.

In another aspect, the mutant comprises a modification of pyrG, amyA, and alpA. In another aspect, the mutant comprises a modification of tri5, pyrG, and amyA. In another aspect, the mutant comprises a modification of tri5, pyrG, and alpA. In another aspect, the mutant comprises a modification of tri5, pyrG, and dps1. In another aspect, the mutant comprises a modification of tri5, amyA, and alpA. In another aspect, the mutant comprises a modification of tri5, amyA, and dps1. In another aspect, the mutant comprises a modification of tri5, alpA, and dps1. In another aspect, the mutant comprises a modification of amyA, alpA, and dps1. In another aspect, the mutant comprises a modification of pyrG, alpA, and dps1. In another aspect, the mutant comprises a modification of pyrG, amyA, and dps1.

In another aspect, the mutant comprises a modification of tri5, pyrG, amyA, and alpA. In another aspect, the mutant comprises a modification of tri5, pyrG, amyA, and dps1. In another aspect, the mutant comprises a modification of tri5, amyA, alpA, and dps1. In another aspect, the mutant comprises a modification of pyrG, amyA, alpA, and dps1. In another aspect, the mutant comprises a modification of tri5, pyrG, alpA, and dps1.

In another aspect, the mutant comprises a modification of pyrG, amyA, alpA, tri5, and dps1.

In one aspect, the pyrG gene comprises a nucleotide sequence encoding a polypeptide having orotidine-5'-monophosphate decarboxylase activity comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 44. In another aspect, the pyrG gene comprises a nucleotide sequence encoding a polypeptide having orotidine-5'-monophosphate decarboxylase activity comprising the amino acid sequence of SEQ ID NO: 44. In another aspect, the pyrG gene comprises a nucleotide sequence encoding a polypeptide having orotidine-5'-monophosphate decarboxylase activity consisting of the amino acid sequence of SEQ ID NO: 44.

In another aspect, the pyrG gene comprises a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 43. In another aspect, the pyrG gene comprises the nucleotide sequence of SEQ ID NO: 43. In another aspect, the pyrG gene consists of the nucleotide sequence of SEQ ID NO: 43.

In another aspect, the pyrG gene comprises a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 43 or its full-length complementary strand.

In another aspect, the orotidine-5'-monophosphate decarboxylase comprises an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 44. In another aspect, the orotidine-5'-monophosphate decarboxylase comprises the amino acid sequence of SEQ ID NO: 44. In another aspect, the orotidine-5'-monophosphate decarboxylase consists of the amino acid sequence of SEQ ID NO: 44.

In another aspect, the orotidine-5'-monophosphate decarboxylase is encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 43. In another aspect, the orotidine-5'-monophosphate decarboxylase is encoded by a polynucleotide comprising the nucleotide sequence of SEQ ID NO: 43. In another aspect, the orotidine-5'-monophosphate decarboxylase is encoded by a polynucleotide consisting of the nucleotide sequence of SEQ ID NO: 43.

In another aspect, the orotidine-5'-monophosphate decarboxylase is encoded by a polynucleotide comprising a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 43 or its full-length complementary strand.

In another aspect, the amyA gene comprises a nucleotide sequence encoding a polypeptide having alpha-amylase activity comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 52. In another aspect, the amyA gene comprises a nucleotide sequence encoding a polypeptide having alpha-amylase activity comprising the amino acid sequence of SEQ ID NO: 52. In another aspect, the amyA gene comprises a nucleotide sequence encoding a polypeptide having alpha-amylase activity consisting of the amino acid sequence of SEQ ID NO: 52.

In another aspect, the amyA gene comprises a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 51. In another aspect, the amyA gene comprises the nucleotide sequence of SEQ ID NO: 51. In another aspect, the amyA gene consists of the nucleotide sequence of SEQ ID NO: 51.

In another aspect, the amyA gene comprises a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 51 or its full-length complementary strand.

In another aspect, the alpha-amylase comprises an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 52. In another aspect, the alpha-amylase comprises the amino acid sequence of SEQ ID NO: 52. In another aspect, the alpha-amylase consists of the amino acid sequence of SEQ ID NO: 52.

In another aspect, the alpha-amylase is encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 51. In another aspect, the alpha-amylase is encoded by a polynucleotide comprising the nucleotide sequence of SEQ ID NO: 51. In another aspect, the alpha-amylase is encoded by a polynucleotide consisting of the nucleotide sequence of SEQ ID NO: 51.

In another aspect, the alpha-amylase is encoded by a polynucleotide comprising a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 51 or its full-length complementary strand.

In another aspect, the alpA gene comprises a nucleotide sequence encoding a polypeptide having alkaline protease activity comprising an amino acid sequence having a preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 84. In another aspect, the alpA gene comprises a nucleotide sequence encoding a polypeptide having alkaline protease activity comprising the amino acid sequence of SEQ ID NO: 84. In another aspect, the alpA gene comprises a nucleotide sequence encoding a polypeptide having alkaline protease activity consisting of the amino acid sequence of SEQ ID NO: 84.

In another aspect, the alpA gene comprises a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 83. In another aspect, the alpA gene comprises the nucleotide sequence of SEQ ID NO: 83. In another aspect, the alpA gene consists of the nucleotide sequence of SEQ ID NO: 83.

In another aspect, the alpA gene comprises a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 83 or its full-length complementary strand.

In another aspect, the alkaline protease comprises an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 84. In another aspect, the alpha-amylase comprises the amino acid sequence of SEQ ID NO: 84. In another aspect, the alpha-amylase consists of the amino acid sequence of SEQ ID NO: 84.

In another aspect, the alkaline protease is encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 83. In another aspect, the alkaline protease is encoded by a polynucleotide comprising the nucleotide sequence of SEQ ID NO: 83. In another aspect, the alkaline protease is encoded by a polynucleotide consisting of the nucleotide sequence of SEQ ID NO: 83.

In another aspect, the alkaline protease is encoded by a polynucleotide comprising a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 83 or its full-length complementary strand.

In another aspect, the tri5 gene comprises a nucleotide sequence encoding a polypeptide having trichodiene synthase activity comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 20. In another aspect, the tri5 gene comprises a nucleotide sequence encoding a polypeptide having trichodiene synthase activity comprising the amino acid sequence of SEQ ID NO: 20. In another aspect, the tri5 gene comprises a nucleotide sequence encoding a polypeptide having trichodiene synthase activity consisting of the amino acid sequence of SEQ ID NO: 20.

In another aspect, the tri5 gene comprises a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 19. In another aspect, the tri5 gene comprises the nucleotide sequence of SEQ ID NO: 19. In another aspect, the tri5 gene consists of the nucleotide sequence of SEQ ID NO: 19.

In another aspect, the tri5 gene comprises a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 19 or its full-length complementary strand.

In another aspect, the trichodiene synthase comprises an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 20. In another aspect, the trichodiene synthase comprises the amino acid sequence of SEQ ID NO: 20. In another aspect, the trichodiene synthase consists of the amino acid sequence of SEQ ID NO: 20.

In another aspect, the trichodiene synthase is encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 19. In another aspect, the trichodiene synthase is encoded by a polynucleotide comprising the nucleotide sequence of SEQ ID NO: 19. In another aspect, the trichodiene synthase is encoded by a polynucleotide consisting of the nucleotide sequence of SEQ ID NO: 19.

In another aspect, the trichodiene synthase is encoded by a polynucleotide comprising a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 19 or its full-length complementary strand.

In another aspect, the dps1 gene comprises a nucleotide sequence encoding a polypeptide having cyclohexadepsipeptide synthetase activity comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 94. In another aspect, the dps1 gene comprises a nucleotide sequence encoding a polypeptide having cyclohexadepsipeptide synthetase activity comprising the amino acid sequence of SEQ ID NO: 94. In another aspect, the dps1 gene comprises a nucleotide sequence encoding a polypeptide having cyclohexadepsipeptide synthetase activity consisting of the amino acid sequence of SEQ ID NO: 94.

In another aspect, the dps1 gene comprises a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 93. In another aspect, the dps1 gene comprises the nucleotide sequence of SEQ ID NO: 93. In another aspect, the dps1 gene consists of the nucleotide sequence of SEQ ID NO: 93.

In another aspect, the dps1 gene comprises a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 93 or its full-length complementary strand.

In another aspect, the cyclohexadepsipeptide synthetase comprises an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the amino acid sequence of SEQ ID NO: 94. In another aspect, the cyclohexadepsipeptide synthetase comprises the amino acid sequence of SEQ ID NO: 94. In another aspect, the cyclohexadepsipeptide synthetase consists of the amino acid sequence of SEQ ID NO: 94.

In another aspect, the cyclohexadepsipeptide synthetase is encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity to the nucleotide sequence of SEQ ID NO: 93. In another aspect, the cyclohexadepsipeptide synthetase is encoded by a polynucleotide comprising the nucleotide sequence of SEQ ID NO: 93. In another aspect, the cyclohexadepsipeptide synthetase is encoded by a polynucleotide consisting of the nucleotide sequence of SEQ ID NO: 93.

In another aspect, the cyclohexadepsipeptide synthetase is encoded by a polynucleotide comprising a nucleotide sequence that hybridizes under preferably very low stringency conditions, more preferably low stringency conditions, more preferably medium stringency conditions, more preferably medium-high stringency conditions, even more preferably high stringency conditions, and most preferably very high stringency conditions with the nucleotide sequence of SEQ ID NO: 93 or its full-length complementary strand.

The nucleotide sequences disclosed herein or subsequences thereof, as well as the amino acid sequences thereof or fragments thereof, may be used to design nucleic acid probes to identify and clone homologous DNA of the genes described above from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA that hybridizes with the probes described above. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with the nucleotide sequences disclosed herein or subsequences thereof, the carrier material is used in a Southern blot. For purposes of the present invention, hybridization indicates that the nucleic acid sequence hybridizes to a labeled nucleic acid probe corresponding to the nucleotide sequences disclosed herein, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

A nucleotide sequence homologous or complementary to a gene described herein may be used from other microbial sources to modify the corresponding gene in the *Fusarium venenatum* strain of choice.

In another aspect, the modification of a gene in the *Fusarium venenatum* mutant strain is unmarked with a selectable marker.

Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the *Fusarium venenatum* mutant strain. The modification of a gene may be introduced into the parent strain at any step in the construction of the strain for the production of a polypeptide of interest. It is preferred that the *Fusarium venenatum* mutant strain has already been made enzyme-deficient prior to such a construction.

In a further aspect of the present invention, the mutants of *Fusarium venenatum* strains may contain additional modifications, e.g., deletions or disruptions, of other genes, which may encode substances detrimental to the production, recovery, or application of a polypeptide of interest.

In one aspect, the *Fusarium venenatum* strain further comprises a modification, e.g., disruption or deletion, of one or more (several) genes encoding a proteolytic activity. In another aspect, the proteolytic activity is selected from the group consisting of an aminopeptidase, dipeptidylaminopeptidase, tripeptidylaminopeptidase, carboxypeptidase, aspergillopepsin, serine protease, metalloprotease, cysteine protease, and vacuolar protease.

In another aspect, the *Fusarium venenatum* strain further comprises a modification, e.g., disruption or deletion, of one or more (several) additional genes encoding an enzyme selected from the group consisting of a carbohydrase, carboxypeptidase, catalase, cellulase, chitinase, cutinase, cyclodextrin glycosyltransferase, deoxyribonuclease, esterase, galactosidase, beta-galactosidase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, ribonuclease, transferase, alpha-1,6-transglucosidase, alpha-1,6-transglucosidase, transglutaminase, and xylanase.

In the methods of the present invention, the *Fusarium venenatum* mutant strain preferably produces at least the same amount of the polypeptide of interest as the corresponding parent *Fusarium venenatum* strain when cultured under identical production conditions. In another aspect, the mutant strain produces at least 25% more, preferably at least 50% more, more preferably at least 75% more, and most preferably at least 100% more of the polypeptide than the corresponding parent *Fusarium venenatum* strain when cultured under identical production conditions.

The *Fusarium venenatum* mutant strains are cultivated in a nutrient medium for production of the polypeptide of interest using methods known in the art. For example, the strain may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium. If the polypeptide is not secreted, it may be obtained from cell lysates.

The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of an enzyme. Procedures for determining enzyme activity are known in the art for many enzymes (see, for example, D. Schomburg and M. Salzmann (eds.), *Enzyme Handbook*, Springer-Verlag, New York, 1990).

The resulting polypeptide may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

The polypeptide of interest may be any polypeptide native or foreign (heterologous) to the *Fusarium venenatum* strain. The polypeptide may be encoded by a single gene or two or more genes. The term "polynucleotide encoding the polypeptide" will be understood to encompass one or more (several) genes involved in the production of the polypeptide. The term "heterologous polypeptide" is defined herein as a polypeptide that is not native to the host strain; a native polypeptide in which structural modifications have been made to alter the native polypeptide, e.g., the protein sequence of a native polypeptide; or a native polypeptide whose expression is quantitatively altered as a result of a manipulation of the polynucleotide or host strain by recombinant DNA techniques, e.g., a stronger promoter. Thus, the present invention also encompasses, within the scope of the term "heterologous polypeptides," such recombinant production of native polypeptides, to the extent that such expression involves the use of genetic elements not native to the *Fusarium venenatum* strain, or use of native elements that have been manipulated to function in a manner that do not normally occur in the host strain. In one aspect, the polypeptide is a native polypeptide to the *Fusarium venenatum* strain. In another aspect, the polypeptide is a heterologous polypeptide to the *Fusarium venenatum* strain.

The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include fusion polypeptides, which comprise a combination of partial or complete polypeptide sequences obtained from at least two different polypeptides wherein one or more (several) may be heterologous to the *Fusarium venenatum* strain. Polypeptides further include naturally occurring allelic and engineered variations of the above-mentioned polypeptides and hybrid polypeptides.

Preferably, the polypeptide is an antibody, antigen, antimicrobial peptide, enzyme, growth factor, hormone, immunodilator, neurotransmitter, receptor, reporter protein, structural protein, or transcription factor.

In one aspect, the polypeptide is an oxidoreductase, transferase, hydrolase, lyase, isomerase, or ligase. In another aspect, the polypeptide is an aminopeptidase, alpha-amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another aspect, the polypeptide is an albumin, collagen, tropoelastin, elastin, or gelatin.

In the methods of the present invention, the mutant of the *Fusarium venenatum* strain is a recombinant strain, comprising a polynucleotide encoding a heterologous polypeptide, which is advantageously used in the recombinant production of the polypeptide. The strain is preferably transformed with a vector comprising the polynucleotide encoding the heterologous polypeptide followed by integration of the vector into the chromosome. "Transformation" means introducing a vector comprising the polynucleotide into a host strain so that the vector is maintained as a chromosomal integrant or as a self-replicating extra-chromosomal vector. Integration is generally considered to be an advantage as the polynucleotide is more likely to be stably maintained in the strain. Integration of the vector into the chromosome can occur by homologous recombination, non-homologous recombination, or transposition.

The polynucleotide encoding a heterologous polypeptide may be obtained from any prokaryotic, eukaryotic, or other source, e.g., archaeabacteria. For purposes of the present invention, the term "obtained from" as used herein in connection with a given source shall mean that the polypeptide is produced by the source or by a strain in which a gene from the source has been inserted.

In the methods of the present invention, a mutant *Fusarium venenatum* strain of the present invention may also be used for the recombinant production of a polypeptide that is native to the *Fusarium venenatum* strain. The native polypeptide may be produced by recombinant means by, for example, placing a gene encoding the polypeptide under the control of a different promoter to enhance expression of the substance, expediting its export outside the strain by use of, for example, a signal sequence, or increasing the copy number of a gene encoding the polypeptide normally produced by the *Fusarium venenatum* strain.

The techniques used to isolate or clone a polynucleotide encoding a polypeptide of interest are known in the art and include isolation from genomic DNA, preparation from cDNA, or a combination thereof. The cloning of such a polynucleotide from such genomic DNA can be effected, e.g., by using the well known polymerase chain reaction (PCR). See, for example, Innis et al., 1990, PCR Protocols: A Guide to Methods and Application, Academic Press, New York. The cloning procedures may involve excision and isolation of a desired nucleic acid fragment comprising the polynucleotide encoding the polypeptide, insertion of the fragment into a vector molecule, and incorporation of the recombinant vector into a mutant *Fusarium venenatum* strain of the present invention where multiple copies or clones of the polynucleotide will be replicated. The polynucleotide may be of genomic, cDNA, RNA, semisynthetic, synthetic origin, or any combinations thereof.

In the methods of the present invention, the polypeptide may also be a fused polypeptide or cleavable fusion polypeptide in which a polypeptide is fused at the N-terminus or the C-terminus of another polypeptide or fragment thereof. A fused polypeptide is produced by fusing a nucleotide sequence (or a portion thereof) encoding a polypeptide to another nucleotide sequence (or a portion thereof) encoding another polypeptide. Techniques for producing fusion polypeptides are known in the art, and include ligating the coding sequences encoding the polypeptides so that they are in frame and that expression of the fused polypeptide is under control of the same promoter(s) and terminator.

An isolated polynucleotide encoding a heterologous polypeptide may be manipulated in a variety of ways to provide for expression of the polypeptide in a mutant *Fusarium venenatum* strain of the present invention. Manipulation of the polynucleotide's sequence prior to its insertion into a vector may be desirable or necessary depending on the expression vector. The techniques for modifying polynucleotide sequences utilizing recombinant DNA methods are well known in the art.

A nucleic acid construct comprising a polynucleotide encoding a polypeptide may be operably linked to one or more (several) control sequences capable of directing expression of the coding sequence in a mutant *Fusarium venenatum* strain of the present invention under conditions compatible with the control sequences.

The control sequence may be an appropriate promoter sequence, a nucleotide sequence that is recognized by a mutant *Fusarium venenatum* strain of the present invention for expression of the polynucleotide encoding the polypeptide. The promoter sequence contains transcriptional control sequences that mediate expression of the polypeptide. The promoter may be any nucleotide sequence that shows transcriptional activity in the mutant *Fusarium venenatum* strain, including mutant, truncated, and hybrid promoters, and may be obtained from genes encoding extracellular or intracellular polypeptides either native or heterologous (foreign) to the mutant *Fusarium venenatum* strain.

Examples of suitable promoters for directing the transcription of the nucleic acid constructs in the methods of the present invention are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The control sequence may also be a suitable transcription terminator sequence, a sequence recognized by a mutant *Fusarium venenatum* strain of the present invention to terminate transcription. The terminator sequence is operably linked to the 3' terminus of the nucleotide sequence encoding the heterologous polypeptide. Any terminator that is functional in a *Fusarium venenatum* strain may be used in the present invention.

Preferred terminators are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA that is important for translation by a mutant *Fusarium venenatum* strain of the present invention. The leader sequence is operably linked to the 5' terminus of the nucleotide sequence encoding the heterologous polypeptide. Any leader sequence that is functional in the mutant *Fusarium venenatum* strain may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleotide sequence and, when transcribed, is recognized by the mutant *Fusarium venenatum* strain as a signal to add polyadenosine residues to transcribed mRNA. Any polyadenylation sequence that is functional in the mutant *Fusarium venenatum* strain may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of the mutant *Fusarium venenatum* strain, i.e., secreted into a culture medium, may be used in the present invention.

Effective signal peptide coding regions for the mutant *Fusarium venenatum* strains are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from genes for *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

The nucleic acid constructs may also comprise one or more (several) polynucleotides that encode one or more (several) factors that are advantageous for directing expression of the heterologous polypeptide, e.g., a transcriptional activator (e.g., a trans-acting factor), a chaperone, and a processing protease. Any factor that is functional in the mutant *Fusarium venenatum* strain may be used in the present invention. The nucleic acids encoding one or more (several) of these factors are not necessarily in tandem with the nucleotide sequence encoding the heterologous polypeptide.

It may also be desirable to add regulatory or control sequences that allow regulation of expression of the polypeptide relative to the growth of the mutant *Fusarium venenatum* strain. Examples of regulatory systems are those that cause expression of the gene to be turned on or off in response to a chemical or physical stimulus, including the presence of a regulatory compound. Regulatory systems in filamentous fungi such as the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

In the methods of the present invention, a recombinant expression vector comprising a nucleotide sequence, a promoter, and transcriptional and translational stop signals may be used for the recombinant production of a polypeptide of interest. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on its compatibility with the mutant *Fusarium venenatum* strain into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the mutant *Fusarium venenatum* strain, is integrated into the genome and replicated together with the chromosome(s) into which it has been integrated. Furthermore, a single vector or plasmid or two or more vectors or plasmids that together contain the total DNA to be introduced into the genome of the mutant *Fusarium venenatum* strain, or a transposon, may be used.

The vector preferably contains one or more (several) selectable markers that permit easy selection of transformed mutant *Fusarium venenatum* strains. A selectable marker is a gene the product of which provides for biocide or viral resistance, resistance to heavy metals, prototrophy to auxotrophs, and the like.

Examples of selectable markers for use in the mutant *Fusarium venenatum* strain include, but are not limited to, amdS (acetamidase), argB (ornithine carbamoyltransferase), bar (phosphinothricin acetyltransferase), hpt (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in the mutant *Fusarium venenatum* strain are the amdS gene of *Aspergillus nidulans* and the bar gene of *Streptomyces hygroscopicus*.

The vectors preferably contain an element(s) that permits integration of the vector into the host cell's genome or autonomous replication of the vector in the cell independent of the genome.

For integration into the genome of the mutant *Fusarium venenatum* strain, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the mutant *Fusarium venenatum* strain at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the mutant *Fusarium venenatum* strain. Furthermore, the integrational elements may be non-encoding or encoding nucleotide sequences. On the other hand, the vector may be integrated into the genome of the mutant *Fusarium venenatum* strain by non-homologous recombination.

For autonomous replication, the vector may further comprise an origin of replication enabling the vector to replicate autonomously in the mutant *Fusarium venenatum* strain. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in the mutant *Fusarium venenatum* strain are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

The procedures used to ligate the elements described herein to construct the recombinant expression vectors are well known to one skilled in the art (see, e.g., J. Sambrook, E. F. Fritsch, and T. Maniatus, 1989, *Molecular Cloning, A Laboratory Manual*, 2d edition, Cold Spring Harbor, New York).

A vector comprising the nucleotide sequence can be introduced, e.g., by transformation, into the mutant *Fusarium venenatum* strain so that the vector is maintained as a chromosomal integrant or as a self-replicating extra-chromosomal vector. Integration is generally considered to be an advantage as the nucleotide sequence is more likely to be stably maintained in the strain. Integration of the vector into the chromosome occurs by homologous recombination, non-homologous recombination, or transposition.

The introduction of an expression vector into the mutant *Fusarium venenatum* strain may involve a process consisting of protoplast formation, transformation of the protoplasts, and regeneration of the strain wall in a manner known per se. Suitable procedures for transformation of *Fusarium venenatum* strains are described in Malardier et al., 1989, *Gene* 78: 147-156, and WO 96/00787.

The present invention also relates to methods of obtaining mutants of a parent *Fusarium venenatum* strain, comprising: (a) modifying one or more (several) genes selected from the group consisting of pyrG, amyA, and alpA; and (b) identifying a mutant strain from step (a) wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

In one aspect, the methods of obtaining mutants of a parent *Fusarium venenatum* strain further comprise modifying one or both of the genes tri5 and dps1 rendering the mutant strain deficient in the production of one or both enzymes trichodiene synthase and cyclohexadepsipeptide synthetase, respectively, compared to the parent *Fusarium venenatum* strain when cultivated under identical conditions.

The present invention also relates to mutants of a parent *Fusarium venenatum* strain, comprising a polynucleotide encoding a polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

In one aspect, the mutants of a parent *Fusarium venenatum* strain further comprise one or both of the genes tri5 and dps1, wherein the one or both genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

The present invention is further described by the following examples that should not be construed as limiting the scope of the invention.

EXAMPLES

Materials

Chemicals used as buffers and substrates were commercial products of at least reagent grade. All primers and oligonucleotides were supplied by MWG Biotech, Inc., High Point, N.C., USA.

Fungal Strain

*Fusarium* strain A3/5, now reclassified as *Fusarium venenatum* (Yoder and Christianson, 1998, *Fungal Genetics and Biology* 23: 62-80; O'Donnell et al., 1998, *Fungal Genetics and Biology* 23: 57-67), was obtained from Dr. Anthony Trinci, University of Manchester, Manchester, England. Deposits of this strain can be obtained from the American Type Culture Collection, Manassas, Va., USA as *Fusarium* strain ATCC 20334 or the Agricultural Research Service Patent Culture Collection (NRRL), Northern Regional Research Center, 1815 University Street, Peoria, Ill., USA as *Fusarium* strain NRRL 30747.

Media and Solutions

LB plates were composed per liter of 10 g of tryptone, 5 g of yeast extract, 5 g of NaCl, and 15 g of Bacto agar.

NZY top agarose was composed per liter of 5 g of NaCl, 5 g of yeast extract, 10 g of NZ amine, 2 g of $MgSO_4$, and 7 g of agarose.

M400 medium was composed per liter of 50 g of maltodextrin, 2 g of $MgSO_4.7H_2O$, 2 g of $KH_2PO_4$, 4 g of citric acid, 8 g of yeast extract, 2 g of urea, 0.5 g of $CaCl_2$, and 0.5 ml of AMG trace metals solution, pH 6.0.

AMG trace metals solution were composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

2XYT medium was composed per liter of 16 g of tryptone, 10 g of yeast extract, 5 g of NaCl, and 5 g of Bacto agar.

YP medium was composed per liter of 10 g of yeast extract and 20 g of Bacto peptone.

$YPG_{5\%}$ medium was composed per liter of 10 g of yeast extract, 20 g of Bacto peptone, and 50 g of glucose.

RA medium was composed per liter of 50 g of succinic acid, 12.1 g of $NaNO_3$, 1 g of glucose, and 20 ml of 50× Vogels salts solution (No C, No $NaNO_3$).

RA+uridine medium was composed per liter of 50 g of succinic acid, 12.1 g of $NaNO_3$, 1 g of glucose, and 20 ml of 50× Vogels salts solution (No C, No $NaNO_3$). After filter sterilization of the RA medium, filter sterilized uridine was added to a final concentration of 10 mM.

RA+BASTA™ medium was composed per liter of 50 g of succinic acid, 12.1 g of $NaNO_3$, 1 g of glucose, and 20 ml of 50× Vogels salts solution (No C, No $NaNO_3$). After filter sterilization of the RA medium, filter-sterilized BASTA™ (glufosinate, Hoechst Schering AgrEvo, Frankfurt, Germany) was added to a final concentration of 6 mg/ml using a working stock solution of 250 mg/ml.

50× Vogels salts solution (No C, No $NaNO_3$) was composed of per liter of 250 g of $KH_2PO_4$, 10 g of $MgSO_4.7H_2O$, 5 g of $CaCl_2.2H_2O$, 2.5 ml of biotin solution, and 5 ml of Vogels trace elements solution.

Biotin stock solution was composed of 5 mg of biotin in 100 ml of 50% ethanol.

Vogels trace elements solution was composed per 100 ml of 5 g of citric acid, 5 g of $ZnSO_4.7H_2O$, 1 g of $Fe(NH_4)_2(SO_4)_2.6H_2O$, 0.25 g of $CuSO_4.5H_2O$, 0.05 g of $MnSO_4.H_2O$, 0.05 g of $H_3BO_3$, and 0.05 g of $Na_2MoO_4.2H_2O$.

$VNO_3RLMT$ plates were composed per liter of 20 ml of 50× Vogels salts solution (25 mM $NaNO_3$), 273.33 g of sucrose, and 15 g of LMT agarose (Sigma, St. Louis, Mo., USA).

50× Vogels salts solution (25 mM $NaNO_3$) was composed per liter of 125 g of sodium citrate, 250 g of $KH_2PO_4$, 106.25 g of $NaNO_3$, 10 g of $MgSO_4.7H_2O$, 5 g of $CaCl_2.2H_2O$, 2.5 ml of biotin stock solution, and 5 ml of Vogels trace elements solution.

$VNO_3RLMT$-BASTA™ plates were composed per liter of 20 ml of 50× Vogels salts solution (25 mM $NaNO_3$), 273.33 g of sucrose, and 15 g of LMT agarose. After autoclaving and cooling BASTA™ was added to a final concentration of 6 mg/ml.

STC was composed of 0.8 M sorbitol, 25 or 50 mM Tris pH 8, and 50 mM $CaCl_2$.

SPTC was composed of 40% PEG 4000, 0.8 M sorbitol, 25 or 50 mM Tris pH 8, and 50 mM $CaCl_2$.

SY50 medium (pH 6.0) was composed per liter of 50 g of sucrose, 2.0 g of $MgSO_4.7H_2O$, 10 g of $KH_2PO_4$, 2.0 g of $K_2SO_4$, 2.0 g of citric acid, 10 g of yeast extract, 2.0 g of urea, 0.5 g of $CaCl_2.2H_2O$, and 5 ml of 200×AMG trace metals solution (no nickel).

200×AMG trace metals solution (no nickel) was composed per liter of 3.0 g of citric acid, 14.3 g of $ZnSO_4.7H_2O$, 2.5 g of $CuSO_4.5H_2O$, 13.8 g of $FeSO_4.7H_2O$, and 8.5 g of $MnSO_4.H_2O$.

20×SSC was composed of 0.3 M sodium citrate pH 7 and 3 M sodium chloride.

DNA Sequencing

DNA sequencing was conducted with an ABI PRIZM® 3700 DNA Analyzer (Applied Biosystems, Inc., Foster City, Calif., USA).

Example 1

*Fusarium venenatum* Transformation Procedure

One hundred micrograms of each of the deletion cassettes described in the following examples were digested with either Bst Z171/Bam HI (Example 11) or Not I (Examples 14, 16, 28 and 30). Each digestion reaction was purified by 1% agarose gel electrophoresis in TAE buffer and a DNA band was extracted using a QIAQUICK® Gel Extraction Kit. The resulting purified DNA was concentrated in a 1.5 ml microfuge tube by ethanol precipitation with the addition of 10% reaction volume of 3 M sodium acetate pH 5 followed by 2.5 volumes of ice cold ethanol (94%) and incubation on ice for 20 minutes. The tube was then centrifuged at 15,000×g for 10 minutes in an EPPENDORF® 5424 benchtop centrifuge (Eppendorf, Hamburg, Germany). The supernatant was discarded and the pellet washed with 1 ml of ice cold 70% ethanol and centrifuged at 15,000×g for 5 minutes. The supernatant was discarded and the pellet allowed to air dry. The pellet was then resuspended in 70 µl of 10 mM Tris pH 8 buffer. The concentration of the resulting DNA containing solution was determined using a NANODROP® 1000 spectrophotometer (ThermoFischer Scientific, Waltham, Mass., USA).

Protoplasts of the appropriate recipient strain were generated by the following method. Spores were first obtained by inoculating 500 ml of RA medium (Example 11) or RA medium supplemented with 10 mM uridine (Examples 14, 16, 28, and 30) in a 2.8 L Fernbach flask with 15×1 $cm^2$ agar plugs of a 7-day old culture containing $VNO_3RLMT$ medium and incubating the flask for 36 hours at 28° C. with shaking at 150 rpm. The spore culture was filtered through sterile MIRACLOTH™ and the spores captured on a MILLIPORE® STERICUP® 0.2 µm filter unit (Millipore, Billerica, Mass., USA). The spores were washed with 200 ml of sterile glass distilled water and resuspended in 10 ml of sterile glass distilled water.

One ml of the spore solution was used to inoculate 100 ml of YP medium supplemented with 5% glucose (Example 11) or YP medium supplemented with 5% glucose and 10 mM uridine (Examples 14, 16, 28, and 30). The inoculated medium was incubated for 16 hours at 17° C. with shaking at 150 rpm. Cultures were filtered through MIRACLOTH™ to collect mycelia, which were transferred to a 50 ml polypropylene tube using a sterile spatula. The mycelia were resuspended in 20 ml of protoplasting solution, which contained 5 mg of NOVOZYME™ 234 per ml and 5 mg of GLUCANEX™ (both from Novozymes A/S, Bagsvaerd, Denmark) in 1 M MgSO$_4$ per ml and transferred to 50 ml polypropylene tubes. The tubes were incubated at 29.5° C. with shaking at 90 rpm for one hour after which 30 ml of 1 M sorbitol were added. Then the tubes were centrifuged at 800×g for 10 minutes in a Sorvall RT 6000B swinging-bucket centrifuge (ThermoFischer Scientific, Waltham, Mass., USA). The supernatants were discarded and the protoplast pellets were washed twice with 30 ml of 1 M sorbitol. The tubes were centrifuged at 800×g for 5 minutes and the supernatants discarded. The protoplasts were resuspended in a solution of filter-sterilized 9:1:0.1 (v/v) STC:SPTC:DMSO at a concentration of 5×10$^7$ per ml and frozen overnight at −80° C. at controlled rate freezing using a NALGENE™ Cryo 1° C. Freezing Container (ThermoFischer Scientific, Waltham, Mass., USA).

Transformation was accomplished by thawing the protoplasts on ice and adding 200 μl of the protoplasts to each of four 14 ml tubes. Five μg of DNA (in less than 10 μl) were added to the first three and no DNA was added to the fourth. Then 750 μl of SPTC were added to each tube and the tubes were inverted gently 6 times. The tubes were incubated at room temperature for 30 minutes and 6 ml of STC were added to each tube. Each transformation was divided into three parts and added to 150 mm diameter plates containing VNO$_3$RLMT medium supplemented with 125 μg of hygromycin per ml (Example 11) or VNO$_3$RLMT medium supplemented with 125 μg of hygromycin per ml and 10 mM uridine (Examples 14, 16, 28, and 30) and incubated at room temperature for 7 days.

Example 2

Southern Analyses

Fungal biomass was produced by inoculating 25 ml of M400 medium (Example 11) or M400 medium supplemented with 10 mM uridine (Examples 14, 16, 28 and 30) with four 1 cm agar plugs from 7 day old transformants generated as described in Examples 1 and 11. The cultures were incubated for 3 days at 28° C. with shaking at 150 rpm. Agar plugs were removed and the cultures were filtered through MIRACLOTH™. Harvested biomass was frozen with liquid nitrogen and the mycelia were ground using a mortar and pestle.

Genomic DNA was isolated using a DNEASY® Plant Maxi Kit (QIAGEN, Valencia, Calif., USA) according to the manufacturer's instructions except the lytic incubation period at 65° C. was extended to 1.5 hours from 10 minutes.

Two μg of genomic DNA were digested with the indicated restriction endonucleases in a 50 μl reaction volume at 37° C. for 22 hours. The digestions were subjected to 1.0% agarose gel electrophoresis in TAE buffer. The DNA was fragmented in the gel by treating with 0.25 M HCl, denatured with 1.5 M NaCl-0.5 M NaOH, neutralized with 1.5 M NaCl-1 M Tris pH 8, and then transferred in 20×SSC to a NYTRAN® Supercharge nylon membrane using a TURBOBLOTTER™ Kit (both from Whatman, Kent, UK). The DNA was UV cross-linked to the membrane using a UV STRATALINKER™ (Stratagene, La Jolla, Calif., USA) and pre-hybridized for 1 hour at 42° C. in 20 ml of DIG Easy Hyb (Roche Diagnostics Corporation, Indianapolis, Ind., USA).

Probes were generated using a PCR Dig Probe Synthesis Kit (Roche Diagnostics Corporation, Indianapolis, Ind., USA) according to the manufacturer's instructions. The probes were purified by 1.2% agarose gel electrophoresis in TAE buffer and the bands corresponding to the probes were excised and agarose-extracted using a MINELUTE® Gel Extraction Kit (QIAGEN Inc., Valencia, Calif., USA). The probes were boiled for 5 minutes and each added to 10 ml of DIG Easy Hyb to produce the hybridization solution. Hybridization was performed at 42° C. for 15-17 hours. The membranes were then washed under high stringency conditions in 2×SSC plus 0.1% SDS for 5 minutes at room temperature followed by two washes in 0.1×SSC plus 0.1% SDS for 15 minutes each at 65° C. The probe-target hybrids were detected by chemiluminescent assay (Roche Diagnostics, Indianapolis, Ind., USA) according to the manufacturer's instructions.

Example 3

Construction of Plasmid pDM156.2 Harboring the Genomic DNA Fragment Incorporating the *Fusarium venenatum* Orotidine-5'-Monophosphate Decarboxylase (pyrG) Gene A probe of a *Neurospora crassa* orotidine-5'-monophosphate decarboxylase (pyr-4) gene (SEQ ID NO: 1 for the DNA sequence and SEQ ID NO: 2 for the deduced amino acid sequence) was prepared by PCR incorporating digoxigenin-labeled deoxyuridine-triphosphate (dUTP) and the primers described below.

```
Primer (sense):
                                 (SEQ ID NO: 3)
5'-GTCAGGAAACGCAGCCACAC-3'

Primer (anti-sense):
                                 (SEQ ID NO: 4)
5'-AGGCAGCCCTTGGACGACAT-3'
```

Plasmid pFB6 (Buxton et al, 1983, *Molecular and General Genetics* 190: 403-405) was digested with Hind III and the digestion purified by 1% agarose gel electrophoresis using TAE buffer. A 1.1 kb pyr-4 fragment was excised and agarose-extracted using a QIAQUICK® Gel Extraction Kit according to the manufacturer's suggested protocols.

The amplification reaction (50 μl) was composed of 1×Taq DNA Polymerase Buffer (New England Biolabs Inc., Ipswich, Mass., USA), 5 μl of PCR DIG Labeling Mix (Boehringer Mannheim, Manheim, Germany), 10 ng of the 1.1 kb Hind III pyr-4 fragment, 10 μmol of the sense primer, 10 μmol of the anti-sense primer, and 1 unit of Taq DNA polymerase New England Biolabs Inc., Ipswich, Mass., USA). The reaction was incubated in a ROBOCYCLER® (Stratagene, La Jolla, Calif., USA) programmed for 1 cycle at 95° C. for 3 minutes followed by 35 cycles each at 95° C. for 30 seconds, 55° C. for 1 minute, and 72° C. for 1 minute. A final extension was performed for 5 minutes at 72° C.

The amplification reaction products were purified by 1% agarose gel electrophoresis using TAE buffer. A digoxigenin (DIG) labeled probe of approximately 0.78 kb was excised from the gel and agarose-extracted using a QIAQUICK® Gel Extraction Kit.

A genomic DNA library of *Fusarium venenatum* strain A3/5 was generated and cloned into lambda vector EMBL4 as described in WO 99/60137.

The DIG-labeled probe was used to screen the genomic library of *Fusarium venenatum* A3/5 DNA cloned into lambda vector EMBL4. Lambda phages were plated with *E. coli* K802 cells (New England Biolabs, Ipswich, Mass., USA) onto LB plates with NZY top agarose. Plaque lifts were made to HYBOND™ N nylon membranes (Amersham Biosciences, Buckinghamshire, UK) using the technique of Sambrook et al. (*Molecular Cloning, A Laboratory Manual, Second Edition*; J. Sambrook, E. F. Fritsch, and T. Maniatis; Cold Spring Harbor Laboratory Press, 1989). DNA was bound to the membranes by UV cross-linking using a UV STRATALINKER™. Filters were then hybridized with the 0.78 kb DIG-labeled *N. crassa* pyr-4 probe. Hybridization and detection of pyrG clones were performed according to the GENIUS™ System User's Guide (Boehringer Hammheim, Manheim, Germany) at 42° C. with a hybridization solution composed of 5×SSC, 35% formamide, 0.1% L-lauroylsarcosine, 0.02% SDS, and 1% blocking reagent (Boehringer Hammheim, Manheim, Germany). The concentration of DIG-labeled probe used was 2.5 ng per ml of the hybridization solution. Hybridizing DNA was immuno-detected with an alkaline-phosphatase-conjugated anti-digoxigenin antibody (Boehringer Hammheim, Manheim, Germany) and visualized with Lumiphos 530, a chemiluminescent substrate (Boehringer Hammheim, Manheim, Germany). DNA preparations were made from putative positive lambda clones using a Lambda Midi Kit (QIAGEN Inc., Valencia, Calif., USA).

Lambda DNA from a clone identified above was digested with Eco RI and subjected to 1% agarose gel electrophoresis in TAE buffer. A 3.9 kb fragment was excised and agarose-extracted using a QIAEX Gel Extraction Kit (QIAGEN Inc., Valencia, Calif.). The fragment was then cloned into the Eco RI site of pUC18 (Viera and Messing, 1987, Methods in Enzymology 153: 3-11) and ONE SHOT® TOP10 competent cells (Invitrogen, Carlsbad, Calif., USA) were transformed with 2 μl of the cloning reaction. Plasmid DNA from eight of the resulting transformants was analyzed by DNA sequencing. One clone with the desired sequence was selected and designated pDM156.2 (FIG. 1). The pyrG fragment harbored the entire coding region plus 1.3 kb of the promoter and 1.5 kb of the terminator.

Example 4

Generation of pEmY21

An *E. coli* hygromycin phosphotransferase (hpt) gene (SEQ ID NO: 5 for the DNA sequence and SEQ ID NO: 6 for the deduced amino acid sequence) was amplified from plasmid pPHTI (Cummings et al., 1999, *Current Genetics* 36: 371-382) using the following primers:

```
Forward primer:
                                    (SEQ ID NO: 7)
5'-GGGttcgaaTTCATTTAAACGGCT-3'

Reverse primer:
                                    (SEQ ID NO: 8)
5'-GGGagcgctCAATATTCATCTCTC-3'
```

The restriction enzyme sites Bst BI (forward primer) and Eco 47111 (reverse primer) were engineered into the primers, represented by the underlined sequence, for cloning.

The PCR reaction (to amplify the hpt gene) was composed of 1× ThermoPol reaction buffer, 200 μM dNTPs, 50 μmol of the forward and reverse primers, 100 μg of pPHT1, 1 unit of Vent® DNA polymerase (New England Biolabs Inc., Ipswich, Mass. USA), and sterile distilled water in a total volume of 100 μl. The amplification reaction was performed using a ROBOCYCLER® programmed for 1 cycle at 95° C. for 2 minutes; 25 cycles each at 95° C. for 1 minute, 51° C. for 1 minute, and 72° C. for 2 minutes; and 1 cycle at 72° C. for 7 minutes.

PCR products were separated by 1% agarose gel electrophoresis in TAE buffer. A 1.8 kb fragment was excised from the gel and agarose extracted using a QIAQUICK® Gel Extraction Kit. The gel purified fragment was then cloned into pCR®-BluntII-TOPO® (Invitrogen, Carlsbad, Calif., USA) using a TOPO® Blunt Cloning Kit (Invitrogen, Carlsbad, Calif., USA). The resulting plasmid was designated pEmY10.

The Eco RI site was then removed from the coding sequence of the hpt gene in pEmY10 using a QUIKCHANGE® Site-Directed Mutagenesis Kit (Stratagene, La Jolla, Calif., USA) according to the manufacturer's instructions using the primers shown below, where the lower case letters represent the non-mutated nucleotides of the target Eco RI site and the underlined case letters represent the mutated nucleotides. The resulting plasmid was designated pBK3.

```
Forward primer:
                                    (SEQ ID NO: 9)
5'-GGGTACCCCAAGGGCgTattcTGCAGATGGG-3'

Reverse primer:
                                    (SEQ ID NO: 10)
5'-CCCATCTGCAgaatAcGCCCTTGGGGTACCC-3'
```

The resulting hpt gene without the Eco RI site was PCR amplified from pBK3 using forward and reverse primers shown below.

```
Forward primer:
                                    (SEQ ID NO: 11)
5'-GGggtaccTTCATTTAAACGGCTTCAC-3'

Reverse primer:
                                    (SEQ ID NO: 12)
5'-GGggtaccCGACCAGCAGACGGCCC-3'
```

The underlined portions represent introduced Kpn I sites for cloning.

Portions of the *Aspergillus oryzae* pyrG gene were used to generate direct repeats and were PCR amplified from pSO2 (WO 98/12300) using the following primers:

```
Repeat 1:
Forward primer:
                                    (SEQ ID NO: 13)
5'-TCCcccgggTCTCTGGTACTCTTCGATC-3'

Reverse primer:
                                    (SEQ ID NO: 14)
5'-GGggtaccCGACCAGCAGACGGCCC-3'

Repeat 2:
Forward primer:
                                    (SEQ ID NO: 15)
5'-GGggtaccTCTCTGGTACTCTTCGATC-3'

Reverse primer:
                                    (SEQ ID NO: 16)
5'-TCCcccgggCGACCAGCAGACGGCCC-3'
```

The underlined portions represent introduced restriction sites Sma I (cccggg) or Kpn I (ggtacc) for cloning.

The three fragments (hpt, repeat #1 and repeat #2) were amplified in separate reactions (50 μl each) composed of 1× ThermoPol reaction buffer, 200 μM dNTPs, 0.25 μM each primer, 50 ng of template DNA, and 1 unit of Vent® DNA polymerase. The amplification reaction was performed using a ROBOCYCLER® programmed for 1 cycle at 95° C. for 2 minutes; 30 cycles each at 95° C. for 1 minute, 61° C. for 1 minute, and 72° C. for 2 minutes; and 1 cycle at 72° C. for 7 minutes.

The PCR products were separated by 1.5% agarose gel electrophoresis in TAE buffer. The approximately 2 kb amplified hpt fragment and the approximately 0.2 kb repeat fragments were excised from the gels and agarose-extracted using a MINELUTE® Gel Extraction Kit. The two pyrG repeat fragments were digested with Kpn I, dephosphorylated with calf intestine phosphatase (New England Biolabs Inc., Ipswich, Mass., USA), and treated with a MINELUTE® Reaction Cleanup Kit (QIAGEN Inc., Valencia, Calif., USA) according to the manufacturer's instructions. The fragments harboring repeat #1 and hpt were then ligated together using a QUICK LIGATION™ Kit (New England Biolabs Inc., Ipswich, Mass., USA) according to the manufacturer's instructions, treated with a MINELUTE® Reaction Cleanup Kit and the resulting ligation cloned into pCR®II Blunt using a TOPO® Blunt Cloning Kit. Sequence analysis confirmed one clone in which repeat #1 and the hpt fragment were ligated together in pCR®II Blunt. This plasmid was designated pEmY18.

In order to clone the second repeat into pEmY18, plasmid pEmy18 was digested with Eco RV and the digestion purified by 1% agarose gel electrophoresis in TAE buffer. A 5.6 kb fragment was excised from the gel and agarose-extracted using a QIAQUICK® Gel Extraction Kit. The 0.2 kb Repeat 2 fragment (described above) and digested pEmY18 were ligated together using a QUICK LIGATION™ Kit. The ligation mixture was used to transform SOLOPACK® Gold Supercompetent Cells (Stratagene, La Jolla, Calif., USA). Sequence analysis identified a plasmid in which the three components (repeat #1, hpt and repeat #2) were in the desired order and orientation and which lacked PCR errors. The resulting plasmid was designated pEmY20.

Figure 2:
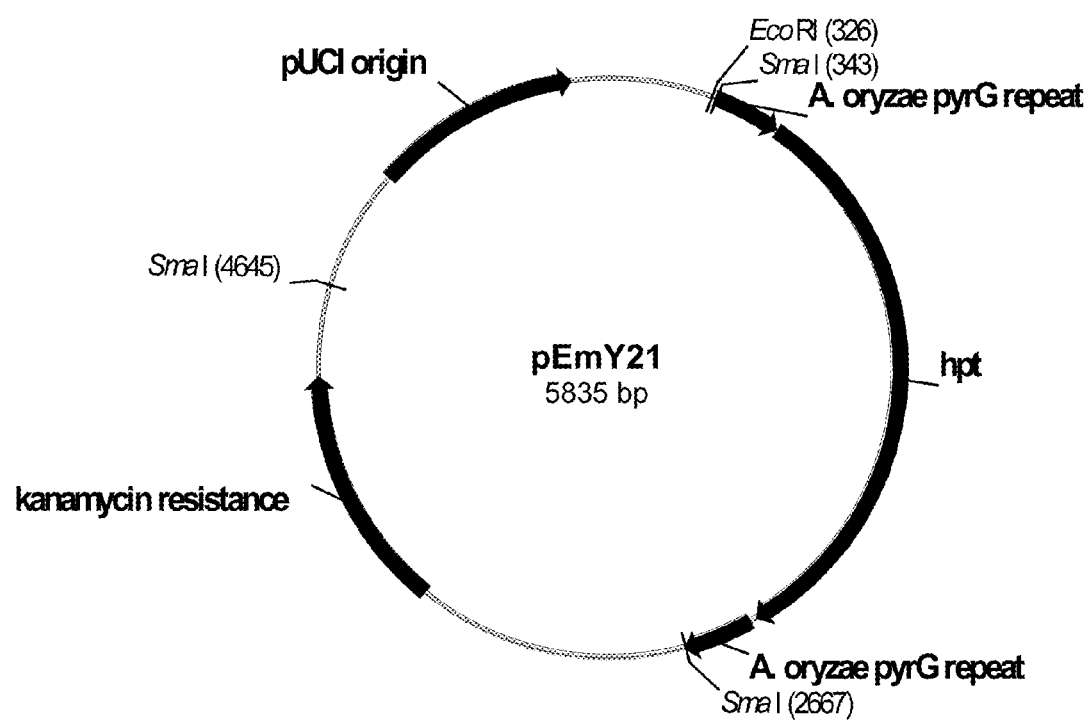
FIG. 2 shows a restriction map of pEmY21.

To insure that subsequent digestion of pEmY20 with Eco RI would liberate a single fragment, an Eco RI site was removed using a QUIKCHANGE® Site-Directed Mutagenesis Kit according to the manufacturer's instructions and forward and reverse primers shown below. The resulting plasmid was designated pEmY21 (FIG. 2) after sequence verification.

```
Forward primer:
                                    (SEQ ID NO: 17)
5'-GGGTACCCCAAGGGCQTATTCTGCAGATGGG-3'

Reverse primer:
                                    (SEQ ID NO: 18)
5'-CCCATCTGCAGAATACGCCCTTGGGGTACCC-3'
```

Example 5

Creation of the *Fusarium venenatum* pyrG Deletion Vector pEmY23

Figure 3:
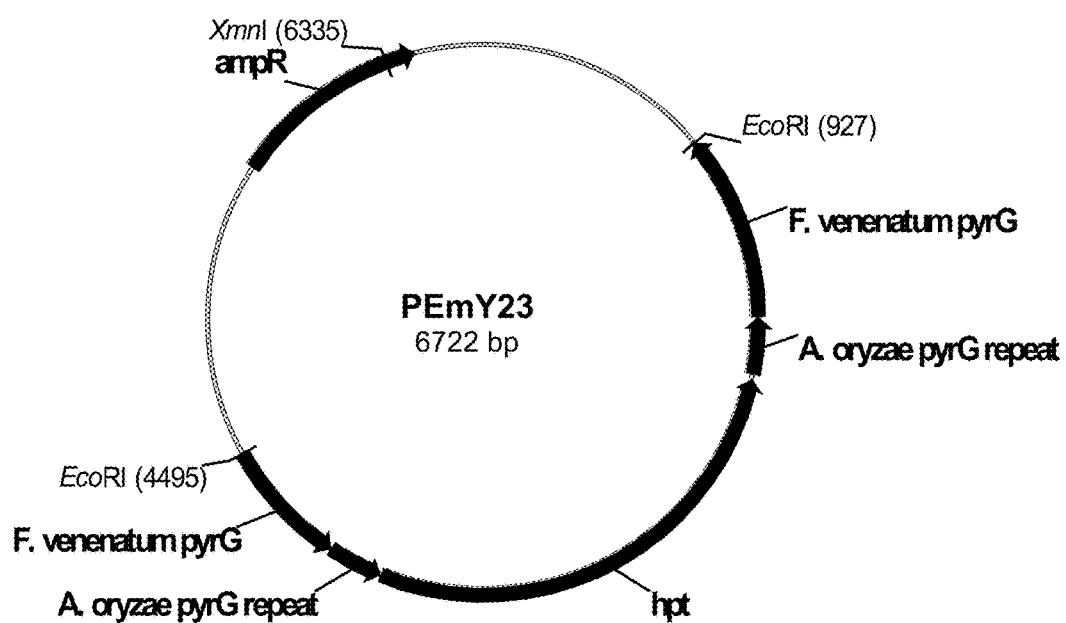
FIG. 3 shows a restriction map of pEmY23.

The *Fusarium venenatum* pyrG coding sequence (2,678 bp) was excised from pDM156.2 (Example 3) by digestion with Eco RV and Stu I restriction endonucleases, and the remaining 4,398 bp vector was gel-purified using a QIAQUICK® Gel Extraction Kit according to the manufacturer's directions. The Sma I fragment of pEmY21 was isolated and gel-purified using a QIAQUICK® Gel Extraction Kit and the two gel-purified fragments were ligated together. They were screened for insert orientation, sequenced for the absence of errors, and one of the clones with the correct insert sequence was selected and designated pEmY23 (FIG. 3).

Example 6

Construction of Plasmid pWTY1470-19-07

Plasmid pJRoy40 (U.S. Pat. No. 7,332,341), which harbors 5' and 3' flanking sequences of a *Fusarium venenatum* trichodiene synthase (tri5) gene (SEQ ID NO: 19 for the DNA sequence and SEQ ID NO: 20 for the deduced amino acid sequence), was used as template for amplification of a portion of the 5' tri5 gene flanking sequence. The PCR reaction contained 200 µM dNTPs, 1×Taq DNA polymerase buffer, 125 µg of pJRoy40 DNA, 50 µmol of each primer shown below, and 1 unit of Taq DNA polymerase in a final volume of 50 µl.

```
Forward primer:
                                    (SEQ ID NO: 21)
5'-GGGAGATCTTCGTTATCTGTGCC-3'

Reverse primer:
                                    (SEQ ID NO: 22)
5'-GGGAGATCTTAGTAGTCGGCATTTGAAAC-3'
```

(Underlined nucleotides indicate introduced Bgl II sites).

The amplification reaction was incubated in a ROBOCYCLER® programmed for 1 cycle at 95° C. for 3 minutes; 10 cycles each at 95° C. for 30 seconds, 52° C. for 45 seconds, and 7° C. for 2 minutes; 20 cycles each at 95° C. for 30 seconds, 52° C. for 45 seconds, and 72° C. for 5 minutes; and 1 cycle at 72° C. for 7 minutes.

PCR products were separated by 1.5% agarose gel electrophoresis using TBE buffer. A fragment of approximately 600 bp was excised from the gel and agarose-extracted using a MINELUTE® Gel Extraction Kit. The fragment was inserted into pCR®2.1 (Invitrogen, Carlsbad, Calif., USA) using a TOPO® TA Cloning Kit (Invitrogen, Carlsbad, Calif., USA) and ONE SHOT® TOP10 competent cells (Invitrogen, Carlsbad, Calif., USA) were transformed with 2 µl of the TOPO® TA cloning reaction. Plasmid DNA form eight of the resulting transformants was digested with Eco RI and Bgl II in separate reactions and the inserts for three transformants with the correct restriction digestion patterns were confirmed by DNA sequencing. One clone with the desired sequence was selected and designated pWTY1470-09-05.

A 608 bp Bgl II fragment harboring the tri5 gene 5' repeat was liberated from pWTY1470-09-05 by digestion with Bgl II, purified by 1.0% agarose gel electrophoresis using TBE buffer, excised from the gel, and agarose extracted using a MINELUTE® Gel Extraction Kit.

Figure 4:
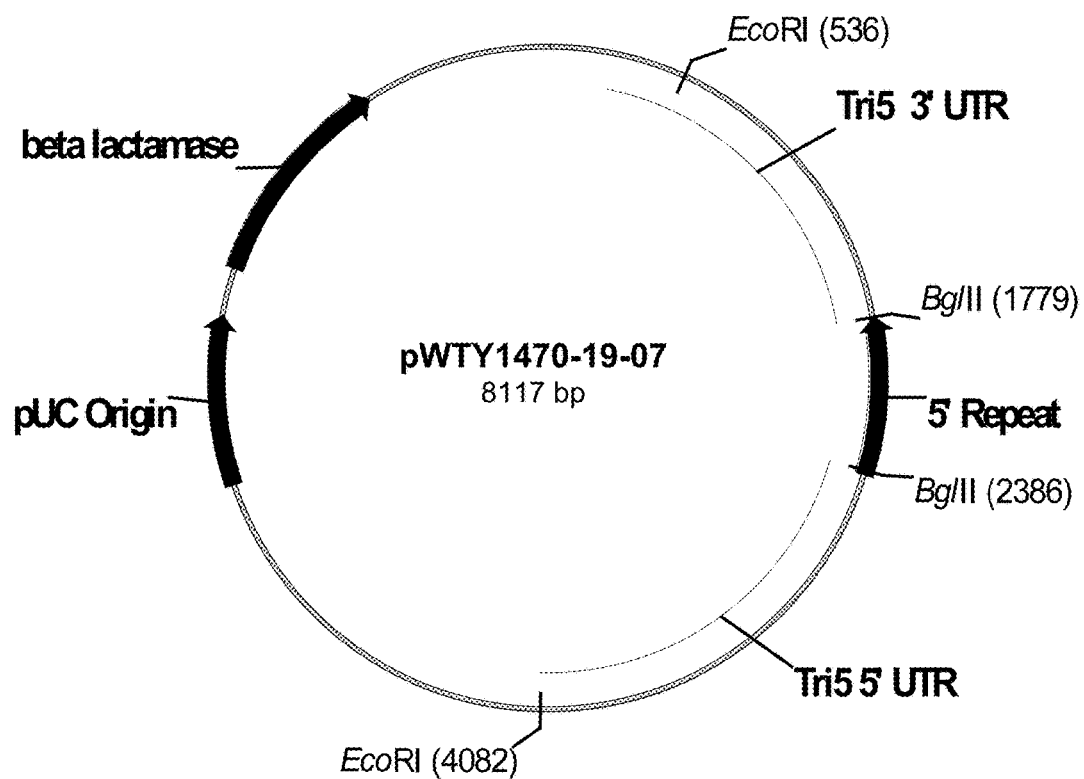
FIG. 4 shows a restriction map of pWTY1470-19-07.

Plasmid pJRoy40 was linearized by digestion with Bgl II, after which it was dephosphorylated using shrimp alkaline phosphatase (Roche Diagnostics Corporation, Indianapolis, Ind., USA) according to the manufacturer's instructions, and purified using a QIAQUICK® PCR Purification Kit (QIAGEN Inc., Valencia, Calif., USA). Linearized pJRoy40 and the gel-purified Bgl II fragment were ligated together using T4 DNA ligase (New England Biolabs Inc., Ipswich, Mass., USA) according to the manufacturer's instructions. Transformation of *E. coli* SURE® chemically competent cells (Stratagene, La Jolla, Calif., USA) was performed according to the manufacturer's directions. One transformant was confirmed by DNA sequencing to contain the desired vector, i.e., harboring the tri5 5' and 3' flanking sequences and a repeat of a portion of the 5' flanking sequence. The resulting plasmid was designated pWTY1470-19-07 (FIG. 4).

Example 7

Construction of Plasmid pWTY1515-02-01

Plasmid pWTY1470-19-07 was subjected to in vitro mutagenesis using a QUIKCHANGE® Site-Directed Mutagenesis Kit according to the manufacturer's instructions and forward and reverse primers shown below.

```
Forward primer:
                                       (SEQ ID NO: 23)
5'-CAAGTAACAGACGCGACAGCTTGCAAAATCTTCGTTATCTGTG-3'

Reverse primer:
                                       (SEQ ID NO: 24)
5'-CACAGATAACGAAGATTTTGCAAGCTGTCGCGTCTGTTACTTG-3'
```

The mutagenesis removed the Bgl II site at 1779 bp and rendered the Bgl II site at 2386 bp unique and usable in subsequent manipulations to insert fragments harboring thymidine kinase (tk) and hygromycin phosphotransferase (hpt) gene cassettes. The mutagenesis reaction was used to transform the kit-supplied *E. coli* XL10-GOLD® Ultra-competent cells (Stratagene, La Jolla, Calif., USA) according to the manufacturer's suggested protocol.

Figure 5:
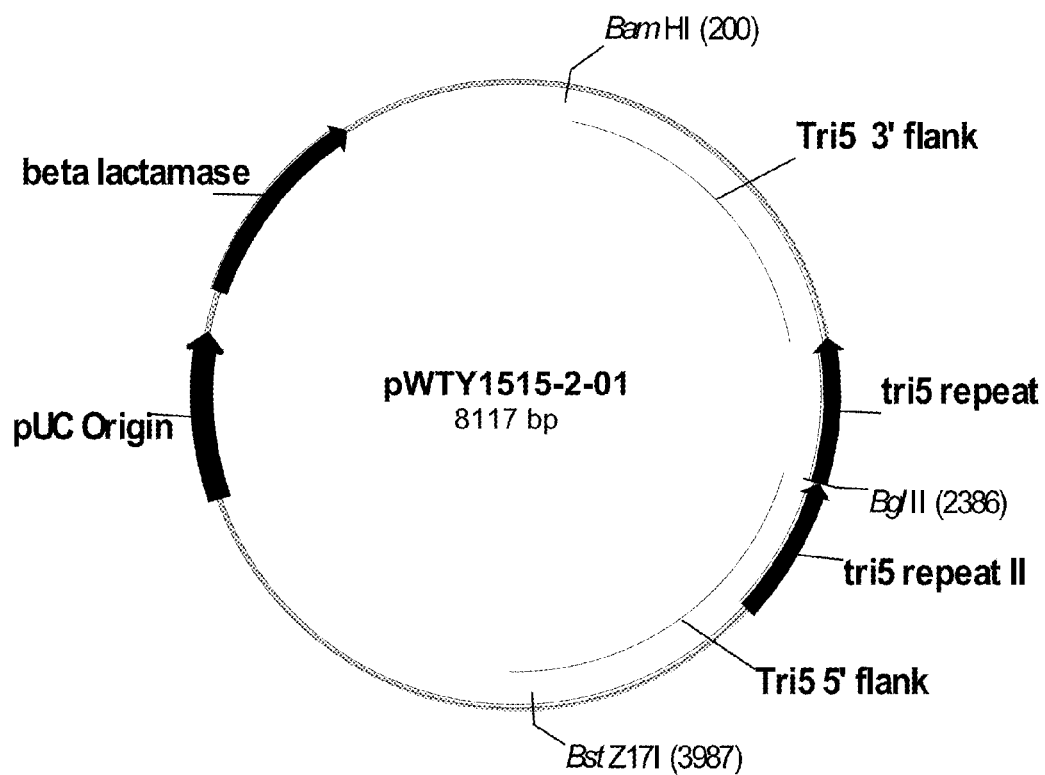
FIG. 5 shows a restriction map of pWTY1515-2-01.

One transformant harboring the mutations indicated above, as verified by sequence analysis, was designated pWTY1515-02-01 (FIG. 5) and used as the backbone in Example 10.

Example 8

Construction of Plasmid pJaL574

Figure 6:
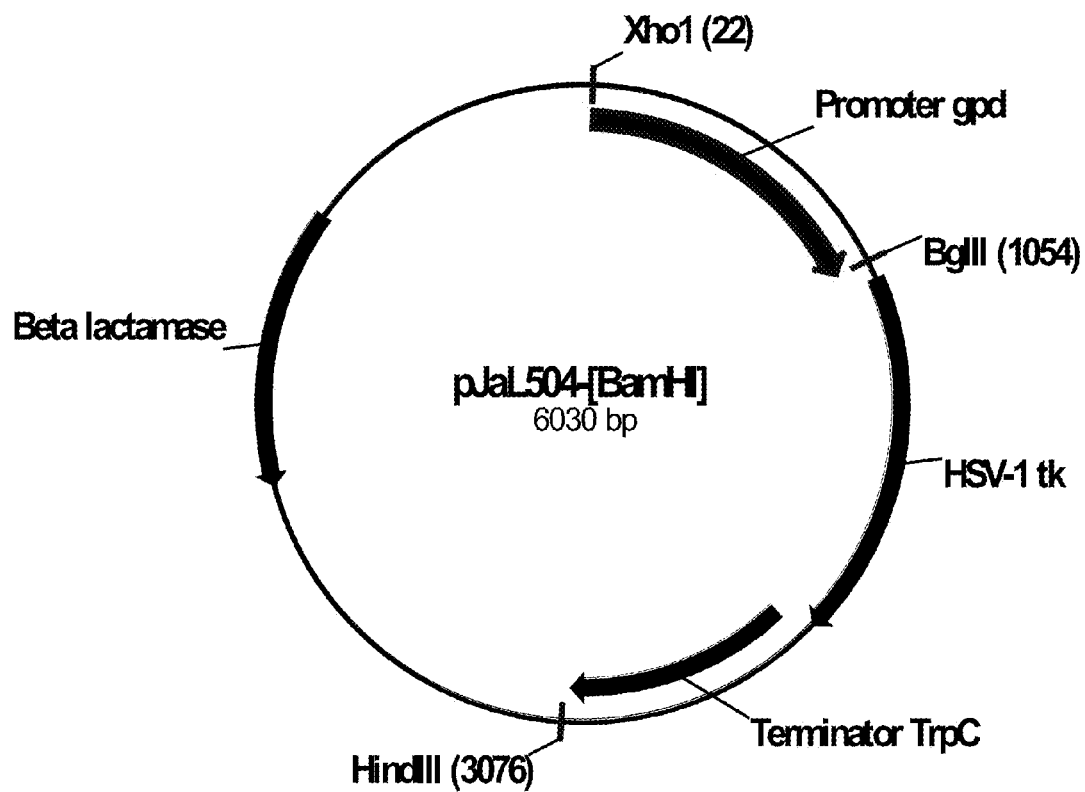
FIG. 6 shows a restriction map of pJaL504-[Bam HI].

Plasmid pDV8 (U.S. Pat. No. 6,806,062) harbors the Herpes simplex virus type 1 thymidine kinase (HSV1-TK; tk) gene (SEQ ID NO: 29 for the DNA sequence and SEQ ID NO: 30 for the deduced amino acid sequence) as a 1.2 kb Bgl II/Bam HI fragment inserted between a 1.0 kb Xho I/Bgl II fragment of the *Aspergillus nidulans* glyceraldehyde-3-phosphate dehydrogenase (gpdA) promoter and a 1.8 kb Bam HI/Hind III fragment harboring the tri-functional *Aspergillus nidulans* indoleglycerolphosphate synthase, phosphoribosylanthranilate isomerase, and glutamine amidotransferase (trpC) transcriptional terminator. Plasmid pDV8 was digested with Bam HI, extracted with phenol-chloroform, ethanol precipitated, and then filled in using Klenow polymerase (Stratagene, La Jolla, Calif., USA). The digested plasmid was re-ligated using a QUICK LIGATION™ Kit following the manufacturer's protocol, treated with a MINELUTE® Gel Extraction Kit, and the resulting ligation products cloned into pCR®4Blunt-TOPO® (Invitrogen, Carlsbad, Calif., USA) using a TOPO® Blunt Cloning Kit according to the manufacturer's instructions. The cloning reaction was transformed into ONE SHOT® chemically competent TOP10 cells (Invitrogen, Carlsbad, Calif., USA) according to the manufacturer's directions. Plasmid DNA was extracted from eight of the resulting transformants using a BIOROBOT® 9600 (QIAGEN Inc, Valencia, Calif., USA) and screened by restriction digestion using Xho I/Bam HI and Xho I/Hind III. DNA sequencing of plasmid DNA from two transformants with the correct restriction digestion pattern confirmed that both harbored the desired sequence. One was named pJaL504-[Bam HI] (FIG. 6).

Figure 7:
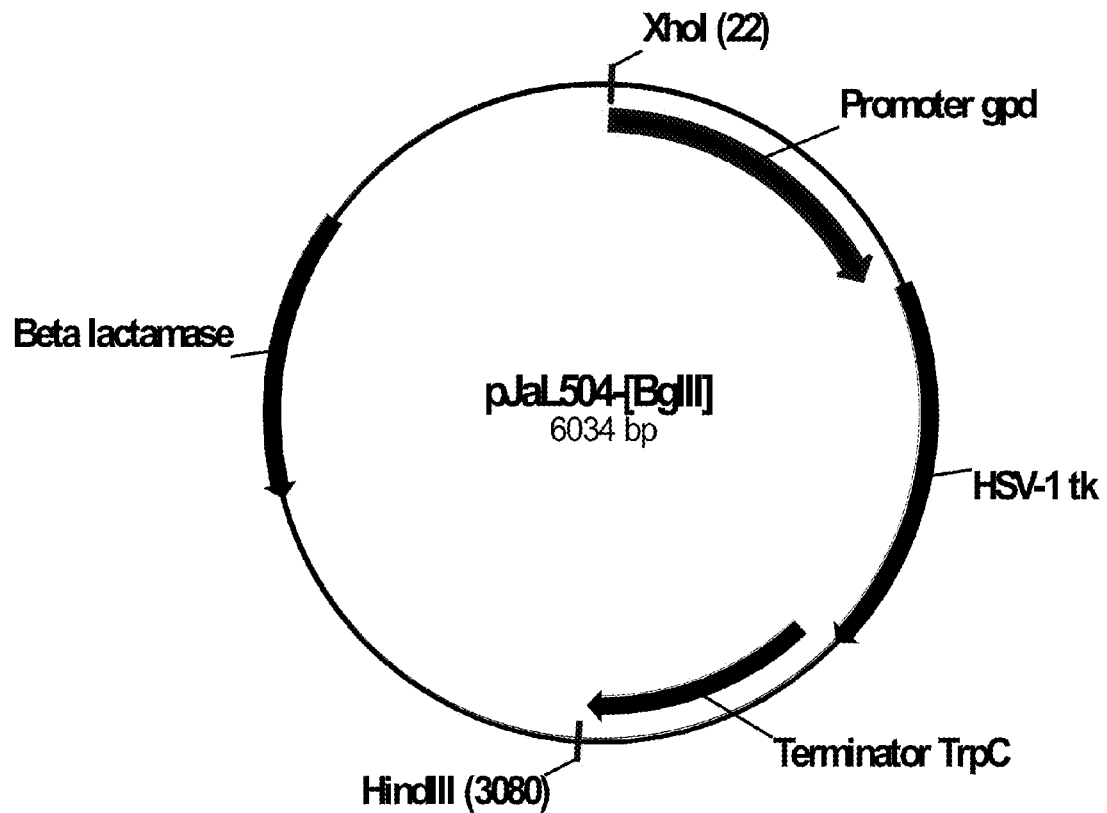
FIG. 7 shows a restriction map of pJaL504-[Bgl II].

Plasmid pJaL504-[Bam HI] was digested with Bgl II, extracted with phenol-chloroform, ethanol precipitated, and then filled in using Klenow polymerase. The digested plasmid was re-ligated using a QUICK LIGATION™ Kit following the manufacturer's protocol, treated with a MINELUTE® Reaction Cleanup Kit, and the resulting ligation cloned into pCR®4Blunt-TOPO® using a TOPO® Blunt Cloning Kit according to the manufacturer's instructions. The cloning reaction was transformed into ONE SHOT® chemically competent *E. coli* TOP10 cells according to the manufacturer's directions. Plasmid DNA was extracted from eight of the resulting transformants using a BIOROBOT® 9600 and screened by restriction digestion using Xho I/Bgl II and Xho I/Hind III. DNA sequencing of plasmid DNA from two transformants with the correct restriction digestion pattern confirmed that both harbored the desired sequence. One was named pJaL504-[Bgl II] (FIG. 7). Punt et al. (1990, *Gene* 3: 101-109) have previously shown that 364 bp of the *Aspergillus nidulans* gpdA promoter could be deleted without affecting the strength of the promoter. Based on these authors' observations, primer #172450 shown below was designed to truncate the *Aspergillus nidulans* gpdA promoter and reduce the size of the vector.

```
Primer 172450:
                                       (SEQ ID NO: 25)
5'-GACGAATTCTCTAGAAGATCTCTCGAGGAGCTCAAGCTTCTGTAC
AGTGACCGGTGACTC-3'
```

The underlined sequence corresponds to gpdA promoter sequence. The remaining sequence is a handle harboring the following restriction sites: Eco RI, Xba I, Bgl II, Xho I, and Hind III.

For truncating the *Aspergillus nidulans* trpC terminator (again to reduce vector size), primer #172499, shown below, was designed harboring an Eco RI handle.

```
Primer 172499:
                                       (SEQ ID NO: 26)
5'-GACGAATTCCGATGAATGTGTGTCCTG-3'
```

The underlined sequence corresponds to the trpC terminator sequence. Amplification using primers 172499 and 172450 truncates the promoter by 364 bp and the trpC terminator sequence by 239 bp.

PCR was performed with the above two primers using pJaL504-[Bgl II] as template to generate a 2.522 kb fragment composed of a truncated version of the *A. nidulans* gpdA promoter, the coding sequence of the HSV1-TK gene, and a truncated version of the *A. nidulans* trpC terminator. The amplification reaction consisted of 5 µl of 10× Buffer (Promega Corporation, Madison, Wis., USA), 0.4 µl of 25 mM dNTPs, 1.25 µl of primer 172450 (100 ng/µl), 1.25 µl of primer 172499 (100 ng/µl), 0.5 µl of pJaL504-[Bgl II] (100 ng/µl), 2 µl of Pfu DNA polymerase (Promega Corporation, Madison, Wis., USA) (2.5 U/µl), and 39.6 µl of sterile distilled water. The amplification reaction was incubated in a ROBOCYCLER® programmed for 1 cycle at 95° C. for 45 seconds; and 28 cycles each at 95° C. for 45 seconds, 57° C. for 45 seconds, and 72° C. for 5 minutes. A final extension was performed for 10 minutes at 72° C.

Figure 8:
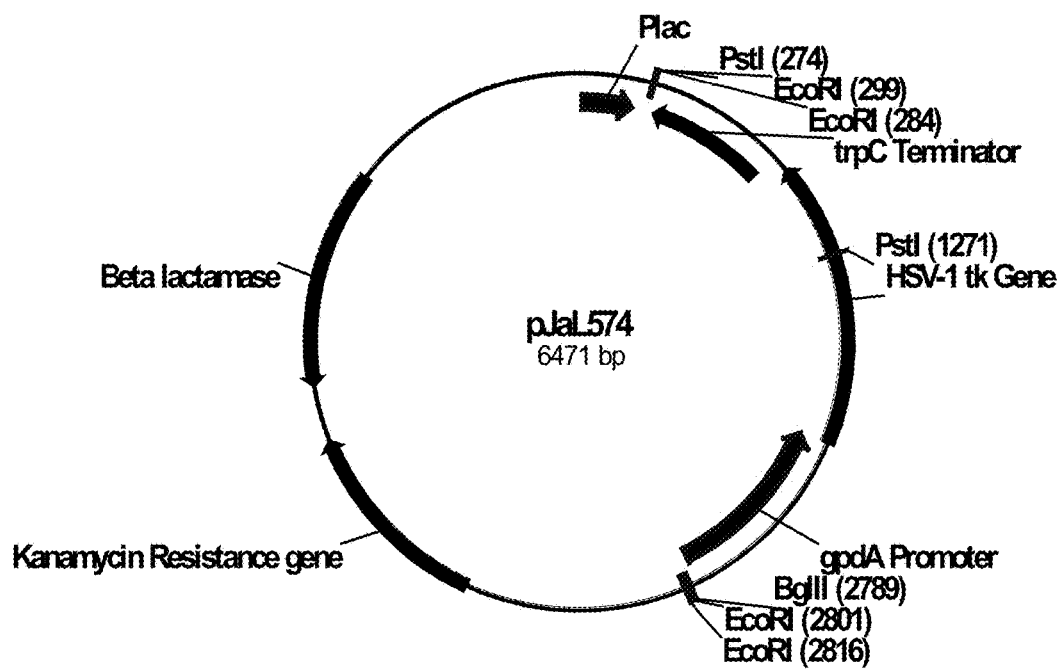
FIG. 8 shows a restriction map of pJaL574.

The amplification reaction was subjected to 1% agarose gel electrophoresis using low melting temperature agarose gel in 50 mM Tris-50 mM boric acid-1 mM disodium EDTA (TBE) buffer. A 2522 bp fragment was excised from the gel and extracted using a QIAQUICK® Gel Extraction Kit. The gel-purified DNA was then inserted into pCR®4Blunt- TOPO® using a TOPO® Blunt Cloning Kit according to the manufacturer's instructions. The cloning reaction was transformed into ONE SHOT® chemically competent TOP10 cells according to the manufacturer's directions. Plasmid DNA was extracted from eight of the resulting transformants using a BIOROBOT® 9600 and screened by restriction digestion using Eco RI and Bgl II. DNA sequencing of plasmid DNA from two transformants with the correct restriction digestion pattern confirmed that both harbored the desired sequence. One was designated pJaL574 (FIG. 8).

Example 9

Construction of Plasmid pWTY1449-02-01

Figure 9:
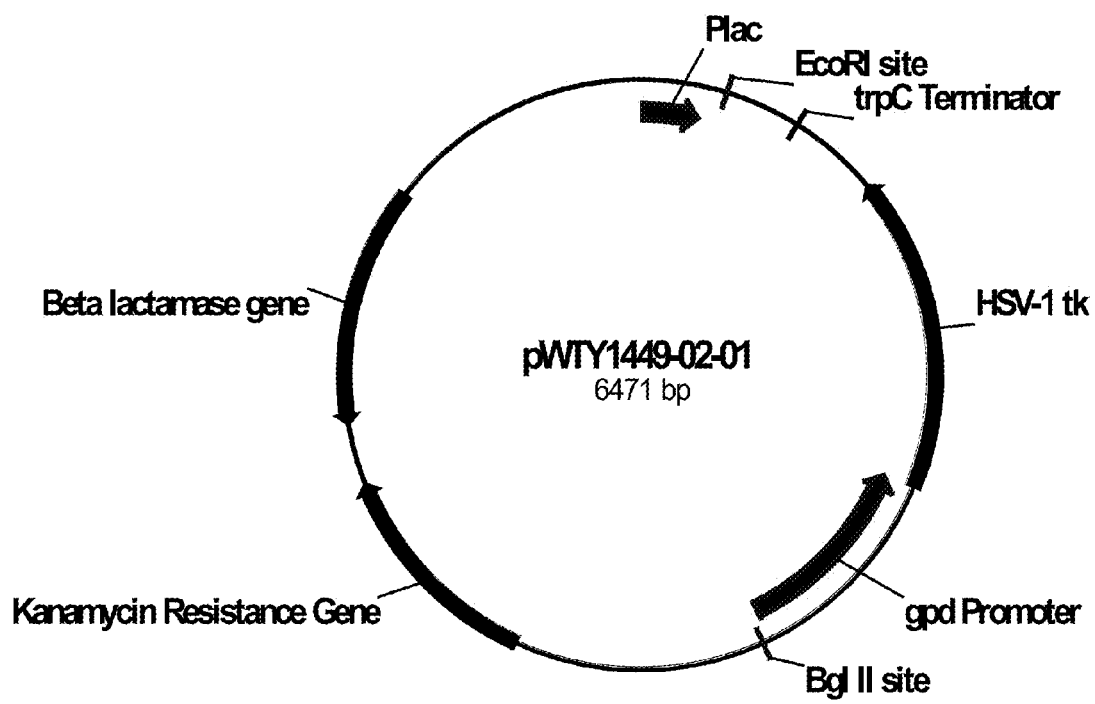
FIG. 9 shows a restriction map of pWTY1449-02-01.

Plasmid pJaL574 was transformed into competent *E. coli* SCS110 cells (Stratagene, La Jolla, Calif., USA) following the manufacturer's recommended protocol. Plasmid DNA was extracted from twenty-four of the resulting transformants, using a BIOROBOT® 9600, and then subjected to analytical digestion using Eco RI and Bgl II. Subsequent DNA sequence analysis resulted in the identification of a clone with the correct sequence, which was designated pWTY1449-02-01 (FIG. 9).

Example 10

Generation of the tri5 Deletion Vector pJfyS1579-21-16

An *E. coli* hygromycin phoshotransferase (hpt) gene cassette was PCR amplified from plasmid pEmY23 using an ADVANTAGE® GC Genomic PCR Kit (Clonetech, Palo Alto, Calif., USA) and gene-specific forward and reverse primers shown below. The underlined portion in the reverse primer is a Bgl II site for cloning.

```
Forward primer:
                                       (SEQ ID NO: 27)
5'-TTGAACTCTCAGATCCCTTCATTTAAACGGCTTCACGGGC-3'

Reverse primer:
                                       (SEQ ID NO: 28)
5'-CAGATAACGAAGATCTACGCCCTTGGGGTACCCAATATTC-3'
```

The PCR reaction contained 362 ng of pEmY23 as DNA template, 200 µm dNTP's, 1.1 mM magnesium acetate, 0.4 µM primers, 1×GC Reaction Buffer (Clonetech, Palo Alto, Calif., USA), 0.5 M GC Melt (Clonetech, Palo Alto, Calif., USA), and 1×GC Genomic Polymerase Mix (Clonetech, Palo Alto, Calif., USA) in a final volume of 50 µl.

The amplification reaction was incubated in an EPPENDORF® MASTERCYCLER® (Eppendorf, Munich, Germany) programmed for 1 cycle at 95° C. for 2 minutes; 25 cycles each at 94° C. for 30 seconds and 66° C. for 3 minutes; and 1 cycle at 66° C. for 3 minutes; and hold at 4° C.

Figure 10:
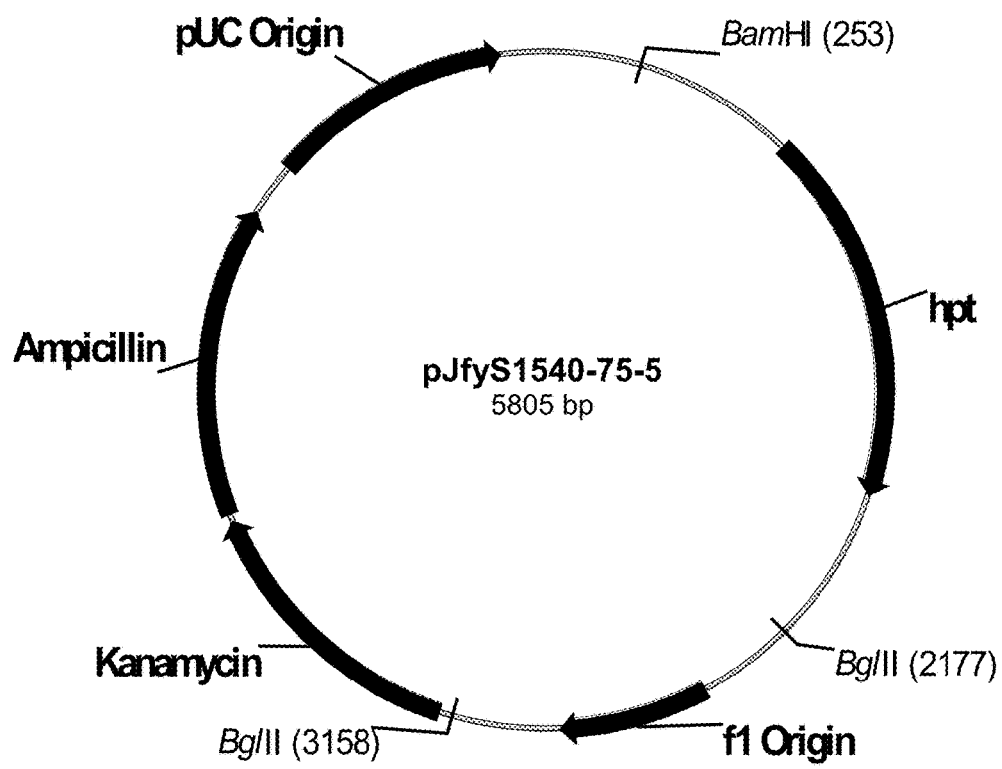
FIG. 10 shows a restriction map of pJfyS1540-75-5.

PCR products were separated by 1% agarose gel electrophoresis using TAE buffer. A fragment of approximately 1.9 kb was excised from the gel and agarose extracted using a MINIELUTE® Gel Extraction Kit. The fragment was cloned into pCR®2.1 using a TOPO® TA Cloning Kit according to the manufacturer's instructions. ONE SHOT® TOP10 competent cells (Invitrogen, Carlsbad, Calif., USA) were transformed with 2 µl of the TOPO® TA reaction. Sequence analysis of plasmid DNA from 8 transformants confirmed that there were no deviations from the expected sequence and the plasmid was designated pJfyS1540-75-5 (FIG. 10).

Figure 11:
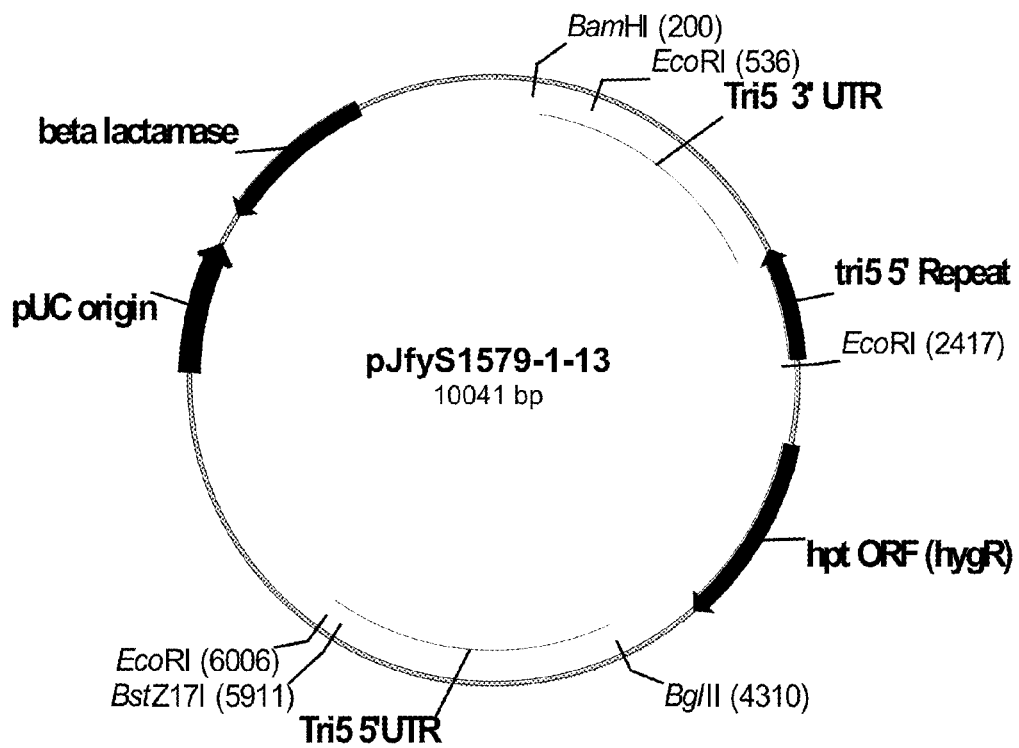
FIG. 11 shows a restriction map of pJfyS1579-1-13.

The hpt insert was liberated from pJfyS1540-75-05 by digestion with Bam HI and Bgl II and purified by 1% agarose gel electrophoresis in TAE buffer. A fragment of 1.9 kb was excised and agarose-extracted using a MINIELUTE® Gel Extraction Kit. A Rapid DNA Ligation Kit was used to ligate the fragment to Bgl II-linearized empty tri5 deletion vector pWTY1515-02-01 (Example 7) which had been dephosphorylated using calf intestine phosphatase. *E. coli* SURE® chemically competent cells were transformed with the ligation reaction and plasmid DNA from 24 of the resulting transformants was analyzed by restriction digestion with Eco RI to confirm the orientation of the insert. One of the transformants harboring the insert in the desired orientation was selected and designated pJfyS1579-1-13 (FIG. 11).

A Herpes simplex virus thymidine kinase (tk) gene (SEQ ID NO: 29 for the DNA sequence and SEQ ID NO: 30 for the deduced amino acid sequence) was PCR amplified using pWTY1449-2-1 as template and gene specific forward and reverse primers shown below. The bold sequence represents the introduced Bgl II site.

```
Forward primer:
                                       (SEQ ID NO: 31)
5'-GCCGACTACTAGATCGACCGGTGACTCTTTCTGGCATGCG-3'

Reverse primer:
                                       (SEQ ID NO: 32)
5'-CAGATAACGAAGATCTGAGAGTTCAAGGAAGAAACAGTGC-3'
```

The PCR reaction contained 1× HERCULASE® reaction buffer (Stratagene, La Jolla, Calif., USA), 200 µM dNTPs, 55 ng of pWTY1449-2-1, 0.2 µM primers, 2% DMSO, and 2.5 units of HERCULASE® DNA polymerase (Stratagene, La Jolla, Calif., USA) in a final volume of 50 µl.

The amplification reaction was incubated in an EPPENDORF® MASTERCYCLER® programmed for 1 cycle at 95° C. for 1 minute; 25 cycles each at 94° C. for 30 seconds, 60° C. for 30 seconds, and 68° C. for 2 minutes and 45 seconds; and 1 cycle at 68° C. for 2 minutes and 45 seconds; and a hold at 4° C.

Figure 12:
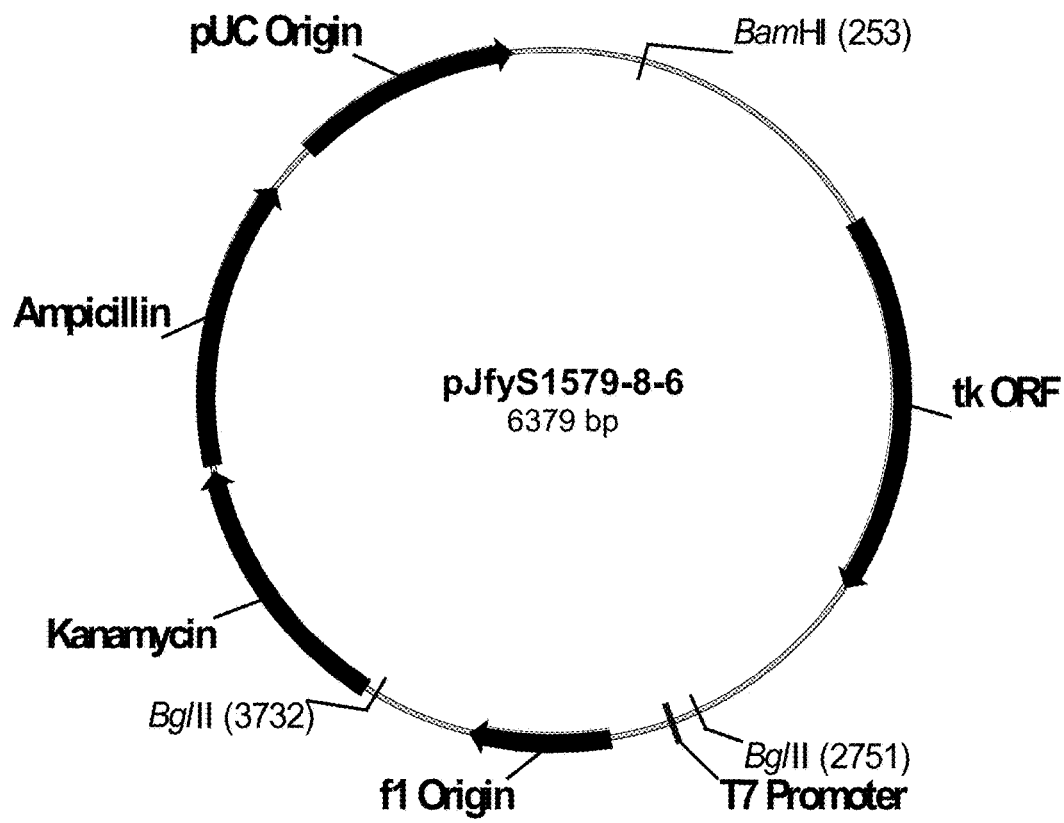
FIG. 12 shows a restriction map of pJfyS1579-8-6.

PCR products were separated by 1% agarose gel electrophoresis using TAE buffer. A fragment of approximately 2.8 kb was excised from the gel and purified using a MINIELUTE® Gel Extraction Kit. The fragment was cloned into pCR®2.1 using a TOPO® TA Cloning Kit. ONE SHOT® TOP10 competent cells (Invitrogen, Carlsbad, Calif., USA) were transformed with 2 µl of the TOPO® TA reaction. Sequence analysis of plasmid DNA from one of the transformants identified a mutation in the tk coding sequence (C1621G) resulting in an amino acid change of glycine to alanine. This mutation was corrected using a QUIKCHANGE® II XL Site-Directed Mutagenesis Kit (Stratagene, La Jolla, Calif., USA) according to the manufacturer's instructions and forward and reverse primers shown below. The lower case letter indicates the desired change. Sequence analysis of 16 clones resulted in the selection of one which was designated pJfyS1579-8-6 (FIG. 12).

Forward primer:
(SEQ ID NO: 33)
5'-CCCTGTTTCGGGgCCCCGAGTTGCTGG-3'

Reverse primer:
(SEQ ID NO: 34)
5'-CCAGCAACTCGGGgCCCCGAAACAGGG-3'

Figure 13:
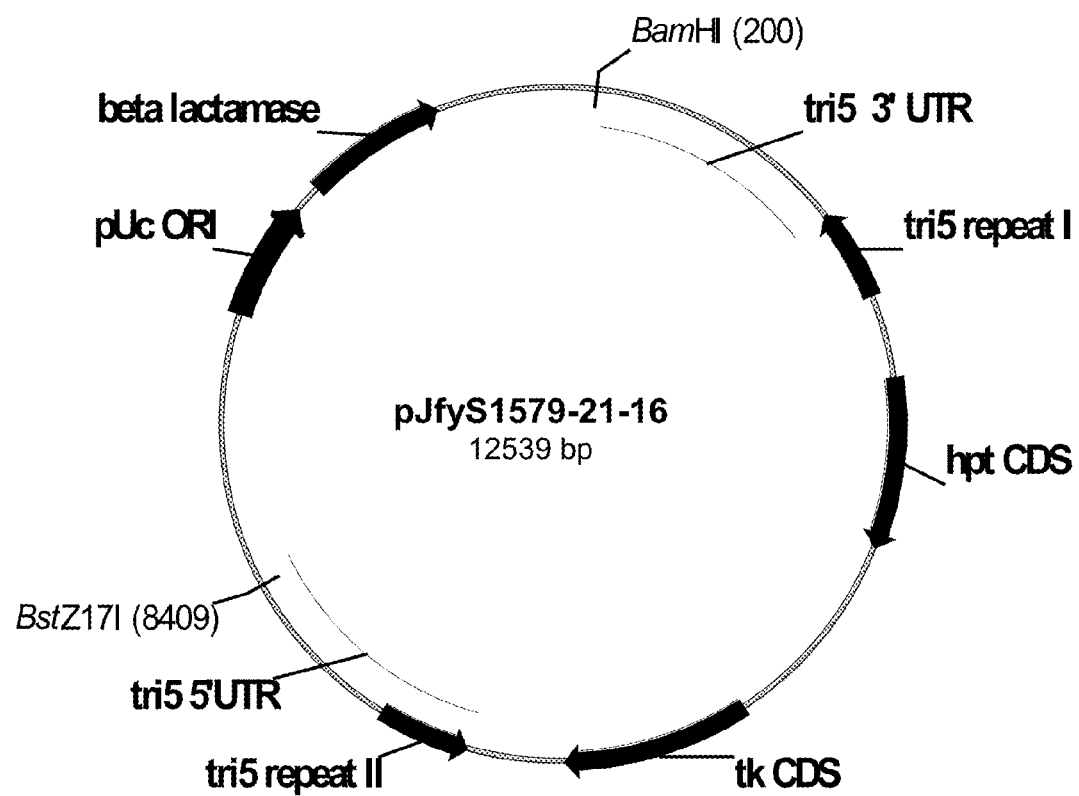
FIG. 13 shows a restriction map of pJfyS1579-21-16.

Plasmid pJfyS1579-08-06 was digested with Bam HI and Bgl II to liberate the 2.8 kb tk fragment and the fragment was purified as described above. This fragment was ligated to pJfyS1579-1-13, which had been linearized with Bgl II and treated with calf intestine phosphatase, using a QUICK LIGATION™ Kit and used to transform E. coli SURE® chemically competent cells according to the manufacturer's protocol. The resulting plasmid was designated pJfyS1579-21-16 (FIG. 13) and used as the tri5 deletion cassette.

Example 11

Construction of the Δtri5 Fusarium venenatum Strain JfyS1604-47-02

Fusarium venenatum A3/5 protoplasts were transformed with Bst Z1711Bam HI-linearized pJfyS1579-21-16 using the method described in Example 1. Transformants were selected on $VNO_3RLMT$ plates containing 125 μg of hygromycin B (Roche Diagnostics Corporation, Indianapolis, Ind., USA) per ml. After day 7, 48 out of 123 transformants were sub-cultured to a new plate containing the same medium. Eight transformants were then analyzed by Southern analysis as follows. Fungal biomass of these strains was generated by inoculating 25 ml of M400 medium with four 1 cm agar plugs from 7 day old transformants obtained as described above. The cultures were incubated for 3 days at 28° C. with shaking at 150 rpm. Agar plugs were removed and the cultures were filtered through MIRACLOTH™. Harvested biomass was frozen with liquid nitrogen and the mycelia were ground using a mortar and pestle.

Genomic DNA was isolated using a DNEASY® Plant Maxi Kit according to the manufacturer's instructions, except the lytic incubation period at 65° C. was extended to 1.5 hours from 10 minutes.

Two μg of genomic DNA were digested with 16 units of Sph I and 22 units of Dra I in a 50 μl reaction volume at 37° C. for 22 hours. The digestion was subjected to 1.0% agarose gel electrophoresis in TAE buffer. The DNA was fragmented in the gel by treating with 0.25 M HCl, denatured with 1.5 M NaCl-0.5 M NaOH, neutralized with 1.5 M NaCl-1 M Tris pH 8, and then transferred in 20×SSC to a NYTRAN® Supercharge nylon membrane using a TURBOBLOTTER™ Kit. The DNA was UV cross-linked to the membrane using a UV STRATALINKER™ and pre-hybridized for 1 hour at 42° C. in 20 ml of DIG Easy Hyb.

A PCR probe to the 3' flanking sequence of the tri5 gene was generated using the following forward and reverse primers.

Forward primer:
(SEQ ID NO: 35)
5'-GTGGGAGGATCTGATGGATCACCATGGGC-3"

Reverse primer:
(SEQ ID NO: 36)
5'-CCGGGTTTCGTTCCGAACGATCTTTACAAGG-3'

The probe was generated using a PCR Dig Probe Synthesis Kit according to the manufacturer's instructions. The probe was purified by 1.2% agarose gel electrophoresis in TAE buffer and the band corresponding to the probe was excised and agarose-extracted using a MINELUTE® Gel Extraction Kit. The probe was boiled for 5 minutes and added to 10 ml of DIG Easy Hyb to produce the hybridization solution. Hybridization was performed at 42° C. for 15-17 hours. The membrane was then washed under high stringency conditions in 2×SSC plus 0.1% SDS for 5 minutes at room temperature followed by two washes in 0.1× SSC plus 0.1% SDS for 15 minutes each at 65° C. The probe-target hybrids were detected by chemiluminescent assay (Roche Diagnostics, Indianapolis, Ind., USA) according to the manufacturer's instructions.

One transformant, *Fusarium venenatum* JfyS1579-43-23, harboring the deletion cassette in a single copy in the tri5 locus, as determined by Southern analysis, was sporulated by cutting four 1 $cm^2$ plugs using sterile toothpicks from a 7 day-old plate containing $VNO_3RLMT$ medium and transferring them to a 125 ml baffled shake flask containing 25 ml of RA medium. The flask was incubated at 28° C. with shaking at 150 rpm for 48 hours. The spore culture was filtered through sterile MIRACLOTH™ and collected in a 50 ml polypropylene tube. The concentration of spores was determined using a hemocytometer and $10^5$ spores (in one ml) were transferred to a 150 mm plate containing $VNO_3RLMT$ medium supplemented with 50 μM 5-fluoro-5'-deoxyuridine (FdU) (Sigma Chemical Co., St. Louis, Mo., USA) and incubated for 4 days at 28° C. Spore isolates were picked using sterile toothpicks and transferred to a new plate containing $VNO_3RLMT$ medium supplemented with 10 μM FdU and allowed to grow for 7 days at 24-28° C.

Genomic DNA was extracted from 7 spore isolates and Southern analyses performed as described above to insure the cassette's correct excision from the genome. All spore isolates analyzed by Southern blots had excised the cassette leaving behind one repeat as expected. One spore isolate was spore purified once by inducing sporulation in the strain as described in the preceding paragraph, and the spore concentration was determined using a hemocytometer and diluted to 40 spores per ml. One ml of the diluted spore solution was plated to 150 mm plates containing $VNO_3RLMT$ medium and the plates were incubated at 28° C. for 4 days. Spore isolates were sub-cultured to new plates containing $VNO_3RLMT$ medium and one spore isolate, designated *Fusarium venenatum* JfyS1604-17-02 (Δtri5), was used as the starting strain for deletion of the pyrG gene.

Example 12

Construction of a Universal Deletion Vector Harboring the Thymidine Kinase (Tk) Negative Selection Marker and Hygromycin Phosphotransferase (Hpt) Positive Selection Marker A universal deletion vector harboring both the thymidine kinase (tk) and hygromycin phosphotransferase (hpt) markers was constructed to facilitate assembly of subsequent deletion plasmids. Flanking sequences for 5' and 3' regions of the gene targeted for deletion can be easily ligated to the vector following digestion of the latter with Pme I or Asc I (for 5' flanking sequences) and Sbf I or Swa I (for 3' flanking sequences).

In order to PCR-amplify the direct repeats derived from the 5' flanking region of the *Fusarium venenatum* pyrG gene, 50 picomoles of the primers shown below were used in two PCR reactions containing 50 ng of pDM156.2, 1×Pfx Amplification Buffer (Invitrogen, Carlsbad, Calif., USA), 6

μl of a 10 mM blend of dNTPs, 2.5 units of PLATINUM® Pfx DNA polymerase (Invitrogen, Carlsbad, Calif., USA), and 1 μl of 50 mM MgSO$_4$ in a total volume of 50 μl.

```
Primers:
Repeat #1
Sense Primer:
                                     (SEQ ID NO: 37)
5'-GTTTAAACGGCGCGCC CGACAAAACAAGGCTACTGCAGGCAGG-3'

Antisense Primer:
                                     (SEQ ID NO: 38)
5'-TTGTCGCCCGGG AATACTCCAACTAGGCCTTG-3'

Repeat #2
Sense Primer:
                                     (SEQ ID NO: 39)
5'-AGTATTCCCGGG CGACAAAACAAGGCTACTGCA-3'

Antisense Primer:
                                     (SEQ ID NO: 40)
5'-ATTTAAATCCTGCAGG AATACTCCAACTAGGCCTTG-3'
```

The amplification reactions were incubated in an EPPENDORF® MASTERCYCLER® programmed as follows. For repeat #1: 1 cycle at 98° C. for 2 minutes; and 5 cycles each at 94° C. for 30 seconds, 55° C. for 30 seconds, and 68° C. for 1 minute. This was followed by 35 cycles each at 94° C. for 30 seconds, 59° C. for 30 seconds, and 68° C. for 1 minute. For repeat #2 the cycling parameters were: 1 cycle at 98° C. for 2 minutes; and 5 cycles each at 94° C. for 30 seconds, 55° C. for 30 seconds, and 68° C. for 1 minute. This was followed by 35 cycles each at 94° C. for 30 seconds, 56° C. for 30 seconds, and 68° C. for 1 minute. After the 35 cycles both reactions (i.e., repeats #1 and #2) were incubated at 68° C. for 10 minutes and then cooled at 10° C. until being further processed.

PCR products from both reactions were separated by 0.8% GTG-agarose (Cambrex Bioproducts, East Rutherford, N.J., USA) gel electrophoresis using TAE buffer. For repeat #1 and repeat #2, fragments of approximately 0.26 kb were excised from the gel and purified using Ultrafree®-DA spin cups (Millipore, Billerica, Mass., USA) according to the manufacturer's instructions. Ten microliters of each purified repeat were then used in a single overlapping PCR reaction containing 1×Pfx Amplification Buffer, 6 μl of a 10 mM blend of dATP, dTTP, dGTP, and dCTP, 2.5 units of PLATINUM® Pfx DNA polymerase, and 1 μl of 50 mM MgSO$_4$ in a total volume of 50 μl.

The amplification reaction was incubated in an EPPENDORF® MASTERCYCLER® programmed for 1 cycle at 98° C. for 2 minutes; and 5 cycles each at 94° C. for 30 seconds, 50° C. for 30 seconds, and 68° C. for 1 minute. The reaction was then mixed with a pre-warmed solution containing 50 picomoles of the sense primer for repeat #1 and 50 picomoles of the anti-sense primer for repeat #2, 1×Pfx Amplification Buffer, 6 μl of a 10 mM dNTPs, 2.5 units of PLATINUM® Pfx DNA polymerase, and 1 μl of 50 mM MgSO$_4$ in a final volume of 50 μl.

The new 100 μl amplification reaction was incubated in an EPPENDORF® MASTERCYCLER® programmed for 35 cycles each at 94° C. for 30 seconds, 58° C. for 30 seconds, and 68° C. for 1 minute. After 35 cycles, the reaction was incubated at 68° C. for 10 minutes and then cooled at 10° C. until being further processed. A 0.5 kb PCR product (harboring the repeat assembly) was isolated by 0.8% GTG-agarose gel electrophoresis as described above.

Figure 14:
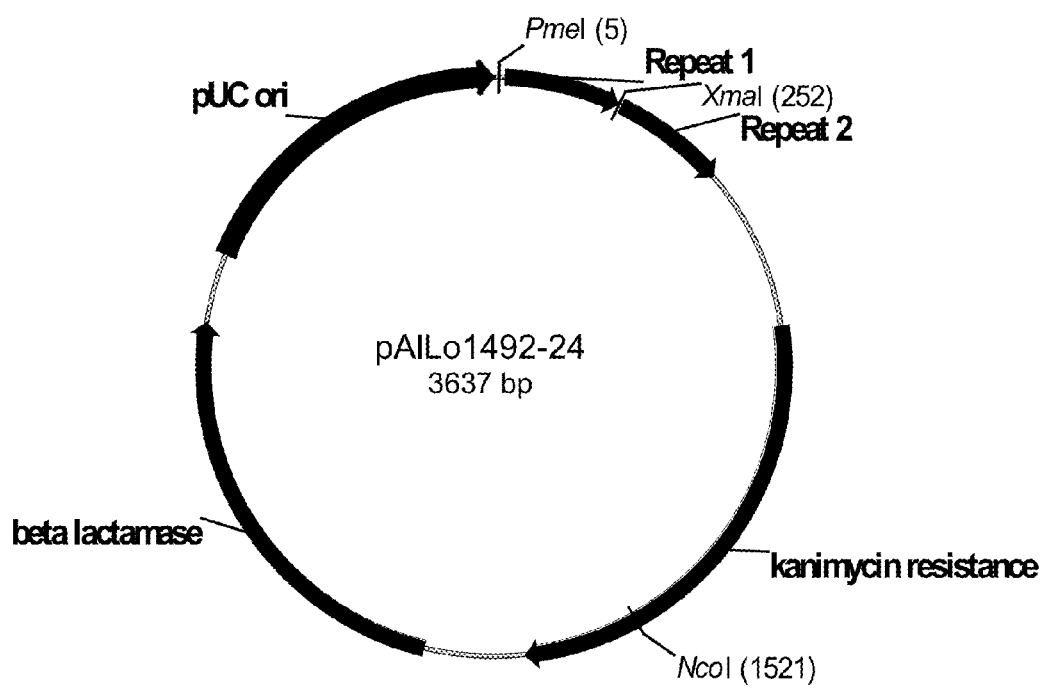
FIG. 14 shows a restriction map of pAlLo1492-24.

Plasmid pCR4 (Invitrogen, Carlsbad, Calif., USA) was used as the source of the vector backbone for the construction of the universal deletion vector. To remove the non-essential portions of the pCR4 DNA, 2.5 μg of plasmid pTter61C (WO 2005/074647) were digested sequentially with Bsp LU11 I and Bst XI. The digested vector was then treated with Antarctic phosphatase (New England Biolabs Inc., Ipswich, Mass., USA). The 3.1 kb digested backbone was isolated by 0.8% GTG-agarose gel electrophoresis as described above. The purified repeat assembly was then ligated to the purified vector backbone with a Rapid Ligation Kit (Roche Diagnostics Corporation, Indianapolis, Ind., USA). The ligation reaction consisted of: 75 ng of purified vector backbone and 3 μl of the purified repeat assembly. One microliter of this ligation reaction was used to transform chemically competent SOLOPACK® Supercompetent cells (Stratagene, Carlsbad, Calif., USA) using the manufacturer's suggested protocols. Twenty four transformants were analyzed by Nco I/Pme I restriction digestion. Twenty three out of twenty four transformants had the expected restriction digestion pattern. Clone pFvRs #10 was selected at random for sequencing to confirm that there were no PCR-induced errors. Sequencing analysis showed that the repeat assembly in clone pFvRs #10 had the expected sequence, and this was therefore selected as the backbone of the *Fusarium venenatum* universal vector and designated pAlLo1492-24 (FIG. 14).

The cassette harboring the hygromycin phosphotransferase (hpt) gene was PCR amplified from pEmY23 using the gene-specific forward and reverse primers shown below. The underlined sequence represents a Xma I site and the bold letters represent a Bgl II site. The four "a"s at each 5' end allow for subsequent digestion of the terminal ends of the PCR product.

```
Forward primer:
                                     (SEQ ID NO: 41)
5'-aaaacccgggCCTTCATTTAAACGGCTTCACGGGC-3'

Reverse primer:
                                     (SEQ ID NO: 42)
5'-aaaacccgggAGATCTACGCCCTTGGGGTACCCAATATTC-3'
```

The amplification reaction contained 60 ng of pEmY23, 200 μm dNTPs, 1 mM magnesium acetate, 0.4 μM primers, 1×Pfx Amplification Buffer, 0.5 M GC Melt, and 2.5 units of PLATINUM® Pfx polymerase in a final volume of 50 μl. The reaction was incubated in an EPPENDORF® MASTERCYCLER® programmed for 1 cycle at 95° C. for 2 minutes; 10 cycles each at 94° C. for 30 seconds, 60° C. for 30 seconds, and 68° C. for 1 minute 50 seconds; and 1 cycle at 68° C. for 7 minutes followed by holding at 4° C.

Figure 15:
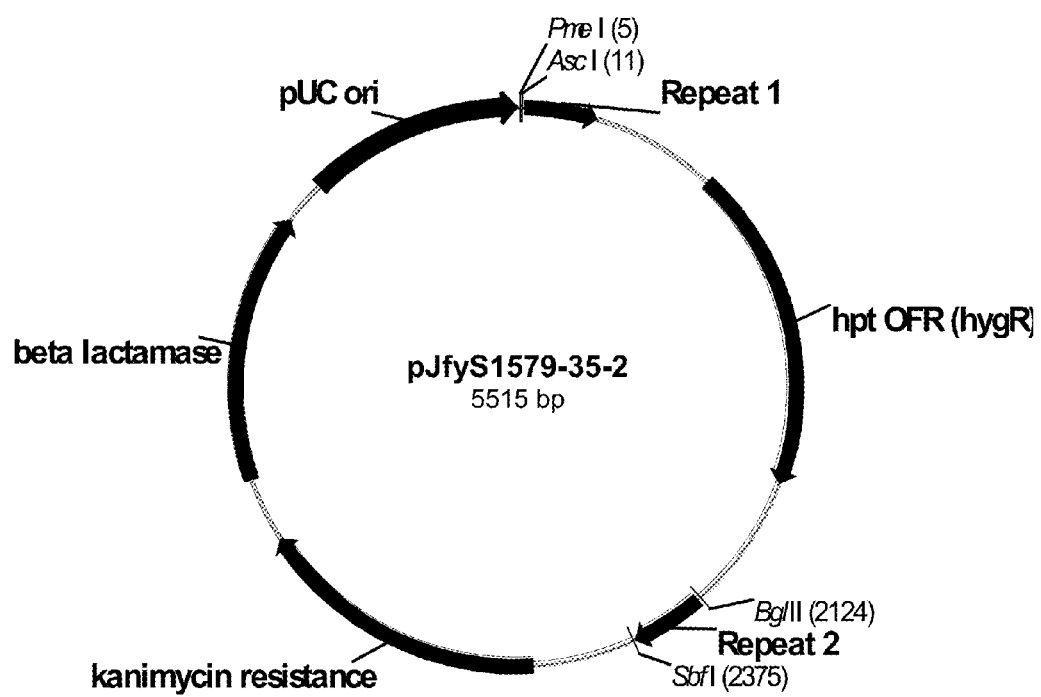
FIG. 15 shows a restriction map of pJfyS1579-35-2.

PCR products were separated by 1% agarose gel electrophoresis using TAE buffer. A fragment of approximately 1.8 kb was excised from the gel and agarose-extracted using a MINI ELUTE® Gel Extraction Kit. The gel-purified PCR product was subsequently digested with Xma I and run on a 1% agarose gel and gel-purified again as above. A QUICK LIGATION™ Kit was used to ligate the hpt PCR product to Xma I-linearized pAlLo1492-24, which had been treated with calf intestine phosphatase. The resulting plasmid was designated pJfyS1579-35-2 (FIG. 15) and was used as the recipient for the insertion of the thymidine kinase gene.

Figure 16:
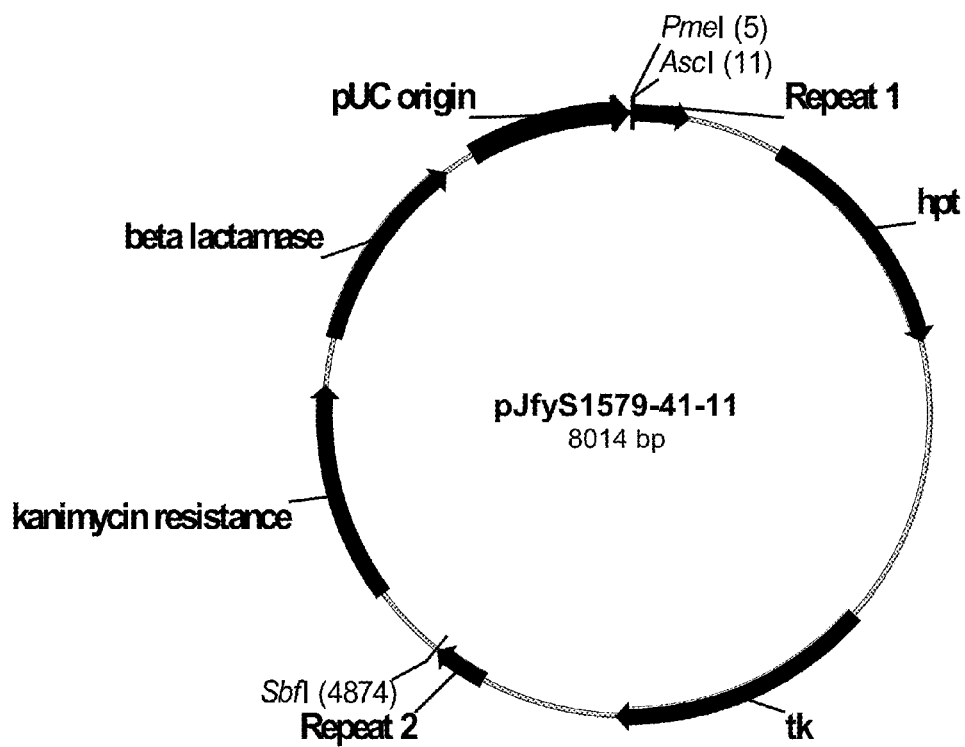
FIG. 16 shows a restriction map of pJfyS1579-41-11.

The source of the Herpes simplex virus tk cassette was plasmid pJfyS1579-8-6 (Example 10), from which the insert was liberated by digestion with Bam HI and Bgl II. The digestion products were separated by 1% agarose gel electrophoresis using TAE buffer, and a fragment corresponding to the 2.8 kb tk gene insert was excised and agarose-extracted using a MINELUTE® Gel Extraction Kit. A QUICK LIGATION™ Kit was used to ligate the tk gene cassette to Bgl II-linearized pJfyS1579-35-02, which had been treated with calf intestine phosphatase. The resulting plasmid was designated pJfyS1579-41-11 (FIG. 16) and this was used as the starting point for construction of the pyrG, amyA, alpA, and dps1 deletion vectors.

Example 13

Generation of the pyrG Deletion Vector pJfyS1604-55-13

The 3' flanking sequence of the *Fusarium venenatum* A3/5 pyrG gene (SEQ ID NO: 43 for the DNA sequence and SEQ ID NO: 44 for the deduced amino acid sequence) was amplified using an EXPAND® High Fidelity PCR System (Roche Diagnostics Corporation, Indianapolis, Ind., USA) and gene-specific forward and reverse primers shown below. The underlined portion is a Sbf I site introduced for cloning and the italicized portion is a Not I site introduced for later digestion to remove the pCR®2.1 portion of the plasmid before transformation.

Forward primer:
(SEQ ID NO: 45)
5'-aaaaaacctgcaggATCCTGCGCGGACTCTTGATTATTT-3'

Reverse primer:
(SEQ ID NO: 46)
5'-aaaaaacctgcagg*cggccgc*AATTCCATTCCTGTAGCTGAGTATA-3'

The amplification reaction contained 125 ng of *Fusarium venenatum* A3/5 genomic DNA, 200 µm dNTP's, 0.4 µM primers, 1× EXPAND® Buffer (Roche Diagnostics Corporation, Indianapolis, Ind., USA) with 5 mM MgCl₂, and 2.5 units of EXPAND® DNA polymerase (Roche Diagnostics Corporation, Indianapolis, Ind., USA) in a final volume of 50 µl.

The amplification reaction was incubated in an EPPENDORF® MASTERCYCLER® programmed for 1 cycle at 95° C. for 2 minutes; 10 cycles each at 94° C. for 30 seconds, 54° C. for 30 seconds, and 72° C. for 1 minute; and 20 cycles each at 94° C. for 30 seconds, 54° C. for 30 seconds, and 72° C. for 1 minute and 10 seconds.

PCR products were separated by 1% agarose gel electrophoresis using TAE buffer and a 0.7 kb fragment was excised and agarose extracted using a MINELUTE® Gel Extraction Kit.

The 0.7 kb PCR product was digested with Sbf I and purified by 1% agarose gel electrophoresis using TAE buffer. A fragment of approximately 0.7 kb was excised from the gel and further purified using an Ultrafree®-DA spin cup. The 0.7 kb fragment was ligated to pJfyS1579-41-11 (which had been digested with Sbf I and dephosphorylated using calf intestine phosphatase) using a QUICK LIGATION™ Kit and the ligation mixture used to transform *E. coli* SURE® chemically competent cells according to the manufacturer's protocol. The resulting plasmid was designated pJfyS1604-35-13.

The 5' pyrG flanking sequence from pEmY23 (Example 5) was amplified using an EXPAND® High Fidelity PCR System and gene-specific forward and reverse primers shown below. The underlined portion is a Pme I site introduced for cloning and the italicized portion is a Not I site introduced for later digestion to remove the beta-lactamase gene prior to fungal transformation.

Forward primer:
(SEQ ID NO: 47)
5'-aaaaaagtttaaac*gcggccgc*CTGTTGCCTTTGGGCCAATCAATG-3'

Reverse primer:
(SEQ ID NO: 48)
5'-aaaaaagtttaaacCTAGTTGGAGTATTGTTTGTTCTT-3'

The amplification reaction contained 20 ng of pEmY23, 200 µm dNTP's, 0.4 µM primers, 1× EXPAND® Buffer with 15 mM MgCl₂, and 2.5 units of EXPAND® DNA polymerase.

The amplification reaction was incubated in an EPPENDORF® MASTERCYCLER® programmed for 1 cycle at 95° C. for 2 minutes; 10 cycles each at 94° C. for 30 seconds, 53° C. for 30 seconds, and 72° C. for 40 seconds; and 20 cycles each at 94° C. for 30 seconds, 53° C. for 30 seconds, and 72° C. for 40 seconds plus an additional 10 seconds per subsequent cycle.

Figure 17:
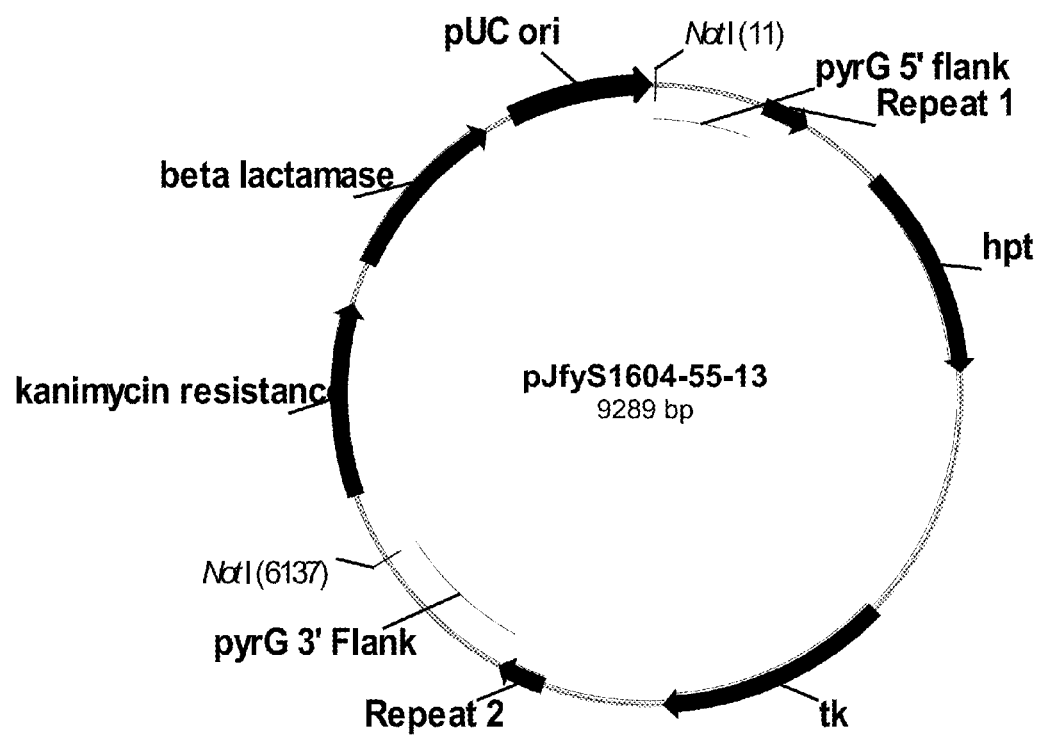
FIG. 17 shows a restriction map of pJfyS1604-55-13.

The PCR product was purified using a MINELUTE® PCR Purification Kit (QIAGEN Inc., Valencia, Calif., USA). The purified PCR products were digested with Pme 1 and separated by 1% agarose gel electrophoresis using TAE buffer. A fragment of approximately 0.5 kb was excised from the gel and agarose extracted using a MINELUTE® Gel Extraction Kit. The 0.5 kb fragment was ligated to Pme I digested and calf intestine phosphatase treated pJfyS1604-35-13 using a QUICK LIGATION™ Kit. The ligation reaction contained 50 ng of vector, 20 ng of insert, 1× QUICK LIGATION™ Reaction Buffer (New England Biolabs Inc., Ipswich, Mass., USA), and 10 units of Quick T4 DNA Ligase (New England Biolabs Inc., Ipswich, Mass., USA) in a 20 µl reaction volume. The reaction was incubated at room temperature for 5 minutes and 2 µl of the ligation were used to transform *E. coli* SURE® chemically competent cells according to the manufacturer's Instructions. Sequence analysis was used to identify transformants containing the insert in the desired orientation and to confirm the absence of PCR errors. The resulting plasmid was designated pJfyS1604-55-13 (FIG. 17) and was used as the pyrG gene deletion cassette.

Example 14

Generation of Δtri5 ΔpyrG *Fusarium venenatum* Strain JfyS1643-18-2

Fifty-one putative transformants of *Fusarium venenatum* JfyS1604-17-2 (Δtri5), transformed with Not I-digested and gel-purified pJfyS1604-55-13 according to the procedure described in Example 1, were transferred from transformation plates with sterile toothpicks to new plates containing $VNO_3RLMT$ medium supplemented with 125 μg of hygromycin B per ml and 10 mM uridine and grown at 24-28° C. for 7 days. Transformants were then analyzed phenotypically by transferring a plug to each of two $VNO_3RLMT$ plates, one with and one without uridine (10 mM). Nine transformants displaying no or poor growth on the plates without uridine were then analyzed by Southern analysis. Genomic DNA from each of the 9 transformants was extracted as described in Example 2 and 2 μg of each were digested with 28 units of Mfe I and 14 units of Dra I. A PCR probe to the 3' flanking sequence of the pyrG gene was generated as described in Example 11, with the following forward and reverse primers:

Forward primer:
(SEQ ID NO: 49)
5'-GGATCATCATGACAGCGTCCGCAAC-3'

Reverse primer:
(SEQ ID NO: 50)
5'-GGCATAGAAATCTGCAGCGCTCTCT-3'

Southern analysis indicated that 2 of the 9 uridine auxotrophs harbored the deletion cassette in a single copy while the remainder had sustained ectopic integrations of the cassette. One transformant, *Fusarium venenatum* JfyS1604-85-5, was sporulated as described in Example 1 in RA medium with 10 mM uridine, and $10^5$ spores were plated to a 150 mm plate containing VNO$_3$RLMT medium supplemented with 50 µM FdU and 0.1 mM uridine. The spore isolates obtained were sub-cultured to a new plate containing VNO$_3$RLMT medium supplemented with 10 µM FdU and 0.1 mM uridine and analyzed subsequently by Southern analysis to insure correct excision from the genome.

Figure 18:
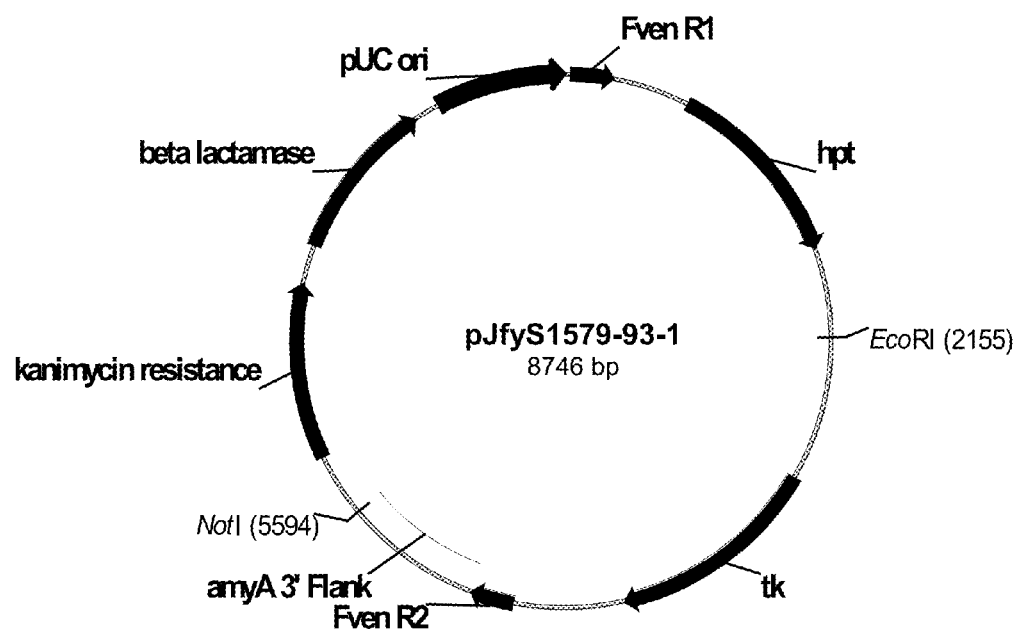
FIG. 18 shows a restriction map of pJfyS1579-93-1.

The analyzed strains had all excised the cassette correctly and one strain, *Fusarium venenatum* JfyS1643-10-3, was sporulated as described in the preceding paragraph. The spore concentration was determined using a hemocytometer and the stock solution diluted to a concentration of 40 spores per ml. One ml was plated to 150 mm plates containing $VNO_3RLMT$ medium supplemented with 10 mM uridine. Resulting spore colonies were sub-cultured to a new plate containing $VNO_3RLMT$ medium supplemented with 10 mM uridine and one spore isolate, *Fusarium venenatum* JfyS1643-18-2 (Δtri5 ΔpyrG), was used as the strain for deletion of the *Fusarium venenatum* alpha-amylase A gene (amyA).

Example 15

Generation of the amyA Deletion Vector pJfyS1604-17-2

In order to obtain upstream and downstream flanking sequence information for complete removal of the *Fusarium venenatum* amyA gene (SEQ ID NO: 51 for the DNA sequence and SEQ ID NO: 52 for the deduced amino acid sequence), a GENOME WALKER™ Universal Kit (Clonetech, Palo Alto, Calif., USA) was used. Each *Fusarium venenatum* A3/5 genomic DNA library, generated with the kit, was subjected to two rounds of PCR for the 5' flanking sequence using a 5' gene-specific primer and a 5' nested primer shown below. The 3' flanking sequence was obtained using a 3' gene-specific primer and a 3' nested primer shown below.

5' gene-specific primer:
(SEQ ID NO: 53)
5'-GAGGAATTGGATTTGGATGTGTGTGGAATA-3'

5' nested primer:
(SEQ ID NO: 54)
5'-GGAGTCTTTGTTCCAATGTGCTCGTTGA-3'

3' gene-specific primer:
(SEQ ID NO: 55)
5'-CTACACTAACGGTGAACCCGAGGTTCT-3'

3' nested primer:
(SEQ ID NO: 56)
5'-GCGGCAAACTAATGGGTGGTCGAGTTT-3'

The primary PCR reactions contained 1× HERCULASE® Reaction Buffer, 2 μl of each genomic DNA library (generated as described in the kit), 200 nM kit-supplied AP1 (adaptor primer 1), 200 nM gene specific primer (above), 200 μM dNTPs, and 2.5 units of HERCULASE® DNA polymerase in a 50 μl reaction volume.

The primary amplifications were performed in an EPPENDORF® MASTERCYCLER® programmed for 7 cycles each at 94° C. for 25 seconds and 72° C. for 3 minutes, and 32 cycles each at 94° C. for 25 seconds and 67° C. for 3 minutes, and one cycle at 67° C. for 7 minutes.

The secondary PCR reaction contained 1× HERCULASE® Reaction Buffer, 1 μl of each primary PCR reaction (above), 200 nM kit-supplied AP2 (adaptor primer 2), 200 nM gene specific nested primer (above), 200 μM dNTPs, and 2.5 units of HERCULASE® DNA polymerase in a 50 μl reaction volume.

The secondary amplifications were performed in an EPPENDORF® MASTERCYCLER® programmed for 5 cycles each at 94° C. for 25 seconds, 72° C. for 3 minutes, and 20 cycles each at 94° C. for 25 seconds and 67° C. for 3 minutes, and one cycle at 67° C. for 7 minutes.

PCR products were separated by 1% agarose gel electrophoresis using TAE buffer. A fragment of approximately 0.7 kb was excised from the gel and purified using a MINIELUTE® Gel Extraction Kit according to the manufacturer's instructions. The PCR product was sequenced directly using the corresponding nested primer described above and the kit-supplied primer 2. The obtained sequence was used to design primers to amplify a 1 kb region of the 5' flanking sequence and a 0.7 kb region of the 3' flanking sequence of the amyA gene for insertion into the empty deletion vector pJfyS1579-41-11.

The amyA 3' flanking sequence was PCR amplified from *Fusarium venenatum* A3/5 genomic DNA using forward and reverse primers shown below.

Forward primer:
(SEQ ID NO: 57)
5'-AAAAAA*cctgcagg*TAATGGGTGGTCGAGTTTAAAAGTA-3'

Reverse primer:
(SEQ ID NO: 58)
5'-AAAAAA*cctgcagg*<u>*gcggccgc*</u>TTTAAGCATCATTTTTGACTACGCA
C-3'

The underlined letters represent a Not I site for later beta-lactamase removal, and the italicized letters represent a Sbf I site for vector cloning.

The PCR reaction contained 1× HERCULASE® Reaction Buffer, 120 ng of genomic DNA template, 400 nm primers, 200 μM dNTPs, and 2.5 units of HERCULASE® DNA polymerase.

The amplification reaction was incubated in an EPPENDORF® MASTERCYCLER® programmed for 1 cycle at 95° C. for 2 minutes; 10 cycles each at 94° C. for 30 seconds, 55° C. for 30 seconds, and 72° C. for 1 minute; and 20 cycles each at 94° C. for 30 seconds, 55° C. for 30 seconds, and 72° C. for 1 minute and 10 seconds.

PCR products were separated by 1% agarose gel electrophoresis using TAE buffer. A fragment of approximately 0.7 kb was excised from the gel and agarose extracted using a MINIELUTE® Gel Extraction Kit. The PCR fragment was digested with Sbf I to produce sticky ends. This fragment was inserted into Sbf I-linearized, calf intestine phosphatase-treated universal deletion vector pJfyS1579-41-11. The ligation reaction contained 80 ng of vector, 80 ng of insert, 1× Quick Ligation Reaction Buffer, and 10 units of Quick T4 DNA Ligase in a 20 μl reaction volume. A 1.5 μl volume of the ligation reaction was used to transform 100 µl of *E. coli* SURE® chemically competent cells according to the manufacturer's instructions. Clones were screened for insert orientation using restriction analysis with Eco RI and sequence analysis, which identified a clone devoid of PCR errors. This plasmid was designated pJfyS1579-93-1 (FIG. 18) and used as the recipient for insertion of the 5' amyA flanking sequence.

The 5' amyA flanking sequence was PCR amplified using forward and reverse primers shown below. The underlined bases represent a Not I site for b/a gene removal and the other lower case letters represent a Pme I site to insure the fragment was blunt for cloning into a blunt vector site.

```
Forward primer:
                                        (SEQ ID NO: 59)
5'-AAAAAgtttaaacGCGGCCGCTTGATTATGGGATGACCCCAGACAA
GTGGT-3'

Reverse primer:
                                        (SEQ ID NO: 60)
5'-AAAAAgtttaaacCCGCACGAGCGTGTTTCCTTTTCATCTCG-3'
```

The PCR amplification was similar to that described above except for different cycling parameters. The amplification reaction was incubated in an EPPENDORF® MASTERCYCLER® programmed for 1 cycle at 95° C. for 2 minutes; 10 cycles each at 94° C. for 30 seconds, 55° C. for 30 seconds, and 72° C. for 1 minute 15 seconds; and 20 cycles each at 94° C. for 30 seconds, 55° C. for 30 seconds, and 72° C. for 1 minute 15 seconds with an additional 10 seconds per subsequent cycle.

PCR products were separated by 1% agarose gel electrophoresis using TAE buffer. A fragment of approximately 1 kb was excised from the gel and agarose-extracted using a MI NI ELUTE® Gel Extraction Kit. The 1 kb fragment was digested with Pme I to create blunt ends and the insert was cloned into Pme I-digested, calf intestine phosphatase-dephosphorylated pJfyS1579-93-1.

Figure 19:
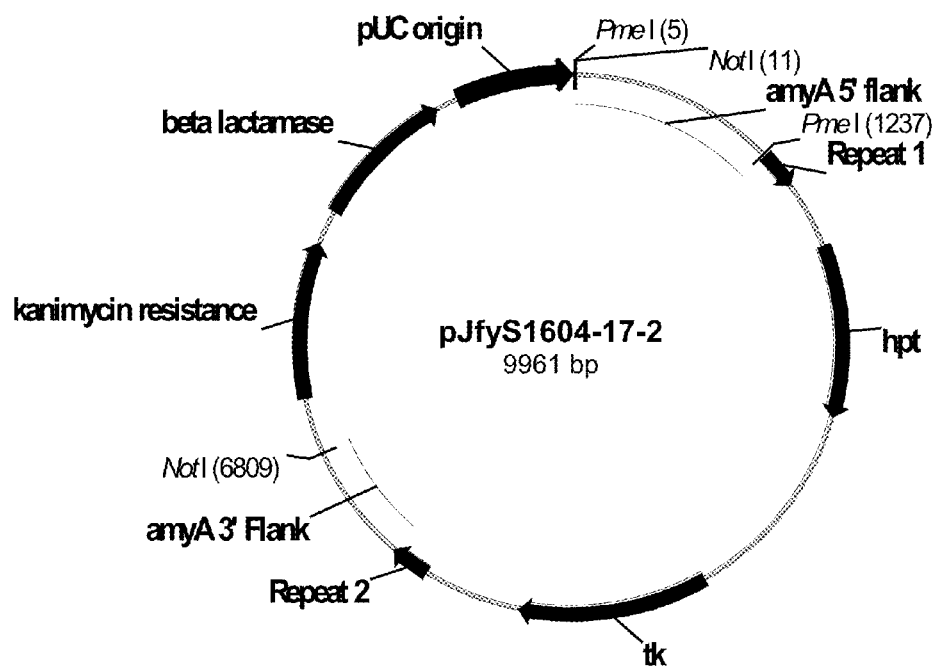
FIG. 19 shows a restriction map of pJfyS1604-17-2.

The ligation reaction contained 75 ng of vector, 100 ng of insert, 1× Quick Ligation Reaction Buffer, and 10 units of Quick T4 DNA Ligase in a 20 µl reaction volume. After a 5 minute incubation, 2 µl of the ligation reaction were used to transform 100 µl of *E. coli* SURE® chemically competent cells according to the manufacturer's instruction. Sequence analysis was used to confirm that the insert was in the correct orientation and the absence of PCR errors. The resulting vector identified was designated pJfyS1604-17-2 (FIG. 19).

Example 16

Generation of Δtri5 ΔpyrG ΔamyA *Fusarium venenatum* Strain JfyS1643-95-4

Five putative transformants of *Fusarium venenatum* JfyS1643-18-2 (Δtri5 ΔpyrG), transformed with Not I-digested and gel-purified pJfyS1604-17-2 according to the procedure described in Example 1, were transferred from transformation plates with sterile toothpicks to new plates containing VNO$_3$RLMT medium supplemented with 125 µg of hygromycin B per ml and 10 mM uridine and incubated at 24-28° C. for 7 days. For Southern analysis, 2 µg of genomic DNA were digested with 25 units of Ssp I. A DIG probe to the 5' flanking sequence of the amyA gene was generated as described in Example 11 with forward and reverse primers shown below.

```
Forward primer:
                                        (SEQ ID NO: 61)
5'-GGATCATCATGACAGCGTCCGCAAC-3'

Reverse primer:
                                        (SEQ ID NO: 62)
5'-GGCATAGAAATCTGCAGCGCTCTCT-3'
```

Southern analysis was performed as described in Example 2 and the results indicated that two of the five transformants had a replaced coding sequence with a single integration of the deletion cassette. A primary transformant designated *Fusarium venenatum* JfyS1643-73-2 was sporulated as described in Example 1 and $10^5$ spores were plated to a 150 mm diameter plate containing VNO$_3$RLMT medium supplemented with 50 µM FdU and 0.1 mM uridine. Spore isolates obtained were sub-cultured to a new plate containing VNO$_3$RLMT medium supplemented with 10 µM FdU and 0.1 mM uridine.

Two *Fusarium venenatum* spore isolates (JfyS1643-83-02 and JfyS1643-83-4) were spore purified once resulting in strains JfyS1643-95-1 and JfyS1643-95-2 (from JfyS1643-83-2) and Jfys1643-95-4 (from JfyS1643-83-4). The original spore isolates picked from the FdU plates, as well as their respective one time spore-purified isolates, were analyzed by Southern analysis to insure correct excision from the genome. All analyzed strains had excised the cassette correctly. *Fusarium venenatum* JfyS1643-95-4 (Δtri5 ΔpyrG ΔamyA) was used as the strain for deletion of the *Fusarium venenatum* alkaline protease A gene (alpA).

Example 17

Construction of Plasmid pEJG61

Figure 20:
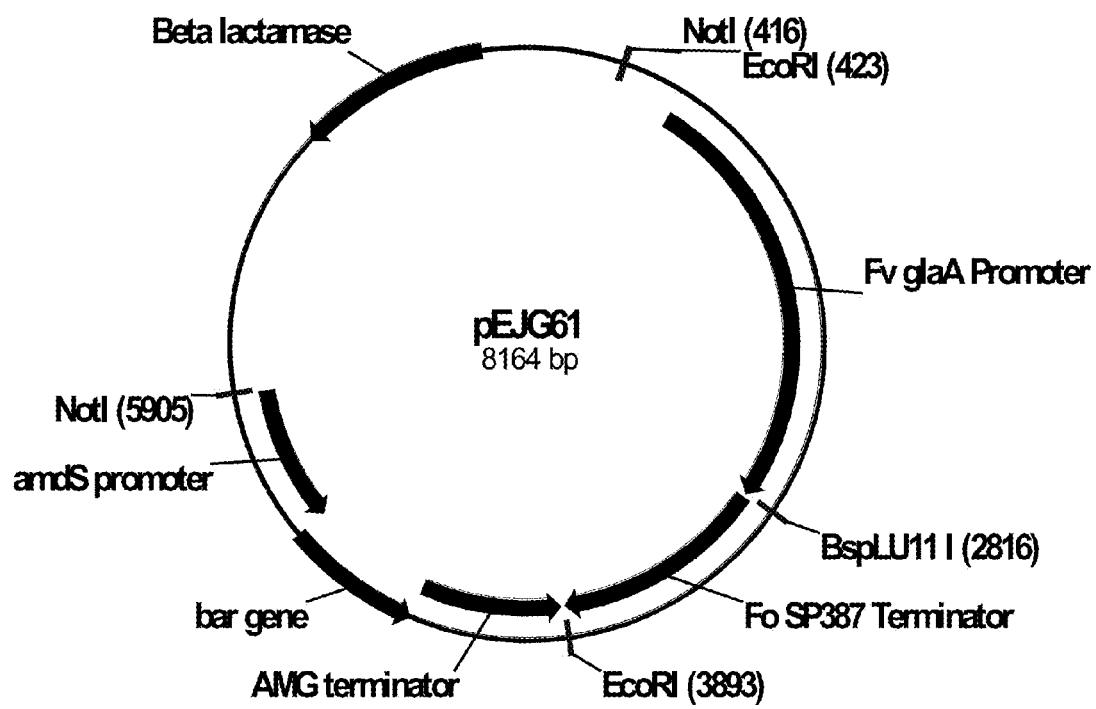
FIG. 20 shows a restriction map of pEJG61.

Plasmid pEJG61 (FIG. 20) was constructed as described in U.S. Pat. No. 7,368,271, with the exception that the orientation of the bar cassette was reversed (i.e., nucleotides 5901-5210 encode the amdS promoter, nucleotides 5209-4661 encode the bar coding sequence, and nucleotides 4660-4110 encode the *Aspergillus niger* glucoamylase (AMG) terminator).

Example 18

Construction of Plasmid pEJG69

The *Microdochium nivale* lactose oxidase (LOx) gene (SEQ ID NO: 63 for the DNA sequence and SEQ ID NO: 64 for the deduced amino acid sequence) was PCR amplified from pEJG33 (Xu et al., 2001, *European Journal of Biochemistry* 268: 1136-1142) using forward and reverse primers shown below.

```
Forward Primer:
                                        (SEQ ID NO: 65)
5'-CCCGCATGCGTTCTGCATTTATCTTG-3'

Reverse Primer:
                                        (SEQ ID NO: 66)
5'-GGGTTAATTAATTATTTGACAGGGCG-3'
```

The underlined portions represent introduced Sph I (forward) or Pac I (reverse) sites for cloning.

The PCR contained 200 µM dNTPs, 1 µM each primer, 50 ng of pEJG33, 1×Pwo buffer (Promega, Madison, Wis., USA), and 1 µl of Pwo Hot Start Polymerase (Promega, Madison, Wis., USA) in a final volume of 50 µl.

The amplification reaction was incubated in a ROBOCY-CLER® programmed for 1 cycle at 95° C. for 2 minutes; 10 cycles each at 95° C. for 30 seconds, 55° C. for 45 seconds, and 72° C. for 1 minute; 20 cycles each at 95° C. for 30 seconds, 55° C. for 45 seconds, and 72° C. for 1 minutes with an additional 20 second extension for each subsequent cycle; and 1 cycle at 50° C. for 10 minutes.

PCR products were separated by 1% agarose gel electrophoresis using TAE buffer. A fragment of approximately 1.5 kb was excised from the gel and agarose-extracted using a QIAQUICK® Gel Extraction Kit.

The lactose oxidase gene was re-amplified using the same conditions and purified as described above, except that the polymerase and buffer were replaced with Taq DNA polymerase and Taq DNA Polymerase Buffer, respectively, and the gel-purified PCR product above was used as template. The PCR product was cloned into pCR®2.1 using a TOPO® TA Cloning Kit and sequenced to insure the absence of PCR errors. The resulting error-free plasmid was digested with Sph I, treated with T4 DNA polymerase (New England Biolabs Inc., Ipswich, Mass., USA), purified using a QIAQUICK® Nucleotide Removal Kit (QIAGEN Inc., Valencia, Calif., USA), and digested with Pac I. The fragment was purified by 1% agarose gel electrophoresis in TAE buffer, and a fragment of approximately 1.5 kb was excised from the gel and agarose-extracted using a QIAQUICK® Gel Extraction Kit.

Plasmid pEJG61 was digested with Bsp LU11I, treated with Klenow DNA polymerase (New England Biolabs Inc., Ipswich, Mass., USA) according to the manufacturer's directions, and then digested with Pac I. The digested plasmid was purified by 1% agarose gel electrophoresis in TAE buffer and a 8 kb fragment was excised and agarose-extracted using a QIAQUICK® Gel Extraction Kit.

Figure 21:
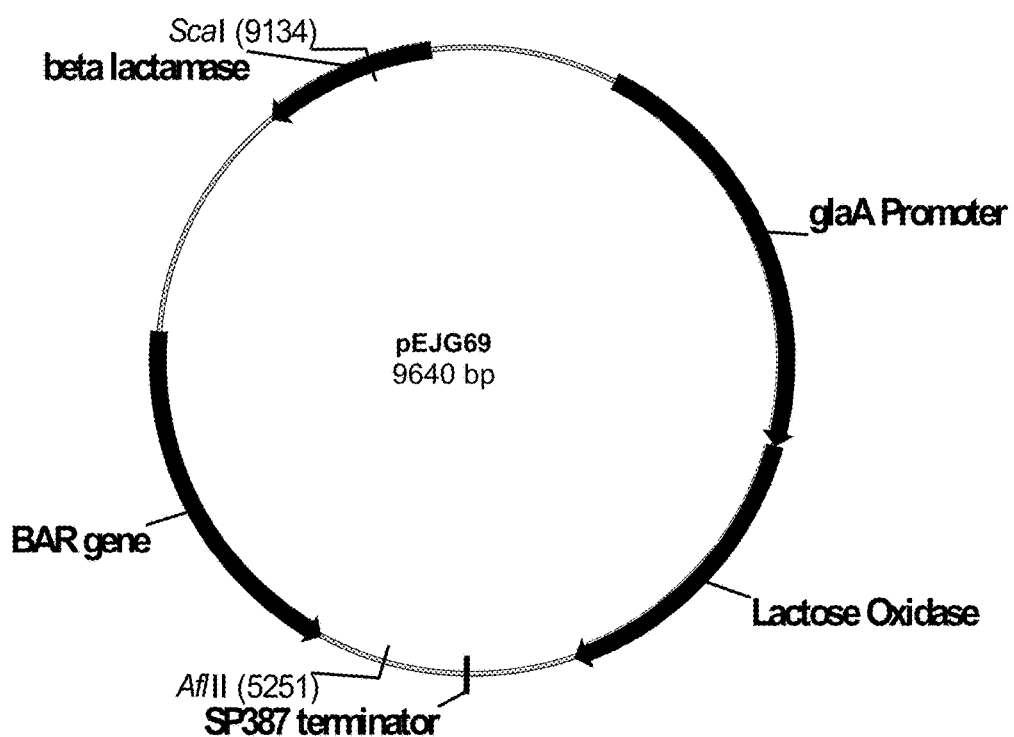
FIG. 21 shows a restriction map of pEJG69.

The LOx coding sequence was ligated to the Bsp LU11I- and Pac I-digested pEJG61 using T4 DNA Ligase according to the manufacturer's directions. Plasmids were screened by sequence analysis to insure the absence of PCR errors and a resulting plasmid was identified and designated pEJG69 (FIG. 21).

Example 19

Construction of Plasmid pEJG65

Plasmid pEJG61 (Example 17) was digested with Bsp LU11I, treated with Klenow DNA polymerase, and digested with Pac 1. The digested plasmid was isolated by 1% agarose gel electrophoresis in TAE buffer and a 8.1 kb fragment was excised and agarose-extracted using a QIAQUICK® Gel Extraction Kit.

The *Candida antarctica* lipase A coding sequence (SEQ ID NO: 67 for the DNA sequence and SEQ ID NO: 68 for the deduced amino acid sequence) was PCR amplified from pMT1229 (WO 94/01541) using forward and reverse primers shown below.

```
Forward primer:
                                      (SEQ ID NO: 69)
5'-GCATGCGAGTGTCCTTGCGC-3'

Reverse primer:
                                      (SEQ ID NO: 70)
5'-TTAATTAACTAAGGTGGTGTGATG-3'
```

The PCR reaction contained 200 µM dNTPs, 1 µM each primer, 20 ng of pMT1229, 1×Pwo buffer (Promega, Madison, Wis., USA), and 1 µl of Pwo Hot Start Polymerase.

The amplification reaction was incubated in a ROBOCY-CLER® programmed for 1 cycle at 94° C. for 2 minutes; 10 cycles each at 94° C. for 30 seconds, 55° C. for 45 seconds, and 72° C. for 1 minute; 17 cycles each at 94° C. for 30 seconds, 55° C. for 45 seconds, and 72° C. for 1 minutes with an additional 20 second extension for each subsequent cycle; and 1 cycle at 72° C. for 10 minutes.

PCR products were isolated by 1% agarose gel electrophoresis in TAE buffer and a 1.4 kb fragment was excised and agarose extracted using a QIAQUICK® Gel Extraction Kit. The PCR fragment was cloned into pCR®2.1 using a TOPO® TA Cloning Kit and sequenced to verify the absence of PCR errors.

Figure 22:
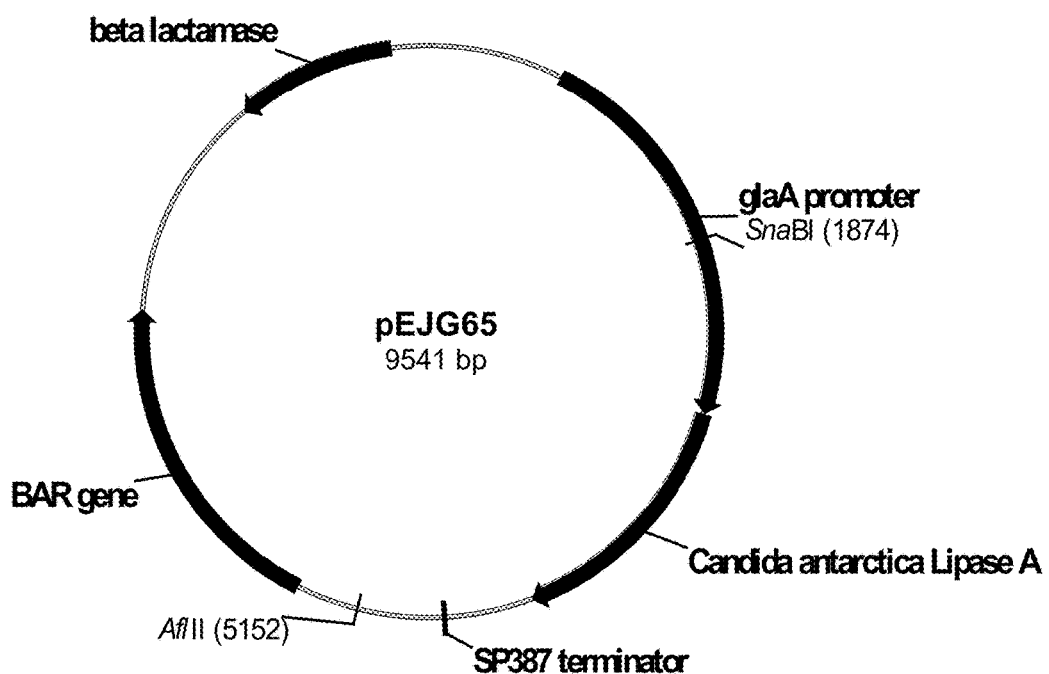
FIG. 22 shows a restriction map of pEJG65.

Due to the presence of an internal Sph I site in the coding sequence of the gene, the *Candida antarctica* lipase A coding sequence was liberated from pCR®2.1 as two separate fragments by separate digestions. To liberate the first fragment (1 kb), the plasmid was digested with Sph I and treated with T4 DNA polymerase. The polymerase was heat-inactivated for 10 minutes at 75° C. and the plasmid was digested with Nhe I. The second fragment (0.4 kb) was liberated from the plasmid with a Nhe I/Pac I digestion. Both digestions were subjected to 1% agarose gel electrophoresis in TAE buffer and a 1 kb fragment from the Sph I/Nhe I digestion and a 0.4 kb fragment from the Nhe I/Pac I digestion were excised and agarose-extracted using a QIAQUICK® Gel Extraction Kit. The two fragments were ligated to digested pEJG61 using T4 DNA ligase. The ligation reaction contained 1× Ligation Buffer (New England Biolabs Inc., Ipswich, Mass., USA), 100 ng of the 1 kb fragment above, 50 ng of the 0.4 kb fragment, 50 ng of digested pEJG61, and 10 units of T4 DNA ligase. The reaction was incubated at room temperature for 16 hours and used to transform *E. coli* XL10-GOLD® Ultra-competent cells according to manufacturer's instructions. Transformants were screened by sequence analysis and one clone containing a plasmid with the desired error-free coding sequence was identified and designated pEJG65 (FIG. 22).

Example 20

Construction of Plasmid pMStr19

Plasmid pMStr19 was constructed by cloning a *Fusarium oxysporum* phospholipase gene from pA2Ph10 (WO 1998/26057) into the *Fusarium venenatum* expression vector pDM181 (WO 2000/56900). PCR amplification was used to isolate the phospholipase gene on a convenient DNA fragment.

The *Fusarium oxysporum* phospholipase gene was specifically amplified from pA2Ph10 using standard amplification conditions with Pwo DNA polymerase (Roche Molecular Biochemicals, Basel, Switzerland) and an annealing temperature of 45° C. with the primers shown below.

```
PLMStr10:
                                      (SEQ ID NO: 71)
5'-TCAGATTTAAATATGCTTCTTCTACCACTCC-3'
        SwaI

PLMStr11:
                                      (SEQ ID NO: 72)
5'-AGTCTTAATTAAAGCTAGTGAATGAAAT-3'
```

The resulting DNA fragment was gel-purified and digested with Swa I. Plasmid pDM181 was also digested with Swa I and dephosphorylated. The DNA fragments were then ligated together to produce plasmid pMStr18.

Figure 23:
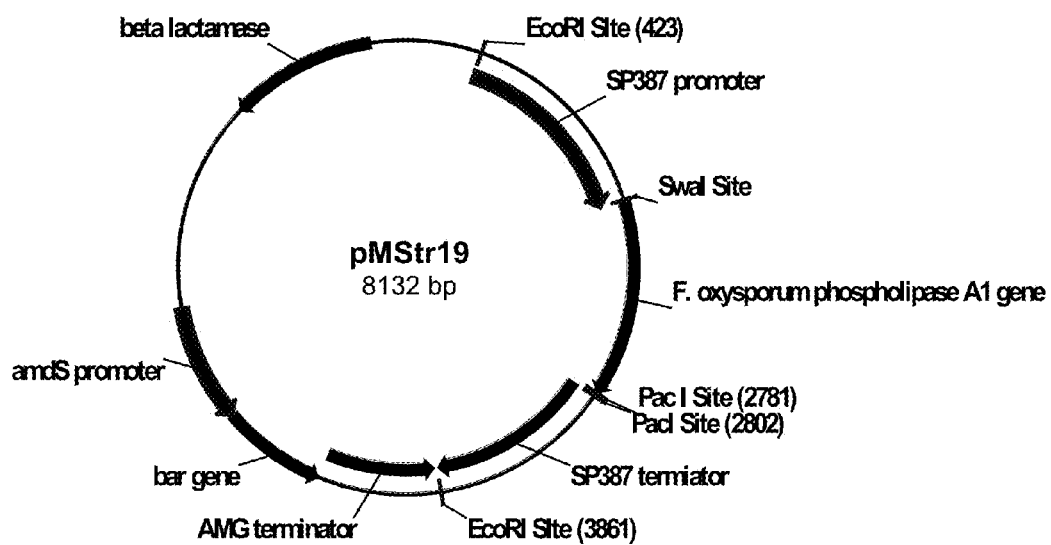
FIG. 23 shows a restriction map of pMStr19.

The phospholipase gene in two individual *E. coli* transformants of pMStr18, #4, and #17 generated using the ligation mixture, were sequenced using standard primer walking methods. Both had acquired single point mutations at different positions in the gene. The mutations were separated by a Nar I site, which cleaves pMStr18 twice. An error-free phospholipase gene was therefore assembled in the *Fusarium* expression vector pDM181 by digesting both pMStr18#4 and pMStr18#17 with Nar I, isolating the error-free fragments, and ligating them together to produce pMStr19 (FIG. 23). The phospholipase sequence in pMStr19 was confirmed using standard methods.

Example 21

Construction of Plasmid pEJG49

The *Fusarium venenatum* expression vector pEJG49 was generated by modification of pSheB1 (WO 2000/56900). The modifications included (a) removal of one Bsp LU11I site within the pSheB1 sequence by site-directed mutagenesis; (b) removal of 850 bp of the *Fusarium oxysporum* trypsin promoter; (c) introduction of a Bsp LU11I site, by ligation of a linker, to aid in the insertion of the 2 kb *Fusarium venenatum* glucoamylase promoter; and (d) introduction of a *Fusarium oxysporum* phospholipase gene.

Removal of the Bsp LU11I site within the pSheB1 sequence was accomplished using a QUIKCHANGE® Site-Directed Mutagenesis Kit according to the manufacturer's instructions with the following pairs of mutagenesis primers:

```
                                      (SEQ ID NO: 73)
5'-GCAGGAAAGAACAAGTGAGCAAAAGGC-3'

(SEQ ID NO: 74)
5'-GCCTTTTGCTCACTTGTTCTTTCCTGC-3'
```

This created pSheB1 intermediate 1.

Removal of 930 bp of the *Fusarium oxysporum* trypsin promoter was accomplished by digesting pSheB1 intermediate 1 (6,971 bp) with Stu I and Pac I, subjecting the digest to 1% agarose gel electrophoresis using TBE buffer, excising the 6,040 bp vector fragment, and purifying the excised fragment with a QIAQUICK® Gel Extraction Kit. To introduce a new Bsp LU11I site, a linker was created using the following primers:

```
                                      (SEQ ID NO: 75)
5'-dCCTACATGTTTAAT-3'
      Bsp Lu11I (SEQ ID NO: 76)
5'-dTAAACATGTAGG-3'
```

Each primer (2 μg each) was heated at 70° C. for 10 minutes and then cooled to room temperature over an hour. This linker was ligated into the Stu I-Pac 1-digested pSheB1 intermediate 1 vector fragment, creating pSheB1 intermediate 2. Vector pSheB1 intermediate 2 was then digested with Bsp Lu11I and Pac I. The digested vector was purified by 1% agarose gel electrophoresis in TBE buffer, excised from the gel, and agarose-extracted using a QIAQUICK® Gel Extraction Kit.

The *Fusarium oxysporum* phospholipase gene fragment was also generated by PCR using pMSTR19 as template. The following PCR primers were used to introduce a Sph I site at the 5' end and a Pac I site at the 3' end of the gene:

```
                                      (SEQ ID NO: 77)
5'-GGGGGCATGCTTCTTCTACCACTCC-3'
        Sph I (SEQ ID NO: 78)
5'-GGGGTTAATTAAGAGCGGGCCTGGTTA-3'
       Pac I
```

The conditions for PCR and purification were performed as above. The phospholipase gene fragment was cloned into pCR®-TOPO® according to the manufacturer's instructions. The pCR®-TOPO® phospholipase clone was then digested with Sph I and treated with T4 DNA polymerase to remove the protruding 3' termini. The fragment was purified using QIAQUICK® Nucleotide Removal Kit and digested with Pac I. The digestion was purified by 1% agarose gel electrophoresis in TBE buffer and a 1 kb band was excised from the gel and purified using a QIAQUICK® Gel Extraction Kit.

Figure 24:
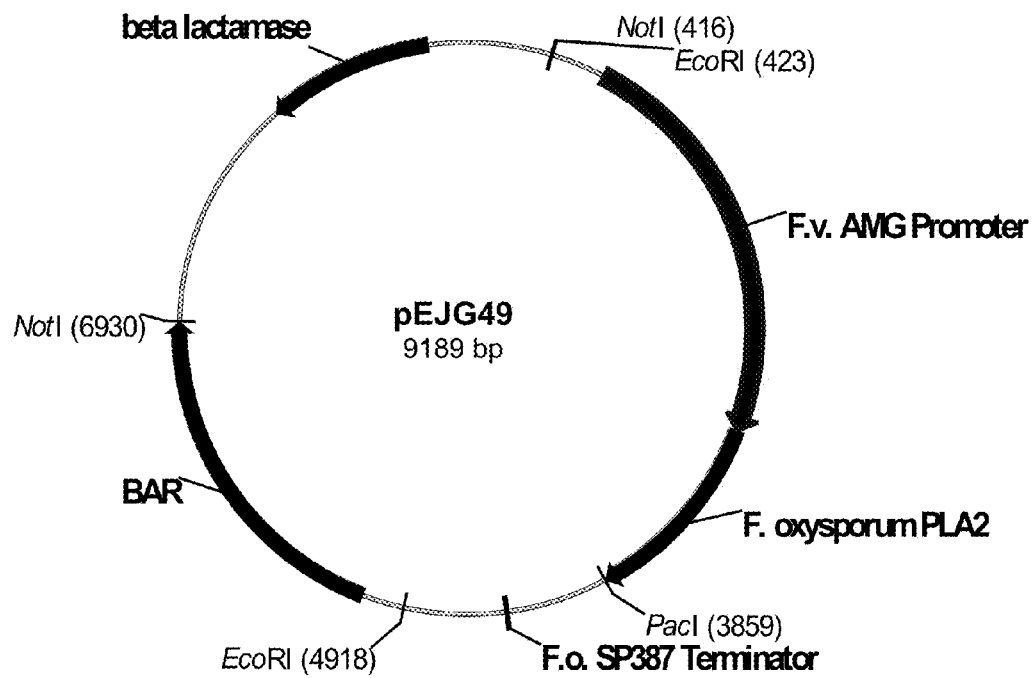
FIG. 24 shows a restriction map of pEJG49.

Plasmid pSheb1 intermediate 2 (above) was digested with Stu I and Bsp Lu11I and purified using a QIAQUICK® Nucleotide Removal Kit. The fragment was then ligated to a 2 kb Stu I-Bsp Lu11I *Fusarium venenatum* glucoamylase promoter fragment (WO 2000/056900). This vector, known as pSheb1 intermediate 3, was digested with Bsp Lu11I, treated with Klenow fragment to fill in the 5' overhang, digested with Pac I, and purified using a QIAQUICK® Nucleotide Removal Kit. The fragment was then ligated to the Sph I, blunt-Pac I *Fusarium oxysporum* phospholipase fragment (described above). The resulting vector, designated pEJG49 (FIG. 24), harbored the phospholipase reporter gene under the transcriptional control of the *Fusarium venenatum* glucoamylase promoter.

Example 22

Construction of Plasmid pEmY15

Site-directed mutagenesis was used to remove one of each of the Eco RI and Not I restriction sites from expression plasmid pEJG49 and render these restriction sites flanking the bialaphos resistance marker (bar gene) unique. The mutagenesis was completed using forward and reverse primers shown below and a QUIKCHANGE® Site-Directed Mutagenesis Kit.

```
Forward primer:
                                      (SEQ ID NO: 79)
5'-cctgcatggccgcCgccgcCaattcttacaaaccttcaacagtgg-3'

Reverse primer:
                                      (SEQ ID NO: 80)
5'-ccactgttgaaggtttgtaagaattGgcggcGgcggccatgcagg-3'
```

Figure 25:
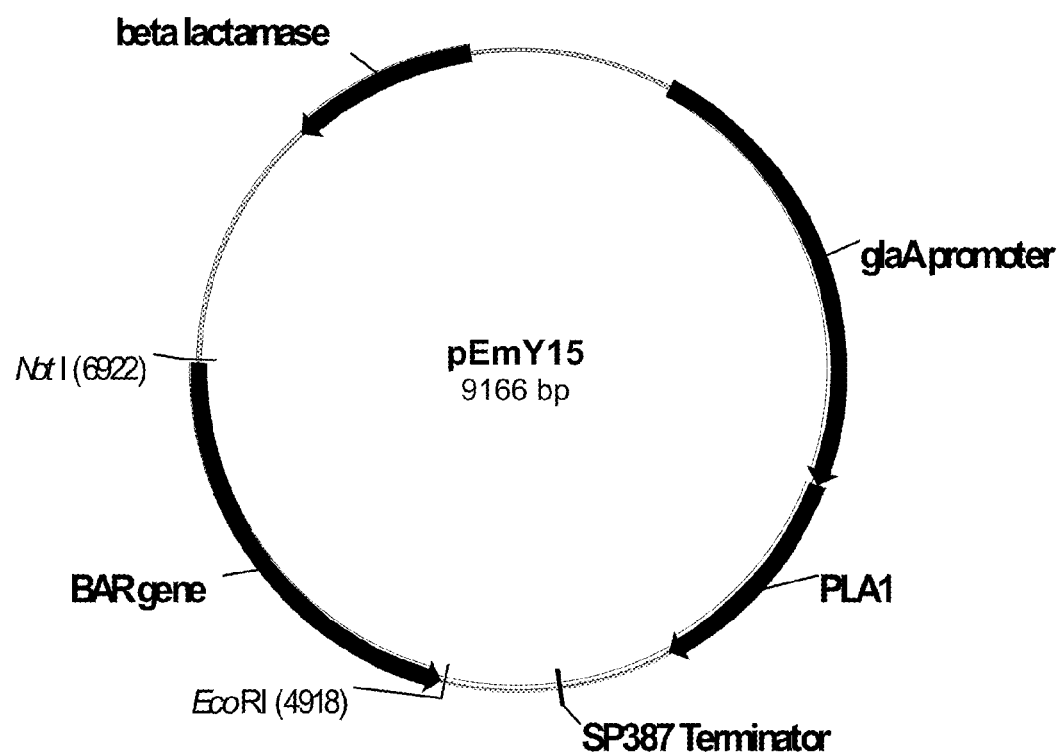
FIG. 25 shows a restriction map of pEmY15.

The uppercase letters indicate the desired changes and the resulting plasmid was designated pEmY15 (FIG. 25).

Example 23

Construction of Plasmid pEmY24

In order to replace the bar gene in expression plasmid pEmY15 with the *Fusarium venenatum* pyrG gene, the following protocol was performed. Plasmid pEmY15 was digested with Eco RI and Not I and purified by 1% agarose gel electrophoresis in TAE buffer. A 7.1 kb fragment was excised and agarose extracted using a QIAQUICK® Gel Extraction Kit.

A 2.3 kb fragment of the pyrG gene was PCR amplified from pDM156.2 using forward and reverse primers shown below.

```
Forward primer:
                                    (SEQ ID NO: 81)
5'-ATAAGAATgcggccgcTCCAAGGAATAGAATCACT-3'

Reverse primer:
                                    (SEQ ID NO: 82)
5'-CGgaattcTGTCGTCGAATACTAAC-3'
```

The bold sequence corresponds to an introduced Not I site and Eco RI site for the forward and reverse primers, respectively.

The amplification reaction was composed of 1× ThermoPol Buffer (New England Biolabs, Ipswich, Mass., USA), 200 µM dNTPs, 31 ng of pDM156.2, 1 µM each primer, and 1 unit of VENT® DNA polymerase in a final volume of 50 µl.

The reaction was incubated in an EPPENDORF® MASTERCYCLER® programmed for 1 cycle at 95° C. for 3 minutes; 30 cycles each at 95° C. for 30 seconds, 55° C. for 1 minute; and 72° C. for 3 minutes; and 1 cycle at 72° C. for 7 minutes.

Figure 26:
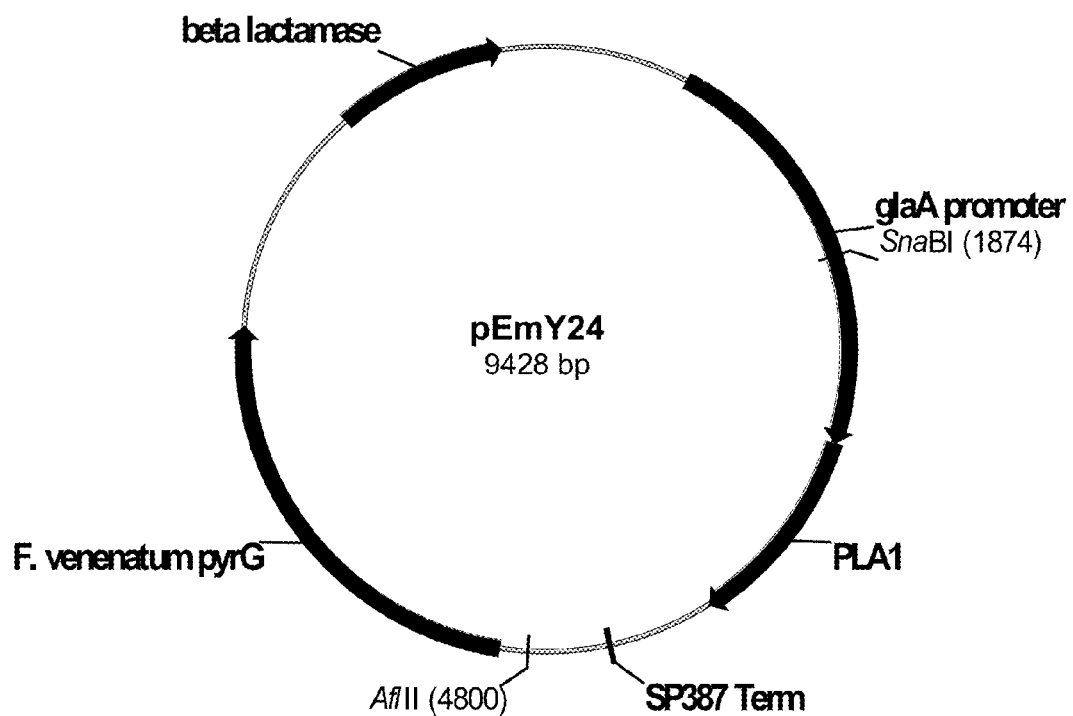
FIG. 26 shows a restriction map of pEmY24.

PCR products were isolated by 1% agarose gel electrophoresis in TAE buffer and a 2.3 kb fragment was excised and agarose-extracted using a MINELUTE® Gel Extraction Kit. The fragment was then digested with Eco RI and Not I and the digestion reaction purified using a MINELUTE® Reaction Cleanup Kit. The fragment was ligated to Not I/Eco RI-digested pEmY15 using T4 DNA ligase according to the manufacturer's instructions. The ligation mixture was transformed into E. coli XL1-Blue sub-cloning-grade competent cells (Stratagene, La Jolla, Calif., USA) according to the manufacturer's instructions. Transformants were sequenced to insure the absence of PCR errors and a plasmid was identified containing an error-free pyrG fragment. The resulting plasmid was designated pEmY24 (FIG. 26).

Example 24

Construction of Plasmid pDM257

Plasmid pEmY24 (Example 23) was digested with Afl II and Sna BI. A 6.5 kb fragment was purified by 1% agarose gel electrophoresis in TAE buffer, excised from the gel, and agarose-extracted using a QIAQUICK® Gel Extraction Kit. Plasmid pEJG65 was digested with Afl II and Sna BI. A 3.3 kb fragment was purified by 1% agarose gel electrophoresis in TAE buffer, excised from the gel, and agarose-extracted using a QIAQUICK® Gel Extraction Kit.

Figure 27:
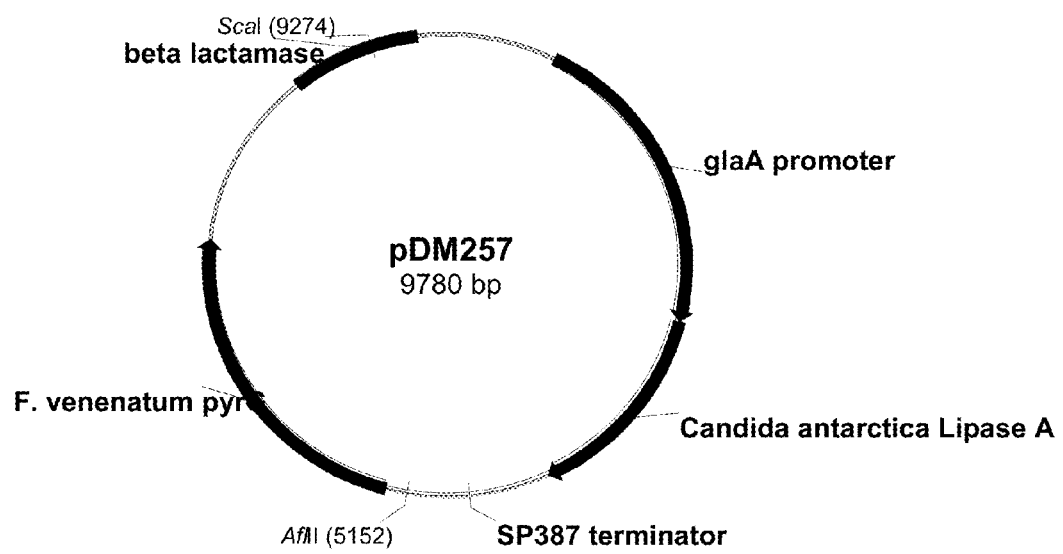
FIG. 27 shows a restriction map of pDM257.

The two fragments were ligated together using T4 DNA ligase according to the manufacturer's instructions. The ligation mixture was transformed into E. coli XL1-Blue sub-cloning-grade competent cells according to the manufacturer's instructions. Transformants were screened by sequence analysis and a clone was identified containing a plasmid with the desired fragments. The resulting plasmid was designated pDM257 (FIG. 27).

Example 25

Construction of Plasmid pDM258

Plasmid pDM257 was digested with Sca I and Afl II and purified by 1% agarose gel electrophoresis in TAE buffer and a 4.1 kb fragment was excised from the gel and agarose-extracted using a QIAQUICK® Gel Extraction Kit. Plasmid pEJG69 was also digested with Sca I and Afl II and purified by 1% agarose gel electrophoresis in TAE buffer and a 5.8 kb fragment was excised from the gel and agarose-extracted as above.

Figure 28:
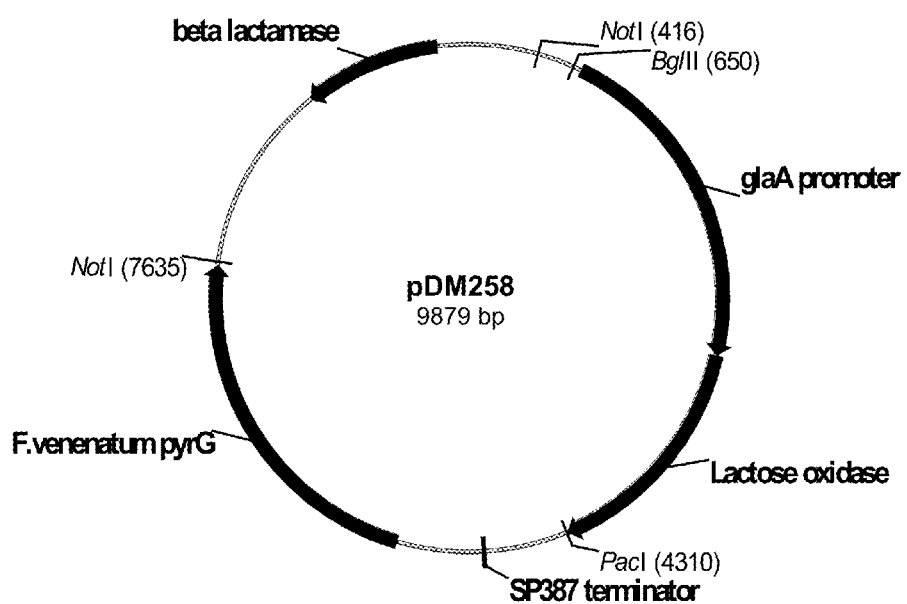
FIG. 28 shows a restriction map of pDM258.

The two fragments were ligated together using T4 DNA ligase according to the manufacturer's instructions. The ligation mixture was transformed into E. coli XL1-Blue sub-cloning-grade competent cells according to the manufacturer's instructions. Transformants were screened by sequence analysis and the desired plasmid was identified and designated pDM258 (FIG. 28).

Example 26

Expression of Lactose Oxidase in *Fusarium venenatum* Strain JfyS1643-95-4

Protoplasts of *Fusarium venenatum* JfyS1643-95-04 (Δtri5 ΔpyrG ΔamyA) were generated as described in Example 1. The protoplasts were then transformed according to the procedure described in Example 1 with pDM258, harboring the *Microdochium nivale* lactose oxidase expression vector, to evaluate the expression potential of the *Fusarium venenatum* JfyS1643-95-04 strain. Transformants were grown in shake flasks as described in Example 21 except that the flasks were incubated for five days at 28° C. with shaking at 200 rpm.

The shake flask broths were assayed for lactose oxidase activity using an activity assay in conjunction with a BIOMEK® 3000, (Beckman Coulter, Inc, Fullerton, Calif., USA). The lactose oxidase assay was a modified version of the Glucose Oxidase Assay Procedure (K-Glox) (Megazyme, Wicklow, Ireland). Culture supernatants were diluted appropriately in 0.1 M MOPS buffer pH 7.0 (sample buffer) followed by a series dilution from 0-fold to 1/3-fold to 1/9-fold of the diluted sample. A lactose oxidase standard (Novozymes A/S, Bagsvaerd, Denmark) was diluted using 2-fold steps starting with a 0.056 mg/ml concentration and ending with a 0.007 mg/ml concentration in the sample buffer. A total of 20 µl of each dilution including standard was transferred to a 96-well flat bottom plate. One hundred microliters of a POD solution (Peroxidase, 4AA, stabilizers in potassium phosphate buffer pH 7 plus p-hydroxybenzoic acid and sodium azide) were added to each well followed by addition of 100 µl of glucose substrate (0.5 M glucose in sample buffer). The rate of reaction was measured at ambient temperature (approximately 26° C.) at 510 nm for a total of 10 minutes. Sample concentrations were determined by extrapolation from a standard curve generated using lactose oxidase as a standard. The highest producing lactose oxidase transformants were selected for growth and analysis in 2 liter fermenters.

The fermentation medium (pH 6) was composed per liter of 20 g of soya flour, 20 g of sucrose, 2.0 g of $MgSO_4 \cdot 7H_2O$, 2.0 g of anhydrous $KH_2PO_4$, 2.0 g of $K_2SO_4$, 5.0 g of $(NH_4)_2SO_4$, 1.0 g of citric acid, 0.5 ml of 200×AMG trace metals solution (no nickel), and 0.5 ml of pluronic acid with a 20% maltose feed. The fermentations were run at 29.0+/−1.0° C., 1200 rpm, and 1.0 vvm aeration where % DO was maintained above 30%.

Fermentation broths were assayed for alpha-amylase activity using an Alpha-Amylase Assay Kit (Megazyme International Ireland Ltd., Wicklow, Ireland) in conjunction with a BIOMEK® 3000 and BIOMEK® NX (Beckman Coulter, Inc, Fullerton Calif., USA). Fermentation broths were assayed for lactose oxidase activity as described above.

Figure 29:
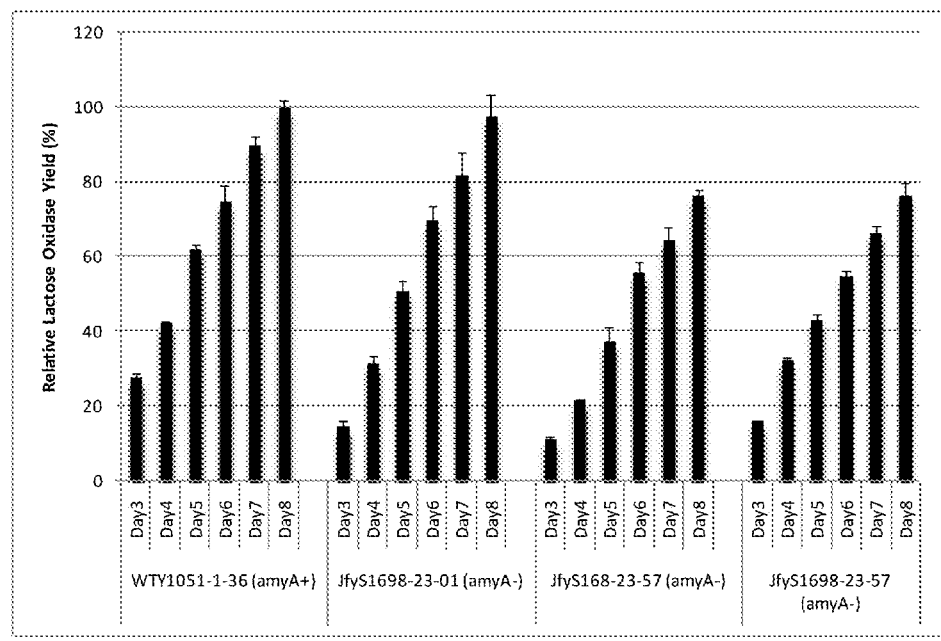
FIG. 29 shows the relative lactose oxidase yields of transformants of *Fusarium venenatum* JfyS1643-95-04 (Δtri5 ΔpyrG ΔamyA).
Figure 30:
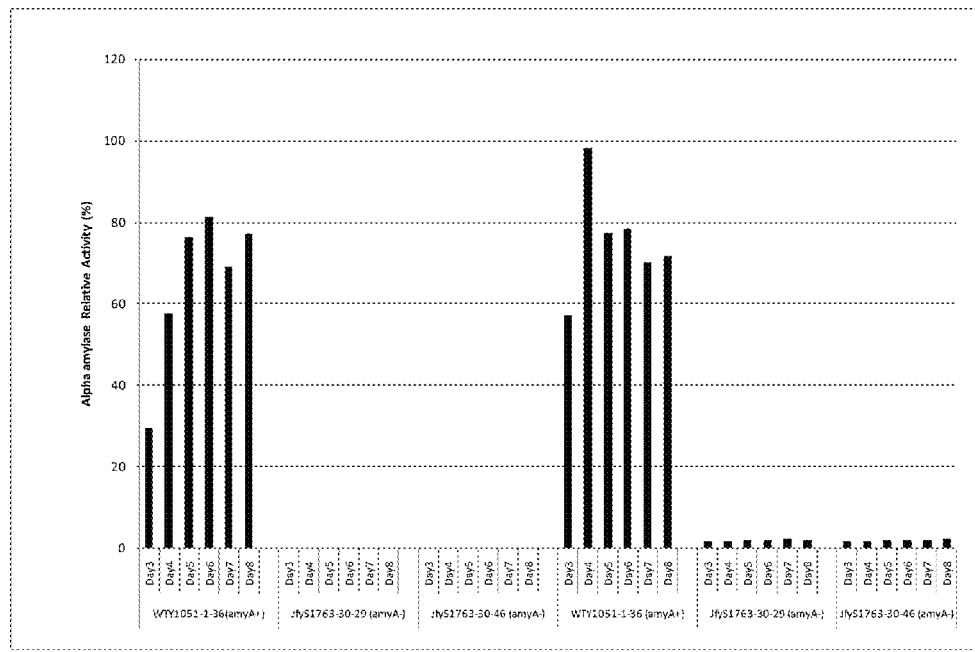
FIG. 30 shows the relative alpha-amylase activity of transformants of transformants of *Fusarium venenatum* JfyS1643-95-04 (Δtri5 ΔpyrG ΔamyA).

The resulting top transformant, *Fusarium venenatum* JfyS1643-95-04, had equivalent lactose oxidase production levels to other *Fusarium venenatum* transformants without the deletions in 2 liter fermenters (FIG. 29) indicating that deletion of the amyA gene did not have a negative impact on heterologous protein production. The deletion did, however, abolish alpha-amylase activity in the culture broth of this strain and all later strains in this lineage (FIG. 30). Since this transformant had equivalent heterologous protein production capacity to the current production strain, and reduced alpha-amylase levels during fermentation, *Fusarium venenatum* JfyS1643-95-04 host strain was selected for deletion of an alkaline protease A gene (alpA).

Example 27

Generation of the *Fusarium venenatum* Alkaline Protease A (alpA) Deletion Vector pJfyS1698-72-10

Upstream flanking sequence for use in the complete removal of the *Fusarium venenatum* A3/5 alkaline protease A (alpA) gene (SEQ ID NO: 83 for the DNA sequence and SEQ ID NO: 84 for the deduced amino acid sequence) was obtained using a GENOME WALKER™ Universal Kit. Each library generated with the kit was subjected to two rounds of PCR for the 5' flanking sequence using a 5' gene-specific primer and a 5' nested primer shown below.

```
5' gene-specific primer:
                                    (SEQ ID NO: 85)
5'-GAGGAATTGGATTTGGATGTGTGTGGAATA-3'

5' nested primer:
                                    (SEQ ID NO: 86)
5'-GGAGTCTTTGTTCCAATGTGCTCGTTGA-3'
```

Sequence information was obtained from the PCR product using a Nested Adaptor Primer supplied with the GENOME WALKER™ Universal Kit and the 5' nested primer above. The obtained sequence was used to design primers to amplify a 1 kb region of the 5' alpA flanking sequence for insertion into the empty deletion vector pJfyS1579-41-11

The alpA 5' flanking sequence was PCR amplified from *Fusarium venenatum* A3/5 genomic DNA using region-specific forward and reverse primers shown below. The underlined letters represent a Not I site, for later removal of the pCR®2.1 portion of the vector, and the italicized letters represent an Asc I site for vector cloning.

```
Forward primer:
                                    (SEQ ID NO: 87)
5'-aaaaaaggcgcgccgcggccgcGTTACGGTGTTCAAGTACAT
CTTACA-3'

Reverse primer:
                                    (SEQ ID NO: 88)
5'-aaaaaaggcgcgccATTGCTATCATCAACTGCCTTTCTT-3'
```

The amplification reaction contained 1× HERCULASE® Reaction Buffer, 120 ng of genomic DNA, 400 nm primers, 200 μM dNTPs, and 2.5 units of HERCULASE® DNA polymerase.

The amplification reaction was incubated in an EPPENDORF® MASTERCYCLER® programmed for 1 cycle at 95° C. for 2 minutes; 20 cycles each at 94° C. for 30 seconds, 56° C. for 30 seconds, and 72° C. for 1 minute 10 seconds; and 1 cycle at 72° C. for 7 minutes.

Figure 31:
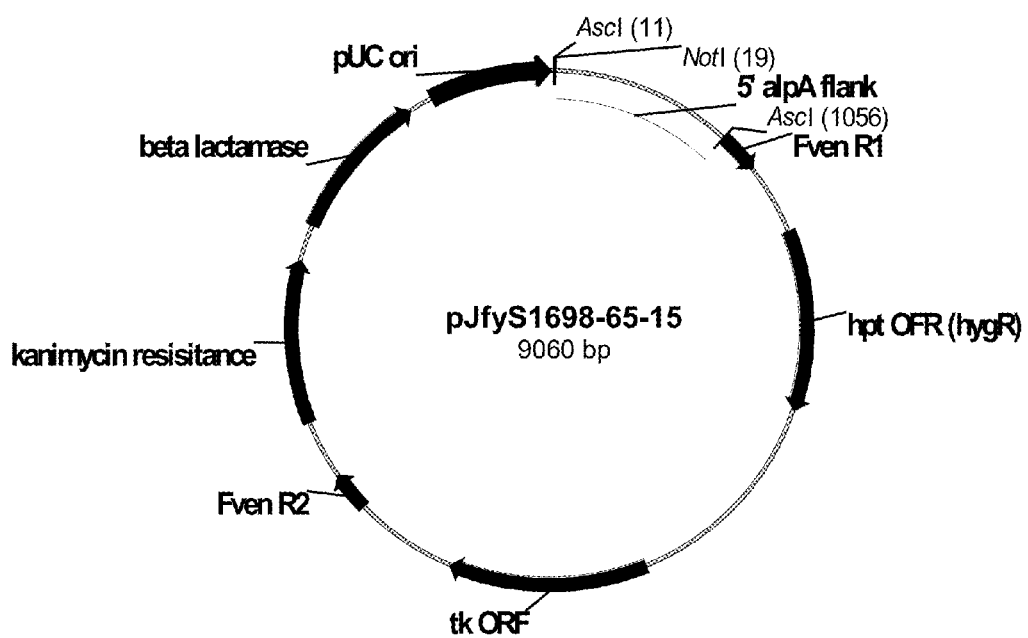
FIG. 31 shows a restriction map of pJfyS1698-65-15.

A 5 μl portion of the amplified reaction was visualized by 1% agarose gel electrophoresis using TAE buffer to insure the reaction had produced the desired 1 kb band. The insert was then directly cloned into pCR®2.1 from the amplification reaction using a TOPO® TA Cloning Kit according to the manufacturer's instructions. Transformants were screened by restriction analysis with Eco RI to insure the presence of the insert and 5 correct preparations were combined. The insert was liberated from pCR®2.1 by digestion with Asc I and the fragment was purified by agarose gel electrophoresis as described above. The insert was cloned into Asc I-linearized pJfyS1579-41-11 using a QUICK LIGATION™ Kit and the ligation mixture used to transform *E. coli* SURE® chemically competent cells according to the manufacturer's protocol. Transformants were screened by sequence analysis to insure the absence of PCR errors. One plasmid containing the flanking sequence without errors was designated pJfyS1698-65-15 (FIG. 31) and used to insert the 3' flanking sequence.

The 3' flanking sequence of the alpA gene was amplified from *Fusarium venenatum* A3/5 genomic DNA using region specific forward and reverse primers shown below. The underlined letters represent a Not I site, for later beta-lactamase removal, and the italicized letters represent a Sbf I site for vector cloning.

```
Forward primer:
                                    (SEQ ID NO: 89)
5'-aaaaacctgcaggGGATGTGTGTGGAATAGGATATG-3'

Reverse primer:
                                    (SEQ ID NO: 90)
5'-aaaaacctgcagggcggccgcCCTCAAGGTGGAGAAATAATCTGT-3'
```

The PCR reaction contained 1× HERCULASE® Reaction Buffer, 120 ng of genomic DNA template, 400 nm primers, 200 μM dNTPs, and 2.5 units of HERCULASE® DNA polymerase.

The amplification reaction was incubated in an EPPENDORF® MASTERCYCLER® programmed for 1 cycle at 95° C. for 2 minutes; 20 cycles each at 94° C. for 30 seconds, 56° C. for 30 seconds, and 72° C. for 1 minute 10 seconds; and 1 cycle at 72° C. for 7 minutes.

A 5 μl portion of the amplified reaction was visualized on a 1% agarose gel in TAE buffer to insure the reaction had produced the desired 1 kb band. The 1 kb insert, directly from the PCR reaction, was then cloned into pCR®2.1 using a TOPO® TA Cloning Kit. The resulting plasmid was sequenced to identify a colony containing the correct sequence. The fragment was then liberated from this plasmid by Sbf I digestion and purified by 1% agarose gel electrophoresis in TAE buffer. A 1 kb band was excised and agarose-extracted using a MINELUTE® Gel Extraction Kit.

Figure 32:
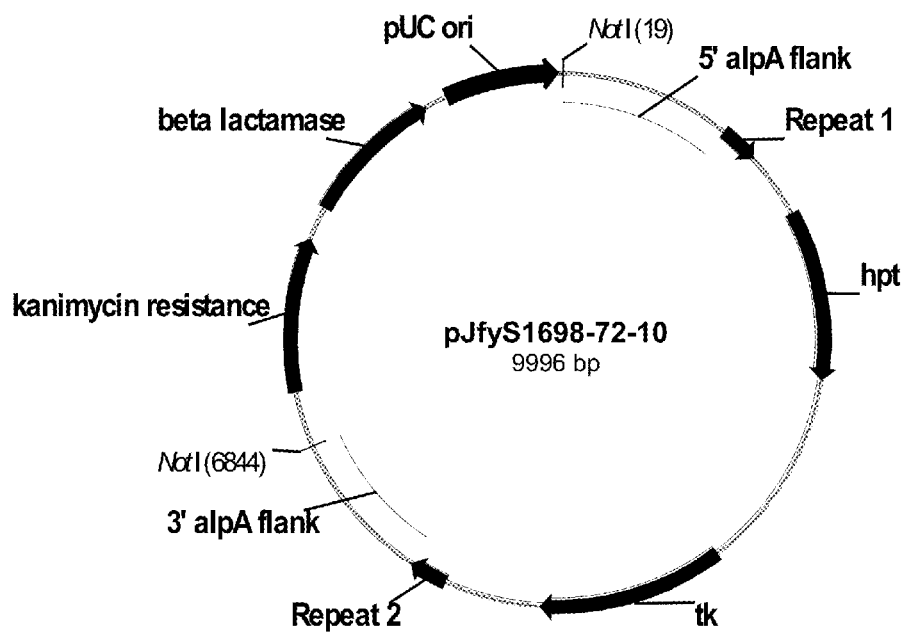
FIG. 32 shows a restriction map of pJfyS1698-72-10.

This fragment was then ligated to Sbf I linearized pJfyS1698-65-15 (treated with calf intestine phosphatase) using a QUICK LIGATION™ Kit and the ligation mixture was used to transform *E. coli* SURE® chemically competent cells according to the manufacturer's instructions. Transformants were screened by restriction analysis with Not I to insure the fragment had been inserted in the correct orientation and sequenced to insure no deviations from the expected sequence. The resulting plasmid pJfyS1698-72-10 (FIG. 32) was used for deletion of the alpA gene.

Example 28

Generation of Δtri5 ΔpyrG ΔamyA ΔalpA *Fusarium venenatum* Strain JfyS1763-11-1

Three transformants of *Fusarium venenatum* JfyS1643-95-4 (Δtri5 ΔpyrG ΔamyA) (Example 16) transformed with Not I-digested and gel-purified pJfyS1698-72-10 according to the procedure described in Example 1 were transferred from transformation plates with sterile toothpicks to new plates containing VNO$_3$RLMT medium supplemented with 125 μg of hygromycin B per ml and 10 mM uridine and incubated at room temperature for 7 days. For Southern analysis, 2 μg of *Fusarium venenatum* genomic DNA from each of the 3 transformants were digested with 34 units of Sph I. A DIG probe to the 5' flanking sequence of the alpA gene was generated according to the method described in Example 11 using the forward and reverse primers shown below.

```
Forward primer:
                                    (SEQ ID NO: 91)
5'-GCACGTTAGGCTCAAGCCAGCAAGG-3'

Reverse primer:
                                    (SEQ ID NO: 92)
5'-GAGGCTCATGGATGTGGCGTTAATG-3'
```

Southern analysis performed as described in Example 11 indicated that one of the three transformants contained a single copy of the deletion cassette at the alpA gene locus and this transformant was designated *Fusarium venenatum* JfyS1698-83-2.

*Fusarium venenatum* JfyS1698-83-2 was sporulated as described in Example 1 and 10$^5$ spores were plated onto a 150 mm diameter plate containing VNO$_3$RLMT medium supplemented with 50 μM FdU and 0.1 mM uridine. Spore isolates obtained were sub-cultured to a new plate containing VNO$_3$RLMT medium supplemented with 10 μM FdU and 0.1 mM uridine. The resulting spore isolates were analyzed by Southern analysis as described in Example 2 and one spore isolate was identified that had correctly excised the cassette. The isolate was designated *Fusarium venenatum* JfyS1698-94-04. *Fusarium venenatum* JfyS1698-94-04 was spore-purified once as described in Example 11 and one spore isolate was picked and designated *Fusarium venenatum* JfyS1763-11-01 (Δtri5 ΔpyrG ΔamyA ΔalpA).

Protoplasts of *Fusarium venenatum* JfyS1763-11-01 were generated and transformed as described in Example 1 with pDM258. Transformants were analyzed as described in Example 26 and shake flask broths were assayed for alkaline protease activity. A PROTAZYME® AK tablet (Megazyme, Wicklow, Ireland) was suspended in 2.0 ml of 0.01% TRITON® X-100 by gentle stirring. Five hundred microliters of this suspension and 500 μl of assay buffer supplied with the PROTAZYME® AK tablet were mixed in an EPPENDORF® tube and placed on ice. Twenty microliters of protease sample (diluted in 0.01% TRITON® X-100) were added. The assay was initiated by transferring the EPPENDORF® tube to an EPPENDORF® thermomixer, which was set to the assay temperature. The tube was incubated for 15 minutes on the EPPENDORF® thermomixer at 1300 rpm. The incubation was stopped by transferring the tube back to an ice bath. Then the tube was centrifuged at 16,000×g in an ice cold centrifuge for a few minutes and 200 μl of supernatant was transferred to a microtiter plate. The absorbance at 650 nm was read as a measure of protease activity.

Figure 33:
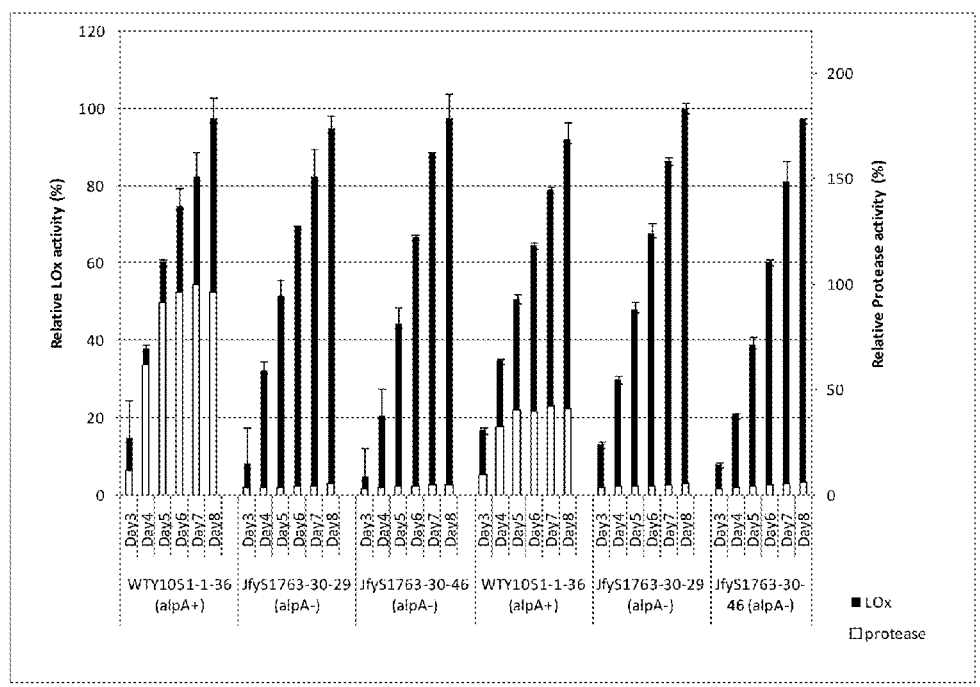
FIG. 33 shows the relative alkaline protease activity of transformants of *Fusarium venenatum* JfyS1763-11-01 (Δtri5 ΔpyrG ΔamyA ΔalpA).

As with the amyA deletion, deletion of the alpA gene did not have a positive impact on lactose oxidase expression. However, the alkaline protease side activity in the fermentation supernatants was reduced 10-fold (FIG. 33).

Example 29

Generation of the dps1 Deletion Vector pJfyS111

The 3' flanking sequence for the *Fusarium venenatum* depsipeptide synthase (dps1) gene (SEQ ID NO: 93 for the DNA sequence and SEQ ID NO 94 for the deduced amino acid sequence) was PCR amplified from *Fusarium venenatum* JfyS1763-11-01 genomic DNA using the forward and reverse primers shown below. The underlined portion in the primer represents the introduced Sbf I site for cloning and the italicized portion corresponds to an introduced Not I site for later beta-lactamase removal.

```
Forward primer:
                                    (SEQ ID NO: 95)
5'-GACTAAGCCCTGCAGGTTGGTCTCAATCGTCGCGACAG-3'

Reverse primer:
                                    (SEQ ID NO: 96)
5'-AGTCTACCCCTGCAGGCGGCCGCTGGCATCGGTGGACGTAA
CACGC-3'
```

The amplification reaction contained 1× HERCULASE® Reaction Buffer, 400 nM each primer, 200 μM dNTPs, 100 ng of genomic DNA, and 1.5 units of HERCULASE® DNA polymerase in a final volume of 50 μl. The amplification reaction was incubated in an EPPENDORF® MASTERCYCLER® programmed for 1 cycle at 95° C. for 2 minutes; 25 cycles each at 95° C. for 30 seconds, 57° C. for 30 seconds, and 72° C. for 1 minute and 20 seconds; and 1 cycle at 72° C. for 7 minutes.

Figure 34:
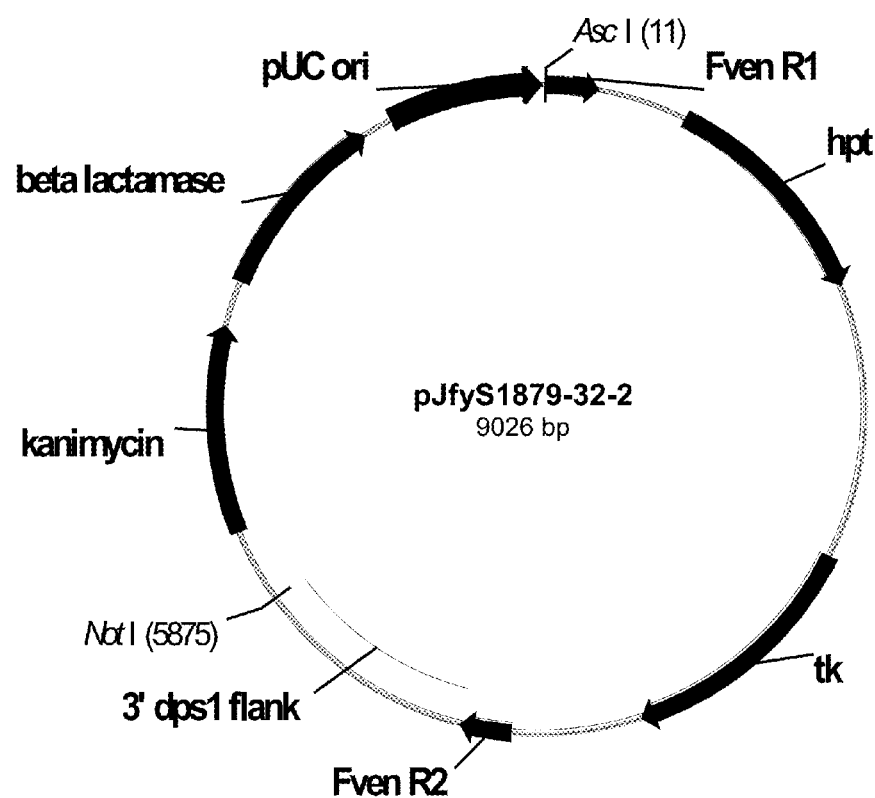
FIG. 34 shows a restriction map of pJfyS1879-32-2.

The amplification reaction was purified using a MINELUTE® PCR Purification Kit. The purified reaction was then digested with Sbf I and submitted to 1% agarose gel electrophoresis using TAE buffer. A 1 kb band was excised from the gel and agarose-extracted using a MINELUTE® Gel Extraction Kit. The digested vector was then ligated to Sbf I-digested pJfyS1579-41-11 (Example 12) (which had been dephosphorylated with calf intestine phosphatase) using a QUICK LIGATION™ Kit according to the manufacturer's suggested protocols. Resulting clones were analyzed by restriction analysis with Eco RI (to check for insert presence and orientation) and sequence analysis (to insure the absence of PCR errors), and the resulting plasmid was designated pJfyS1879-32-2 (FIG. 34).

In order to obtain flanking sequence on the 5' end of the dps1 gene, a GENOME WALKER™ Universal Kit was used as described in Example 15 with gene-specific and gene-specific nested primers shown below.

```
Gene-Specific primer:
                                      (SEQ ID NO: 97)
5'-GCTATTGAGGGGACTATCTCCATGACTACA-3'

Gene-Specific nested primer:
                                      (SEQ ID NO: 98)
5'-GCCTACCATCGACAGCAGTAAGATATTCC-3'
```

The 5' dps1 flanking sequence was amplified from *Fusarium venenatum* JfyS1763-11-1 genomic DNA using forward and reverse primers indicated below. The underlined portion in the forward primer represents an introduced Asc I site for cloning and the italicized portion corresponds to an introduced Not I site for later beta-lactamase removal. The amplification reaction and cycling parameters were identical to those described above except the primers used were those below, the annealing temperature used was 53° C., and the extension time was 1 minute and 15 seconds.

```
Forward primer:
                                      (SEQ ID NO: 99)
5'-ATGTGCTACAGGCGCGCCGCGGCCGCGAGTTCCAACATGTCTTA
TTATCC-3'

Reverse primer:
                                      (SEQ ID NO: 100)
5'-TACTGTACCGGCGCGCCATCTGAGCCAAGAGACTCATTCAT-3'
```

Figure 35:
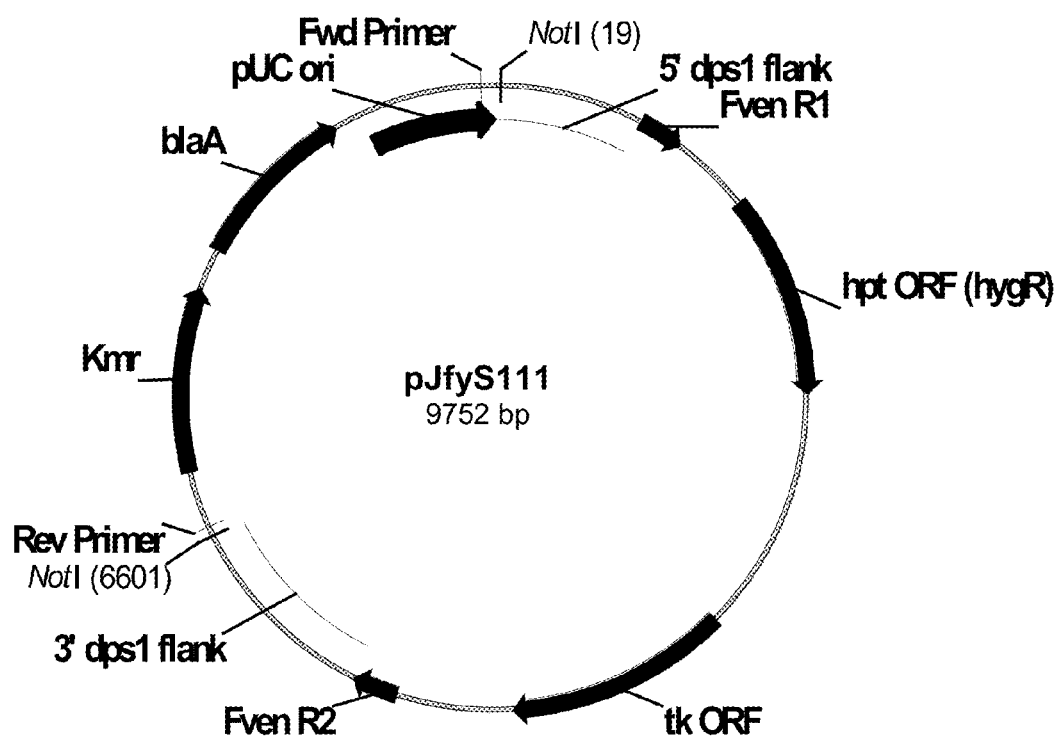
FIG. 35 shows a restriction map of pJfyS111.

The PCR reaction was purified using a MINELUTE® PCR Purification Kit. The purified reaction was digested with Asc I, and subjected to 1% agarose gel electrophoresis using TAE buffer. A 0.7 kb band was excised from the gel and agarose-extracted as described above. The 0.7 kb band was ligated to pJfyS1879-32-2 (digested with Asc I and dephosphorylated with calf intestine phosphatase) using a QUICK LIGATION™ Kit. Resulting clones were analyzed by sequence analysis to insure the absence of PCR errors, and the resulting plasmid was designated pJfyS111 (FIG. 35) and used to delete the *Fusarium venenatum* dps1 gene.

Example 30

Generation of Δtri5 ΔpyrG ΔamyA ΔalpA Δdps1 *Fusarium venenatum* Strain JfyS1879-57-01

When *Fusarium venenatum* JfyS1763-11-01 protoplasts were transformed with Not I-digested and gel-purified pJfyS111 (according to the procedure described in Example 1), 77 transformants were obtained. Of those 48 were transferred from transformation plates with sterile toothpicks to new plates containing $VNO_3RLMT$ medium supplemented with 125 μg of hygromycin B per ml and 10 mM uridine and incubated at room temperature for 7 days.

Fungal biomass was produced by inoculating 25 ml of M400 medium supplemented with 10 mM uridine with four 1 cm agar plugs from 7 day old transformants generated as described in Example 1. The cultures were incubated for 3 days at 28° C. with shaking at 150 rpm. Agar plugs were removed and the cultures were filtered through MIRACLOTH™. Harvested biomass was frozen with liquid nitrogen and the mycelia were ground using a mortar and pestle.

Genomic DNA was isolated using a DNEASY® Plant Maxi Kit according to the manufacturer's instructions, except the lytic incubation period at 65° C. was extended to 1.5 hours from 10 minutes.

Two μg of genomic DNA were digested with 28 units each of Nco I and Spe I in a 50 μl reaction volume at 37° C. for 22 hours. The digestion was subjected to 1.0% agarose gel electrophoresis in TAE buffer. The DNA was fragmented in the gel by treating with 0.25 M HCl, denatured with 1.5 M NaCl-0.5 M NaOH, neutralized with 1.5 M NaCl-1 M Tris pH 8, and then transferred in 20×SSC to a NYTRAN® Supercharge nylon membrane using a TURBOBLOTTER™ Kit. The DNA was UV cross-linked to the membrane using a UV STRATALINKER™ and pre-hybridized for 1 hour at 42° C. in 20 ml of DIG Easy Hyb.

A DIG probe to the 3' flanking sequence of the dps1 gene was generated according to the method described in Example 11 using the forward and reverse primers shown below.

```
Forward primer:
                                        (SEQ ID NO: 101)
5'-CTTGACTATTATCTCACGTTGTCAG-3'

Reverse primer:
                                        (SEQ ID NO: 102)
5'-TCAAGTGTTGTGTAATGTTGGAACA-3'
```

Southern analysis performed as described in Example 11 indicated that three of the 8 transformants contained the deletion fragment in a single copy at the dps1 locus. One was named *Fusarium venenatum* JfyS1879-43-05.

Southern analysis indicated that three of the 8 transformants contained the deletion fragment in a single copy at the dps1 locus. One of these was named *Fusarium venenatum* JfyS1879-43-5.

*Fusarium venenatum* JfyS1879-43-5 was sporulated as described in Example 1 and $10^5$ spores were plated onto a 150 mm diameter plate containing $VNO_3RLMT$ medium supplemented with 50 μM FdU and 0.1 mM uridine. Spore isolates obtained were sub-cultured to new plates containing $VNO_3RLMT$ medium supplemented with 50 μM FdU and 0.1 mM uridine. The resulting spore isolates were analyzed by Southern analysis as described in Example 2 and one spore isolate was identified that had correctly excised the cassette. The isolate was designated *Fusarium venenatum* JfyS1879-52-3. *Fusarium venenatum* JfyS1879-52-3 was spore purified once as described in Example 11 and one spore isolate was picked and designated *Fusarium venenatum* JfyS1879-57-1 (Δtri5 ΔpyrG ΔamyA ΔalpA Δdps1).

The present invention is further described by the following numbered paragraphs:

[1] A method of producing a polypeptide, comprising:

(a) cultivating a mutant of a parent *Fusarium venenatum* strain in a medium for the production of the polypeptide, wherein the mutant strain comprises a polynucleotide encoding the polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions; and (b) recovering the polypeptide from the cultivation medium.

[2] The method of paragraph 1, wherein the mutant strain comprises a modification of a pyrG gene.

[3] The method of paragraph 1, wherein the mutant strain comprises a modification of an amyA gene.

[4] The method of paragraph 1, wherein the mutant strain comprises a modification of an alpA gene.

[5] The method of paragraph 1, wherein the mutant strain comprises a modification of a pyrG gene and an amyA gene.

[6] The method of paragraph 1, wherein the mutant strain comprises a modification of a pyrG gene and an alpA gene.

[7] The method of paragraph 1, wherein the mutant strain comprises a modification of an amyA gene and an alpA gene.

[8] The method of paragraph 1, wherein the mutant strain comprises a modification of a pyrG gene, an amyA gene, and an alpA gene.

[9] The method of any of paragraphs 1-8, wherein the mutant strain further comprises one or both of the genes tri5 and dps1, wherein the one or both of the genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

[10] The method of paragraph 9, wherein the mutant strain comprises a modification of a tri5 gene.

[11] The method of paragraph 9, wherein the mutant strain comprises a modification of a dps1 gene.

[12] The method of paragraph 9, wherein the mutant strain comprises a modification of a tri5 gene and a dps1 gene.

[13] The method of any of paragraph 9-12, wherein the mutant strain produces at least 25% less of the one or both enzymes of trichodiene synthase and cyclohexadepsipeptide synthetase compared to the parent *Fusarium venenatum* strain when cultivated under identical conditions.

[14] The method of any of paragraph 9-12, wherein the mutant strain is completely deficient in the one or both enzymes trichodiene synthase and cyclohexadepsipeptide synthetase compared to the parent *Fusarium venenatum* strain when cultivated under identical conditions.

[15] The method of any of paragraphs 1-14, wherein the polypeptide is native or foreign to the *Fusarium venenatum* strain.

[16] The method of paragraph 15, wherein the polypeptide is selected from the group consisting of an antigen, enzyme, growth factor, hormone, immunodilator, neurotransmitter, receptor, reporter protein, structural protein, and transcription factor.

[17] The method of paragraph 16, wherein the enzyme is an oxidoreductase, transferase, hydrolase, lyase, isomerase, or ligase.

[18] The method of any of paragraphs 1-17, wherein the mutant strain comprises at least two copies of the polynucleotide encoding the polypeptide.

[19] The method of any of paragraphs 1-18, wherein the mutant strain produces at least 25% less of the one or more (several) enzymes selected from the group consisting of orotidine-5'-monophosphate decarboxylase, alpha-amylase, and alkaline protease compared to the parent *Fusarium venenatum* strain when cultivated under identical conditions.

[20] The method of any of paragraphs 1-18, wherein the mutant strain is completely deficient in the one or more (several) enzymes selected from the group consisting of an orotidine-5'-monophosphate decarboxylase, alpha-amylase, and alkaline protease compared to the parent *Fusarium venenatum* strain when cultivated under identical conditions.

[21] The method of any of paragraphs 1-20, wherein the pyrG gene encoding a polypeptide having orotidine-5'-monophosphate decarboxylase activity is selected from the group consisting of:

(a) a gene encoding a polypeptide having orotidine-5'-monophosphate decarboxylase activity comprising an amino acid sequence having at least 60% sequence identity to SEQ ID NO: 44;

(b) a gene that hybridizes under at least low stringency conditions with (i) SEQ ID NO: 43 or its full-length complementary strand; and (c) a gene comprising a nucleotide sequence having at least 60% sequence identity to SEQ ID NO: 43.

[22] The method of paragraph 21, wherein the pyrG gene encodes a polypeptide having orotidine-5'-monophosphate decarboxylase activity comprising or consisting of SEQ ID NO: 44 or a fragment thereof having orotidine-5'-monophosphate decarboxylase activity.

[23] The method of any of paragraphs 1-20, wherein the amyA gene encoding a polypeptide having alpha-amylase activity is selected from the group consisting of:

(a) a gene encoding a polypeptide having alpha-amylase activity comprising an amino acid sequence having at least 60% sequence identity to SEQ ID NO: 52;

(b) a gene that hybridizes under at least low stringency conditions with (i) SEQ ID NO: 51 or its full-length complementary strand; and (c) a gene comprising a nucleotide sequence having at least 60% sequence identity to SEQ ID NO: 51.

[24] The method of paragraph 23, wherein the amyA gene encodes a polypeptide having alpha-amylase activity comprising or consisting of SEQ ID NO: 52 or a fragment thereof having alpha-amylase activity.

[25] The method of any of paragraphs 1-20, wherein the alpA gene encoding a polypeptide having alkaline protease activity is selected from the group consisting of:

(a) a gene encoding a polypeptide having alkaline protease activity comprising an amino acid sequence having at least 60% sequence identity to SEQ ID NO: 84;

(b) a gene that hybridizes under at least low stringency conditions with (i) SEQ ID NO: 83 or its full-length complementary strand; and (c) a gene comprising a nucleotide sequence having at least 60% sequence identity to SEQ ID NO: 83.

[26] The method of paragraph 25, wherein the alpA gene encodes a polypeptide having alkaline protease activity comprising or consisting of SEQ ID NO: 84 or a fragment thereof having alkaline protease activity.

[27] The method of any of paragraphs 1-20, wherein the tri5 gene encoding a polypeptide having trichodiene synthase activity is selected from the group consisting of:

(a) a gene encoding a polypeptide having trichodiene synthase activity comprising an amino acid sequence having at least 60% sequence identity to SEQ ID NO: 20;

(b) a gene that hybridizes under at least low stringency conditions with (i) SEQ ID NO: 19 or its full-length complementary strand; and (c) a gene comprising a nucleotide sequence having at least 60% sequence identity to SEQ ID NO: 19.

[28] The method of paragraph 27, wherein the tri5 gene encodes a polypeptide having trichodiene synthase activity comprising or consisting of SEQ ID NO: 20 or a fragment thereof having trichodiene synthase activity.

[29] The method of any of paragraphs 1-20, wherein the dps1 gene encoding a polypeptide having cyclohexadepsipeptide synthetase activity is selected from the group consisting of:

(a) a gene encoding a polypeptide having cyclohexadepsipeptide synthetase activity comprising an amino acid sequence having at least 60% sequence identity to SEQ ID NO: 94;

(b) a gene that hybridizes under at least low stringency conditions with (i) SEQ ID NO: 93 or its full-length complementary strand; and (c) a gene comprising a nucleotide sequence having at least 60% sequence identity to SEQ ID NO: 93.

[30] The method of paragraph 29, wherein the dps1 gene encodes a polypeptide having cyclohexadepsipeptide synthetase activity comprising or consisting of SEQ ID NO: 94 or a fragment thereof having cyclohexadepsipeptide synthetase activity.

[31] A mutant of a parent *Fusarium venenatum* strain, comprising a polynucleotide encoding a polypeptide and one or more (several) genes selected from the group consisting of pyrG, amyA, and alpA, wherein the one or more (several) genes are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

[32] The mutant strain of paragraph 31, which comprises a modification of a pyrG gene.

[33] The mutant strain of paragraph 31, which comprises a modification of an amyA gene.

[34] The mutant strain of paragraph 31, which comprises a modification of an alpA gene.

[35] The mutant strain of paragraph 31, which comprises a modification of a pyrG gene and an amyA gene.

[36] The mutant strain of paragraph 31, which comprises a modification of a pyrG gene and an alpA gene.

[37] The mutant strain of paragraph 31, which comprises a modification of an amyA gene and an alpA gene.

[38] The mutant strain of paragraph 31, which comprises a modification of a pyrG gene, an amyA gene, and an alpA gene.

[39] The mutant strain of any of paragraphs 31-38, which further comprises one or both of the genes tri5 and dps1, wherein the one or both of the genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

[40] The mutant strain of paragraph 39, which comprises a modification of a tri5 gene.

[41] The mutant strain of paragraph 39, which comprises a modification of a dps1 gene.

[42] The mutant strain of paragraph 39, which comprises a modification of a tri5 gene and a dps1 gene.

[43] The mutant strain of any of paragraphs 39-42, which produces at least 25% less of the one or both enzymes of trichodiene synthase and cyclohexadepsipeptide synthetase compared to the parent *Fusarium venenatum* strain when cultivated under identical conditions.

[44] The mutant strain of any of paragraphs 39-42, which is completely deficient in the one or both enzymes trichodiene synthase and cyclohexadepsipeptide synthetase compared to the parent *Fusarium venenatum* strain when cultivated under identical conditions.

[45] The mutant strain of any of paragraphs 31-44, wherein the polypeptide is native or foreign to the *Fusarium venenatum* strain.

[46] The mutant strain of any of paragraphs 31-45, wherein the polypeptide is selected from the group consisting of an antigen, enzyme, growth factor, hormone, immunodilator, neurotransmitter, receptor, reporter protein, structural protein, and transcription factor.

[47] The mutant strain of paragraph 46, wherein the enzyme is an oxidoreductase, transferase, hydrolase, lyase, isomerase, or ligase.

[48] The mutant strain of any of paragraphs 31-47, which produces at least 25% less of the one or more (several) enzymes selected from the group consisting of orotidine-5'-monophosphate decarboxylase, alpha-amylase, and alkaline protease compared to the parent *Fusarium venenatum* strain when cultivated under identical conditions.

[49] The mutant strain of any of paragraphs 31-47, which is completely deficient in the one or more (several) enzymes selected from the group consisting of an orotidine-5'-monophosphate decarboxylase, alpha-amylase, and alkaline protease compared to the parent *Fusarium venenatum* strain when cultivated under identical conditions.

[50] The mutant strain of any of paragraphs 31-49, wherein the pyrG gene encoding a polypeptide having orotidine-5'-monophosphate decarboxylase activity is selected from the group consisting of:

(a) a gene encoding a polypeptide having orotidine-5'-monophosphate decarboxylase activity comprising an amino acid sequence having at least 60% sequence identity to SEQ ID NO: 44;

(b) a gene that hybridizes under at least low stringency conditions with (i) SEQ ID NO: 43 or its full-length complementary strand; and (c) a gene comprising a nucleotide sequence having at least 60% sequence identity to SEQ ID NO: 43.

[51] The mutant strain of paragraph 50, wherein the pyrG gene encodes a polypeptide having orotidine-5'-monophosphate decarboxylase activity comprising or consisting of SEQ ID NO: 44 or a fragment thereof having orotidine-5'-monophosphate decarboxylase activity.

[52] The mutant strain of any of paragraphs 31-49, wherein the amyA gene encoding a polypeptide having alpha-amylase activity is selected from the group consisting of:

(a) a gene encoding a polypeptide having alpha-amylase activity comprising an amino acid sequence having at least 60% sequence identity to SEQ ID NO: 52;

(b) a gene that hybridizes under at least low stringency conditions with (i) SEQ ID NO: 51 or its full-length complementary strand; and (c) a gene comprising a nucleotide sequence having at least 60% sequence identity to SEQ ID NO: 51.

[53] The mutant strain of paragraph 52, wherein the amyA gene encodes a polypeptide having alpha-amylase activity comprising or consisting of SEQ ID NO: 52 or a fragment thereof having alpha-amylase activity.

[54] The mutant strain of any of paragraphs 31-49, wherein the alpA gene encoding a polypeptide having alkaline protease activity is selected from the group consisting of:

(a) a gene encoding a polypeptide having alkaline protease activity comprising an amino acid sequence having at least 60% sequence identity to SEQ ID NO: 84;

(b) a gene that hybridizes under at least low stringency conditions with (i) SEQ ID NO: 83 or its full-length complementary strand; and (c) a gene comprising a nucleotide sequence having at least 60% sequence identity to SEQ ID NO: 83.

[55] The mutant strain of paragraph 54, wherein the alpA gene encodes a polypeptide having alkaline protease activity comprising or consisting of SEQ ID NO: 84 or a fragment thereof having alkaline protease activity.

[56] The mutant strain of any of paragraphs 31-49, wherein the tri5 gene encoding a polypeptide having trichodiene synthase activity is selected from the group consisting of:
  (a) a gene encoding a polypeptide having trichodiene synthase activity comprising an amino acid sequence having at least 60% sequence identity to SEQ ID NO: 20;
  (b) a gene that hybridizes under at least low stringency conditions with (i) SEQ ID NO: 19 or its full-length complementary strand; and
  (c) a gene comprising a nucleotide sequence having at least 60% sequence identity to SEQ ID NO: 19.

[57] The mutant strain of paragraph 56, wherein the tri5 gene encodes a polypeptide having trichodiene synthase activity comprising or consisting of SEQ ID NO: 20 or a fragment thereof having trichodiene synthase activity.

[58] The mutant strain of any of paragraphs 31-49, wherein the dps1 gene encoding a polypeptide having cyclohexadepsipeptide synthetase activity is selected from the group consisting of:
  (a) a gene encoding a polypeptide having cyclohexadepsipeptide synthetase activity comprising an amino acid sequence having at least 60% sequence identity to SEQ ID NO: 94;
  (b) a gene that hybridizes under at least low stringency conditions with (i) SEQ ID NO: 93 or its full-length complementary strand; and
  (c) a gene comprising a nucleotide sequence having at least 60% sequence identity to SEQ ID NO: 93.

[59] The mutant strain of paragraph 58, wherein the dps1 gene encodes a polypeptide having cyclohexadepsipeptide synthetase activity comprising or consisting of SEQ ID NO: 94 or a fragment thereof having cyclohexadepsipeptide synthetase activity.

[60] The mutant strain of any of paragraphs 31-59, which comprises a polynucleotide encoding a polypeptide foreign to the mutant strain.

[61] A method for obtaining a mutant of a parent *Fusarium venenatum* strain, comprising:
  (a) modifying one or more (several) genes selected from the group consisting of pyrG, amyA, and alpA; and (b) identifying a mutant strain from step (a) wherein the one or more (several) genes selected from the group consisting of pyrG, amyA, and alpA are modified rendering the mutant strain deficient in the production of one or more (several) enzymes selected from the group consisting of orotidine-5'-monophosphate decarboxylase, alpha-amylase, and alkaline protease, respectively, compared to the parent *Fusarium venenatum* strain when cultivated under identical conditions.

[62] The method of paragraph 61, wherein the mutant strain comprises a modification of a pyrG gene.

[63] The method of paragraph 61, wherein the mutant strain comprises a modification of an amyA gene.

[64] The method of paragraph 61, wherein the mutant strain comprises a modification of an alpA gene.

[65] The method of paragraph 61, wherein the mutant strain comprises a modification of a pyrG gene and an amyA gene.

[66] The method of paragraph 61, wherein the mutant strain comprises a modification of a pyrG gene and an alpA gene.

[67] The method of paragraph 61, wherein the mutant strain comprises a modification of an amyA gene and an alpA gene.

[68] The method of paragraph 61, wherein the mutant strain comprises a modification of a pyrG gene, an amyA gene, and an alpA gene.

[69] The method of any of paragraphs 61-68, further comprising modifying one or both of the genes tri5 and dps1, rendering the mutant strain deficient in the production of one or both enzymes trichodiene synthase and cyclohexadepsipeptide synthetase, respectively, compared to the parent *Fusarium venenatum* strain when cultivated under identical conditions.

[70] The method of paragraph 69, wherein the mutant strain comprises a modification of a tri5 gene.

[71] The method of paragraph 69, wherein the mutant strain comprises a modification of a dps1 gene.

[72] The method of paragraph 69, wherein the mutant strain comprises a modification of a tri5 gene and a dps1 gene.

[73] The method of any of paragraphs 69-72, wherein the mutant strain produces at least 25% less of the one or both enzymes of trichodiene synthase and cyclohexadepsipeptide synthetase compared to the parent *Fusarium venenatum* strain when cultivated under identical conditions.

[74] The method of any of paragraphs 69-72, wherein the mutant strain is completely deficient in the one or both enzymes trichodiene synthase and cyclohexadepsipeptide synthetase compared to the parent *Fusarium venenatum* strain when cultivated under identical conditions.

[75] The method of any of paragraphs 61-74, wherein the mutant strain produces at least 25% less of the one or more (several) enzymes selected from the group consisting of orotidine-5'-monophosphate decarboxylase, alpha-amylase, and alkaline protease compared to the parent *Fusarium venenatum* strain when cultivated under identical conditions.

[76] The method of any of paragraphs paragraph 61-74, wherein the mutant strain is completely deficient in the one or more (several) enzymes selected from the group consisting of an orotidine-5'-monophosphate decarboxylase, alpha-amylase, and alkaline protease compared to the parent *Fusarium venenatum* strain when cultivated under identical conditions.

[77] The method of any of paragraphs 61-76, wherein the pyrG gene encoding a polypeptide having orotidine-5'-monophosphate decarboxylase activity is selected from the group consisting of:

(a) a gene encoding a polypeptide having orotidine-5'-monophosphate decarboxylase activity comprising an amino acid sequence having at least 60% sequence identity to SEQ ID NO: 44;

(b) a gene that hybridizes under at least low stringency conditions with (i) SEQ ID NO: 43 or its full-length complementary strand; and (c) a gene comprising a nucleotide sequence having at least 60% sequence identity to SEQ ID NO: 43.

[78] The method of paragraph 77, wherein the pyrG gene encodes a polypeptide having orotidine-5'-monophosphate decarboxylase activity comprising or consisting of SEQ ID NO: 44 or a fragment thereof having orotidine-5'-monophosphate decarboxylase activity.

[79] The method of any of paragraphs 61-76, wherein the amyA gene encoding a polypeptide having alpha-amylase activity is selected from the group consisting of:

(a) a gene encoding a polypeptide having alpha-amylase activity comprising an amino acid sequence having at least 60% sequence identity to SEQ ID NO: 52;

(b) a gene that hybridizes under at least low stringency conditions with (i) SEQ ID NO: 51 or its full-length complementary strand; and (c) a gene comprising a nucleotide sequence having at least 60% sequence identity to SEQ ID NO: 51.

[80] The method of paragraph 79, wherein the amyA gene encodes a polypeptide having alpha-amylase activity comprising or consisting of SEQ ID NO: 52 or a fragment thereof having alpha-amylase activity.

[81] The method of any of paragraphs 61-76, wherein the alpA gene encoding a polypeptide having alkaline protease activity is selected from the group consisting of:

(a) a gene encoding a polypeptide having alkaline protease activity comprising an amino acid sequence having at least 60% sequence identity to SEQ ID NO: 84;

(b) a gene that hybridizes under at least low stringency conditions with (i) SEQ ID NO: 83 or its full-length complementary strand; and (c) a gene comprising a nucleotide sequence having at least 60% sequence identity to SEQ ID NO: 83.

[82] The method of paragraph 81, wherein the alpA gene encodes a polypeptide having alkaline protease activity comprising or consisting of SEQ ID NO: 84 or a fragment thereof having alkaline protease activity.

[83] The method of any of paragraphs 61-76, wherein the tri5 gene encoding a polypeptide having trichodiene synthase activity is selected from the group consisting of:

(a) a gene encoding a polypeptide having trichodiene synthase activity comprising an amino acid sequence having at least 60% sequence identity to SEQ ID NO: 20;

(b) a gene that hybridizes under at least low stringency conditions with (i) SEQ ID NO: 19 or its full-length complementary strand; and (c) a gene comprising a nucleotide sequence having at least 60% sequence identity to SEQ ID NO: 19.

[84] The method of paragraph 83, wherein the tri5 gene encodes a polypeptide having trichodiene synthase activity comprising or consisting of SEQ ID NO: 20 or a fragment thereof having trichodiene synthase activity.

[85] The method of any of paragraphs 61-76, wherein the dps1 gene encoding a polypeptide having cyclohexadepsipeptide synthetase activity is selected from the group consisting of:

(a) a gene encoding a polypeptide having cyclohexadepsipeptide synthetase activity comprising an amino acid sequence having at least 60% sequence identity to SEQ ID NO: 94;

(b) a gene that hybridizes under at least low stringency conditions with (i) SEQ ID NO: 93 or its full-length complementary strand; and (c) a gene comprising a nucleotide sequence having at least 60% sequence identity to SEQ ID NO: 93.

[86] The method of paragraph 85, wherein the dps1 gene encodes a polypeptide having cyclohexadepsipeptide synthetase activity comprising or consisting of SEQ ID NO: 94 or a fragment thereof having cyclohexadepsipeptide synthetase activity.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties.

What is claimed is:

1. A mutant of a parent *Fusarium venenatum* strain, comprising a polynucleotide encoding a polypeptide and pyrG and amyA genes, wherein one or both of the pyrG and amyA genes are modified rendering the mutant strain deficient in the production of orotine-5'-monophosphate decarboxylase, alpha-amylase, or orotine-5'-monophosphate decarboxylase and alpha-amylase compared to the parent *Fusarium venenatum* strain when cultivated under identical conditions.

2. The mutant strain of claim 1, which produces at least 25% less of the orotine-5'-monophosphate decarboxylase, alpha-amylase, or orotine-5'-monophosphate decarboxylase and alpha-amylase compared to the parent *Fusarium venenatum* strain when cultivated under identical conditions.

3. The mutant strain of claim 1, which is completely deficient in the orotine-5'-monophosphate decarboxylase, alpha-amylase, or orotine-5'-monophosphate decarboxylase and alpha-amylase compared to the parent *Fusarium venenatum* strain when cultivated under identical conditions.

4. The mutant strain of claim 1, which further comprises an alpA gene, wherein the alpA gene is modified rendering the mutant strain deficient in the production of an alkaline protease compared to the parent *Fusarium venenatum* strain when cultivated under identical conditions.

5. The mutant strain of claim 4, which produces at least 25% less of the alkaline protease compared to the parent *Fusarium venenatum* strain when cultivated under identical conditions.

6. The mutant strain of claim 4, which is completely deficient in the alkaline protease compared to the parent *Fusarium venenatum* strain when cultivated under identical conditions.

7. The mutant strain of claim 1, which further comprises one or both of the genes tri5 and dps1, wherein the one or both of the genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

8. The mutant strain of claim 7, which produces at least 25% less of the one or both enzymes of trichodiene synthase and cyclohexadepsipeptide synthetase compared to the parent *Fusarium venenatum* strain when cultivated under identical conditions.

9. The mutant strain of claim 7, which is completely deficient in the one or both enzymes trichodiene synthase and cyclohexadepsipeptide synthetase compared to the parent *Fusarium venenatum* strain when cultivated under identical conditions.

10. The mutant strain of claim 1, wherein the polypeptide is native or foreign to the *Fusarium venenatum* strain.

11. A method for obtaining the mutant of a parent *Fusarium venenatum* strain of claim 1, comprising:
   (a) modifying pyrG and amyA genes in the parent *Fusarium venenatum* strain; and
   (b) identifying a mutant strain from step (a) wherein one or both of the pyrG and amyA genes are modified rendering the mutant strain deficient in the production of orotine-5'-monophosphate decarboxylase, alpha-amylase, or orotine-5'-monophosphate decarboxylase and alpha-amylase compared to the parent *Fusarium venenatum* strain when cultivated under identical conditions.

12. The method of claim 11, wherein the mutant strain produces at least 25% less of the orotine-5'-monophosphate decarboxylase, alpha-amylase, or orotine-5'-monophosphate decarboxylase and alpha-amylase compared to the parent *Fusarium venenatum* strain when cultivated under identical conditions.

13. The method of claim 11, wherein the mutant strain is completely deficient in the orotine-5'-monophosphate decarboxylase, alpha-amylase, or orotine-5'-monophosphate decarboxylase and alpha-amylase compared to the parent *Fusarium venenatum* strain when cultivated under identical conditions.

14. The method of claim 11, further comprising modifying an alpA gene rendering the mutant strain deficient in the production of an alkaline protease compared to the parent *Fusarium venenatum* strain when cultivated under identical conditions.

15. The method of claim 14, wherein the mutant strain produces at least 25% less of the alkaline protease compared to the parent *Fusarium venenatum* strain when cultivated under identical conditions.

16. The method of claim 14, wherein the mutant strain is completely deficient in the alkaline protease compared to the parent *Fusarium venenatum* strain when cultivated under identical conditions.

17. The method of claim 11, further comprising modifying one or both of the genes tri5 and dps1, rendering the mutant strain deficient in the production of one or both enzymes trichodiene synthase and cyclohexadepsipeptide synthetase, respectively, compared to the parent *Fusarium venenatum* strain when cultivated under identical conditions.

18. The method of claim 17, wherein the mutant strain produces at least 25% less of the one or both enzymes of trichodiene synthase and cyclohexadepsipeptide synthetase compared to the parent *Fusarium venenatum* strain when cultivated under identical conditions.

19. The method of claim 17, wherein the mutant strain is completely deficient in the one or both enzymes trichodiene synthase and cyclohexadepsipeptide synthetase compared to the parent *Fusarium venenatum* strain when cultivated under identical conditions.

20. A method of producing a polypeptide, comprising:
(a) cultivating the mutant of a parent *Fusarium venenatum* strain of claim 1 in a medium for the production of the polypeptide, wherein the mutant strain comprises a polynucleotide encoding the polypeptide and pyrG and amyA genes, wherein one or both of the pyrG and amyA genes are modified rendering the mutant strain deficient in the production of orotine-5'-monophosphate decarboxylase, alpha-amylase, or orotine-5'-monophosphate decarboxylase and alpha-amylase compared to the parent *Fusarium venenatum* strain when cultivated under identical conditions; and
(b) recovering the polypeptide from the cultivation medium.

21. The method of claim 20, wherein the mutant strain produces at least 25% less of the orotine-5'-monophosphate decarboxylase, alpha-amylase, or orotine-5'-monophosphate decarboxylase and alpha-amylase compared to the parent *Fusarium venenatum* strain when cultivated under identical conditions.

22. The method of claim 20, wherein the mutant strain is completely deficient in the orotine-5'-monophosphate decarboxylase, alpha-amylase, or orotine-5'-monophosphate decarboxylase and alpha-amylase compared to the parent *Fusarium venenatum* strain when cultivated under identical conditions.

23. The method of claim 20, wherein the mutant strain further comprises an alpA gene, wherein the alpA gene is modified rendering the mutant strain deficient in the production of an alkaline protease compared to the parent *Fusarium venenatum* strain when cultivated under identical conditions.

24. The method of claim 23, wherein the mutant strain produces at least 25% less of the alkaline protease compared to the parent *Fusarium venenatum* strain when cultivated under identical conditions.

25. The method of claim 23, wherein the mutant strain is completely deficient in the alkaline protease compared to the parent *Fusarium venenatum* strain when cultivated under identical conditions.

26. The method of claim 20, wherein the mutant strain further comprises one or both of the genes tri5 and dps1, wherein the one or both of the genes are modified rendering the mutant strain deficient in the production of one or both enzymes trichodiene synthase and cyclohexadepsipeptide synthetase, respectively, compared to the parent *Fusarium venenatum* strain when cultivated under identical conditions.

27. The method of claim 26, wherein the mutant strain produces at least 25% less of the one or both enzymes of trichodiene synthase and cyclohexadepsipeptide synthetase compared to the parent *Fusarium venenatum* strain when cultivated under identical conditions.

28. The method of claim 26, wherein the mutant strain is completely deficient in the the one or both enzymes of trichodiene synthase and cyclohexadepsipeptide synthetase compared to the parent *Fusarium venenatum* strain when cultivated under identical conditions.

29. The method of claim 20, wherein the polypeptide is native or foreign to the *Fusarium venenatum* strain.

* * * * *